(12) United States Patent
Striegler et al.

(10) Patent No.: US 12,245,591 B2
(45) Date of Patent: Mar. 11, 2025

(54) TEMPLATED ANTIMICROBIAL MICROGELS AND METHODS OF MAKING AND USING THE SAME

(71) Applicant: THE BOARD OF TRUSTEES OF THE UNIVERSITY OF ARKANSAS, Little Rock, AR (US)

(72) Inventors: Susanne Striegler, Fayetteville, AR (US); Babloo Sharma, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 693 days.

(21) Appl. No.: 17/428,512

(22) PCT Filed: Feb. 5, 2020

(86) PCT No.: PCT/US2020/016771
§ 371 (c)(1),
(2) Date: Aug. 4, 2021

(87) PCT Pub. No.: WO2020/163462
PCT Pub. Date: Aug. 13, 2020

(65) Prior Publication Data
US 2022/0125056 A1   Apr. 28, 2022

Related U.S. Application Data

(60) Provisional application No. 62/801,358, filed on Feb. 5, 2019.

(51) Int. Cl.
*A01N 59/20* (2006.01)
*A01N 25/04* (2006.01)
*A61K 33/34* (2006.01)
*A61K 47/69* (2017.01)

(52) U.S. Cl.
CPC ............. *A01N 59/20* (2013.01); *A01N 25/04* (2013.01); *A61K 33/34* (2013.01); *A61K 47/6903* (2017.08); *A61K 47/6933* (2017.08)

(58) Field of Classification Search
CPC .... A01N 59/20; A01N 25/04; A61K 47/6933; A61K 47/6903; A61K 33/34
See application file for complete search history.

(56) References Cited

U.S. PATENT DOCUMENTS

| | | | |
|---|---|---|---|
| 5,395,541 | A | 3/1995 | Carpenter et al. |
| 6,355,858 | B1 | 3/2002 | Gibbins |
| 8,088,400 | B2 | 1/2012 | Toreki et al. |
| 2003/0032765 | A1 | 2/2003 | McDonald et al. |
| 2003/0068440 | A1 | 4/2003 | Ottersbach et al. |
| 2004/0116551 | A1 | 6/2004 | Terry |
| 2010/0204411 | A1 | 8/2010 | Erneta et al. |
| 2012/0078203 | A1 | 3/2012 | Gaube et al. |
| 2013/0338326 | A1 | 12/2013 | Steinberg et al. |
| 2014/0199356 | A1 | 7/2014 | Chason et al. |
| 2014/0199358 | A1 | 7/2014 | Chason et al. |
| 2015/0071982 | A1 | 3/2015 | Lee et al. |
| 2018/0021225 | A1 | 1/2018 | Lima et al. |

FOREIGN PATENT DOCUMENTS

| | | |
|---|---|---|
| EP | 1391153 | 2/2004 |
| EP | 2016828 | 1/2009 |
| EP | 2471827 | 7/2012 |
| JP | 03180123 | 8/1991 |
| JP | 1992351672 | 12/1992 |
| JP | 1996092019 | 4/1996 |
| JP | 1996099383 | 4/1996 |
| JP | 1999222402 | 8/1996 |
| JP | 1999222494 | 8/1999 |
| JP | 2001220464 | 8/2001 |
| JP | 2003073627 | 3/2003 |
| JP | 2003335864 | 11/2003 |
| WO | 2006000755 | 1/2006 |
| WO | 2007000591 | 1/2007 |
| WO | 2007024973 | 3/2007 |
| WO | 2007130734 | 11/2007 |
| WO | 2008089166 | 7/2008 |
| WO | 2009137016 | 11/2009 |
| WO | 2011088205 | 7/2011 |

(Continued)

OTHER PUBLICATIONS

S. Striegler, J.D. Barnett, and N.A. Dunaway. "Glycoside Hydrolysis with Sugar-Templated Microgel Catalysts," ACS Catal. 2012, 2, 50-55). (Year: 2012).*
H. Miller ("Synthesis of Microgel Polymers as Catalysts," Chemistry & Biochemistry Undergraduate Honors Theses by Hannah N. Miller, University of Arkansas at Fayetteville, May 2016. (Year: 2016).*
D. Fleming, L. Chahin, and K. Rumbaugh. "Glycoside Hydrolases Degrade Polymicrobial Bacterial Biofilms in Wounds," Antimicrob Agents Chemother 61:10, 1-9, 2017. (Year: 2017).*

(Continued)

*Primary Examiner* — Michael P Cohen
(74) *Attorney, Agent, or Firm* — Quarles & Brady, LLP

(57) ABSTRACT

Disclosed herein are antimicrobial materials comprising a carbohydrate-templated microgel and a plurality of metal ions complexed thereto. The carbohydrate-templated microgel comprises a network copolymer molecule comprising a monoacrylate monomer, a crosslinking monomer, and a ligand monomer and wherein the microgel is prepared by the copolymerization of the monoacrylate monomer, the crosslinking monomer, and the ligand monomer in the presence of a carbohydrate or a carbohydrate derivative. The microgels have antimicrobial activity and allow for implementation of multiple, simultaneous mechanisms of antimicrobial action.

16 Claims, 15 Drawing Sheets

(56) References Cited

FOREIGN PATENT DOCUMENTS

| WO | 2012089617 | 7/2012 |
|---|---|---|
| WO | 2013001172 | 1/2013 |
| WO | 2013102795 | 7/2013 |
| WO | 2014204407 | 12/2014 |
| WO | 2017168419 | 10/2017 |
| WO | 2017189589 | 11/2017 |
| WO | 2018174304 | 9/2019 |

OTHER PUBLICATIONS

N. Nishat, R. Rasool, S. Parveen, S.A. Khan. "New Antimicrobial Agents: The Synthesis of Schiff Base Polymers Containing Transition Metals and Their Characterization and Applications," Journal of Applied Polymer Science, vol. 122, 2756-2764 (2011). (Year: 2011).*
R. Kanso, E.A. Yancey' S. Striegler. "Illuminating the binding interactions of galactonoamidines during the inhibition of— galactosidase (*E. coli*)," Bioorg. Med. Chem. 24, (2016) 661-671. (Year: 2016).*
C-H. Hsu, et al. Iminosugar C Glycoside Analogues of α D GlcNAc-1-Phosphate: Synthesis and Bacterial Transglycosylase Inhibition, J. Org. Chem., 2014, 79, 8629-8637. (Year: 2014).*
M. G. Gichinga, S. Striegler, N. A. Dunaway, J. D. Barnett. "Miniemulsion polymers as solid support for transition metal catalysts," Polymer 51 (2010) 606-615. (Year: 2010).*
Raman, N.; Joseph, J., Novel metal-based antimicrobial agents of copper(II) complexes: Synthesis, spectral characterization and DNA interaction study, Russ. J. Inorg. Chem. 2010, 55, 1064-1074; 10.1134/s0036023610070120.
Reimers et al., "Predominant Droplet Nucleation in Emulsion Polymerization," Journal of Applied Polymer Science, vol. 60, 251-262 (1996).
Sharma, B. et al., "Modulating the Catalytic Performance of an Immobilized Catalyste with Maxtrix Effects—A Critical Evaluation," ACS Catal. 2018, 8, 7710-7718.
Sobola, A. O.; Watkins, G. M., Antimicrobial activity and Cu(ii) complexes of Schiff bases derived from ortho-aminophenol and salicylaldehyde derivatives, J. Chem. Pharm. Res. 2013, 5, 147-154, 148.
Striegler et al., "A Sugar Discriminating Binuclear Copper(II) Complex," J. Am. Chem. Soc. 2003, 125 (38), 11518-11524.
Striegler et al., "Evaluating Binuclear Copper(II) Complexes for Glycoside Hydrolysis," Inorg. Chem. 2010, 49 (6), 2639-2648.
Striegler et al., "Glycoside Hydrolysis with Sugar-Templated Microgel Catalysts," ACS Catal. 2012, 2 (1), 50-55.
Striegler et al., "Hydrolysis of Glycosides with Microgel Catalysts," Inorg. Chem. 2011, 50 (18), 8869-8878.
Striegler et al., "Macromolecular Salen Catalyste with Largely Enhanced Catalytic Activity," Org. Lett., vol. 10, No. 2, 2008, 241-244.
Striegler, S. et al., "Binuclear copper(II) complexes discriminating epimeric glycosides and x-B-glycosidic bonds in aqueous solution," J. Catal. 2016, 338, 349-364.
Striegler, S. et al., "Discrimination of chiral copper(II) complexes upon binding of galactonoamidine ligands," Dalton Trans. 2016, 45, 15203-15210.
Suksrichavalit, T.; Prachayasittikul, S.; Piacham, T.; Isarankura-Na-Ayudhya, C.; Nantasenamat, C.; Prachayasittikul, V., Copper complexes of nicotinic-aromatic carboxylic acids as superoxide dismutase mimetics, Molecules 2008, 13, 3040-3056; 10.3390/molecules13123040.
Takano, Y et al., "Benchmarking the Conductor-like Polarizable Continuum Model (CPCM) for Aqueous Solvation Free Energies of Neutral and Ionic Organic Molecules," J. Chem. Theory Comput. 2005, 1, 70-77.
Wang B et al., "Determination of protonation states of iminosugar-enzyme complexes using photoinduced electron transfer," Chem. Sci. 2017, 8, 7383-7393.

Wolfenden, R. et al., "Spontaneous Hydrolysis of Glycosides," J. Am. Chem. Soc. 1998, 120, 6814-6815.
Wolfenden, R., "Degrees of Difficulty of Water-Consuming Reactions in the Absence of Enzymes," Chem. Rev. 2006, 106, 3379-3396.
Wulff et al., "Design of Biomimetic Catalysts by Molecular Imprinting in Synthetic Polymers: The Role of Transition State Stabilization," Acc. Chem. Res. 2012, 45 (2), 239-247.
Wulff et al., "Enzyme-like Catalysis by Molecularly Imprinted Polymers," Chem. Rev. 2002, 102 (1), 1-28.
Xia, X.; Hu, Z., "Syntheis and Light Scattering Study of Microgels with Interpenetrating Polymer Networks," Langmuir 2004, 20 (6), 2094-2098.
International Searching Authority. International Search Report and Written Opinion for application PCT/US2020/016771. Mailed on Apr. 29, 2020.
Kahn et al. 'In-Situ Synthesis of CuO nanoparticles in P(NIPAM-co-AA) microgel, structural characterization, catalytic and biological applications', Arabian Journal of Chemistry, 2018, vol. 11, pp.g 897-909.
Kren et al. Glycosides in Medicine: The Role of Glycosidic Residue in Biological Activity,Current Medicinal Chemistry, 2001, vol. 8, pp. 1303-1328.
Sharma et al. 'Biomimetic Glycoside Hydrolysis by a Microgel Templated with a Competitive Glycosidase Inhibitor', ACS Catal. 2018, vol. 8, pp. 8788-8795.
Sharma, B. et al., "Crosslinked Microgels as Platform for Hydrolytic Catalysts," Biomacromolecules 2018, 19, 1164 -1174.
Adero, P. O. et al. "The Experimental Evidence in Support of Glycosylation Mechanisms at teh Sn1-Sn2 Interface," Chem. Rev. 2018.
Al-Manasir, N.et al., "Preparation and Characterization of Cross-Linked Polymeric Nanoparticles for Enhanced Oil Recovery Applications," J. Appl. Polym. Sci. 2009, 113 (3), 1916-1924.
Antonietti, M. et al., "Polyreactions in miniemulsions," Prog. Polym. Sci. 2002, 27 (4), 689-757.
Bartlett, P. A. et al., "Phosphonamidates as Transition-State Analogue Inhibitors of Thermolysin," Biochemistry 1983, 22, 4618-4624.
Becke, A. D., "Density-functional thermochemistry. III. The role of exact exchange," J. Chem. Phys. 1993, 98, 5648-5652.
Bhanvase et al., "Kinetic studies of semibatch emulsion copolymerization of methyl methacrylate and styrene in the presence of high intensity ultrasound and initiator," Chem. Eng. Process. 2014, 85 (Supplement C), 168-177.
Bhattacharya, S.et al., "Temperature-, pH-, and Magnetic-Field-Sensitive Hybrid Microgels," Small 2007, 3(4), 650-657.
Blahova, M.; Sokolik, J.; Sedlackova, S.; Burianova, E.; Mlynarcik, D., Antimicrobial activity of diazole(n-salicylidene-I-α-alaninate)-copper(ii) complexes, Cesk. Farm. 1993, 42, 137-140.
Bleriot, Y. et al., "Inhibition of glycosidases by substitued amidines," Bioorg. Med. Chem. Lett. 1995, 5, 2655-60.
Bleriot, Y. et al., "Syntheis of a Benzylamidine Derived from D-Mannose, A Potent Mannosidase Inhibitor," Tetrahedron Lett. 1994, 35, 1867-70.
Bryant, S. J.et al., "Cytocompatibility of UV and visible light photoinitiating systems on cultured NIH/3T3 fibroblasts in vitro," J. Biomater. Sci., Polym. Ed. 2000, 11 (5), 439-457.
Capek, I.et al., "Emulsion copolymerization of methyl methacrylate and ethyl acrylate, 2. Effect of emulsifier concentration and emulsifier blend composition on the polymerization behavior," Makromol. Chem. (1987), 188 (7), Abstract.
Chen,"Fluorescent pH Indicator. Spectrl Changes of 4-Methylumbelliferone," R. F Anal. Lett. 1968, 1(7), 423-428.
Chern et al., "Effects of Temperature on Styrene Emulsion Polymerization Kinetics," Polym. J. 1999, 31, 516.
Choi, S.-Y. et al., Enzymatic Characterization of Glycosidase Antibodies Raised against a Chair Transition State Analog and the Retained Catalytic Activity from the Expressed Single Chain Antibody Fragments Mol. Cells 2002, 13, 463-469.
Dimonie et al., "Role of Surfactants in Emulsioin Polymerization," Rev. Chim. (Bucureºti) 59, Nr. 11 (2008).

(56) References Cited

OTHER PUBLICATIONS

Donde, K. J.; Patil, V. R.; Malve, S. P., Antimicrobial effect of cu(ii) complexes containing oxime ligands, Acta Pol. Pharm. 2004, 61, 123-125.

Fan, Q.-H. et al., "Illuminating the binding interactions of galactonoamidines during the inhibition of β-galactosidase (*E. coli*)", Bioorg. Med. Chem. 2016, 24, 661-671.

Fan, Q.-H. et al., "Evaluating N-benzylgalactonoamidines as putative transition state analogs for β-galactoside hydrolysis†" Org. Biomol. Chem. 2014, 12, 2792-2800.

Fisher, S. et al., "Effects of cross-linking on the properties o fcarboxylic polymers. I. apparent dissociation constants of acrylic and methacrylic acid polymers1," J. Phys. Chem. 1956, 60, 1030-1032.

Frisken, B. J. et al.,"Revisiting the method of cumulants for the analysis of dynamic light-scattering data", Appl. Opt. 2001, 40 (24), 4087-4091.

Gajda, T. et al., "Crystal structure, solution properties and hydrolytic activity of an alkoxo-bridged dinuclear copper(II) complex, as a ribonuclease mode†", J. Chem. Soc., Dalton Trans. 2002, 1757-1763.

Ganem, "Inhibitors of Carbohydrate-Processing Enzymes: Design and Synthesis of Sugar-Shaped Heterocycles," B Acc. Chem. Res. 1996, 29, 340-347.

Ghaschghaie et al., "The tridentate metal-binding sites of the common glycoses †," Dalton Trans., (2010) 39, 5535-5543.

Gichinga, M. G. et al., "Miniemulsion polymers as solid support for transition metal catalysts," Polymer 2010, 51(3), 606-615.

Golker, K. et al., "The effect of crosslinking density on molecularly imprinted polymer morphology and recognition," Eur. Polym. J. 2016, 75, 423-430.

Gyurcsik, B. et al., "Carbohydrates as ligands: coordination equilibria and structure of the metal complexes," Coord. Chem. Rev. 2000, 203, 81-149.

Heck, M.-P. et al., "Cyclic Amidine Sugars as Transition-State Analogue Inhibitors of Glycosidases: Potent Competitive Inhibitors of Mannosidases," J. Am. Chem. Soc. 2004, 126, 1971-1979.

Kabalnov et al., "Ostwald Ripening in Emulsions, I. Direct Observations of Ostwald Ripening in Emulsions," Journal of Colloid and Interface Science, vol. 118, No. 2, Aug. 1987.

Kanso R., S. Striegler, "Multi gram-scale synthesis of galactothionolactam and its transformation into a galactonoamidine," Carbohydrate Research 346 (2011) 897-904.

Kanso, R. et al., "N-Benzylgalactonoamidines as potent b-galactosidase inhibitors," Tetrahedron 2012, 68, 47-52.

Kim, J. W. et al., "Monodisperse micron-sized cross-linked polystyrene particles. VI. Understanding of nucleated particle formation and particle growth," Colloid Polym. Sci. 2000, 278 (6), 591-594.

Klamt, A. et al., "COSMO: A New Approach to Dielectric Screening in Solvents with Explicit Expressions for the Screening Energy and its Gradient," J. Chem. Soc., Perkin Trans. 2 1993, 799-805.

Koppel et al., "Analysis of Macromolecular Polydispersity in Intensity Correlation Spectroscopy: The Method of Cumulants," J. Chem. Phys. 1972, 57 (11), 4814-4820.

Kuo et al., "Photoinitiated Polymerization of Styrene in Microemulsions," Macromolecules 1987, 20 (6), 1216-1221.

Landfester et al., "Formulation and Stability Mechanisms of Polymerizable Miniemulsions," Macromolecules 1999, 32, 5222-5228.

Landfester, "Synthesis of colloidal articles inminiemulsions," Annu. Rev. Mater.Res. (2006) 36:231-79.

Lee, C. et al., "Development of teh Colle-Salvetti correlation-erergy formula into a functional of the electron density," Phys. Rev. B: Condens. Matter Mater. Phys. 1988, 37, 785-789.

Lee, K.-C.; et al.,"Preparation of Highly Cross-linked, Monodisperse Poly(methyl methacrylate) Microspheres by Dispersion Polymerization; Part 1. Batch Processes," Macromol. Res. 2007, 15(3), 244-255.

Martínez, V. S. et al., "Synthesis, Characterization, and Influence of Synthesis Parameters on Particle Sizes of a New Microgel Family," Chem. 2007, 45 (17), 3833-3842.

Mitin, A. V. et al., "An improved 6-31G* basis set for first-row transition metals," J. Chem. Phys. 2003, 118, 7775-7782.

Mjos, K. D.; Polishchuk, E.; Abrams, M. J.; Orvig, C., Synthesis, characterization, and evaluation of the antimicrobial potential of copper(ii) coordination complexes with quinolone and p-xylenyl-linked quinolone ligands, J. Inorg. Biochem. 2016, 162, 280-285; 10.1016/j.jinorgbio.2016.02.026.

Murakami, Y. et al., "Artificial Enzymes," Chem. Rev. 1996, 96, 721-758.

Murphy, R. W.et al., "Effect of crosslinking on the physical and chemical properties of β-lactoglobulin (Blg) microgels," J. Colloid Interface Sci. 2017, 505, 736-744.

Overkleeft et al., "A Facile Transformation of Sugar Lactones to Azasugars," Tetrahedron vol. 50, No. 14, pp. 4215-4224 (1994).

Pedersen, C. M. et al., "On the nature of the electronic effect of multiple hydroxyl groups in the 6-membered ring—the effects are additive but steric hindrance plays a role too†", Org. Biomol. Chem. 2017, 15, 1164-1173.

Pickens, J. B. et al., "Arabinoamidine synthesis and its inhibition toward β-glucosidase (sweet almonds) in comparison to a library of galactonoamidines," Bioorg. Med. Chem. 2016, 24, 3371-3377.

Pickens, J. B. et al., "Evaluating hydrophobic galactonoamidines as transition state analogs for enzymatic β-galactosidase hydrolysis," Bioorg. Chem. 2018, 77, 144-151.

Pickens, J. B. et al.,"Picomolar inhibition of β-galactosidase (bovine liver) attributed to loop closure," Bioorg. Med. Chem. 2017, 25, 5194-5202.

Plamper et al., "Functional Microgels and Microgel Systems," Acc. Chem. Res. (2017), 50, 131-140.

* cited by examiner

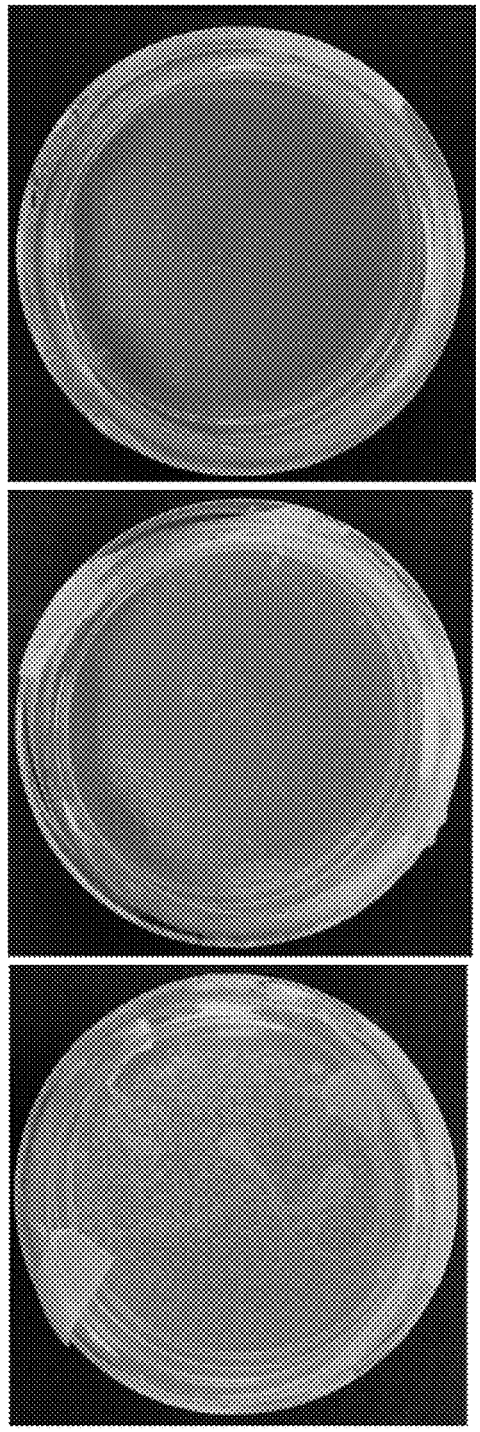
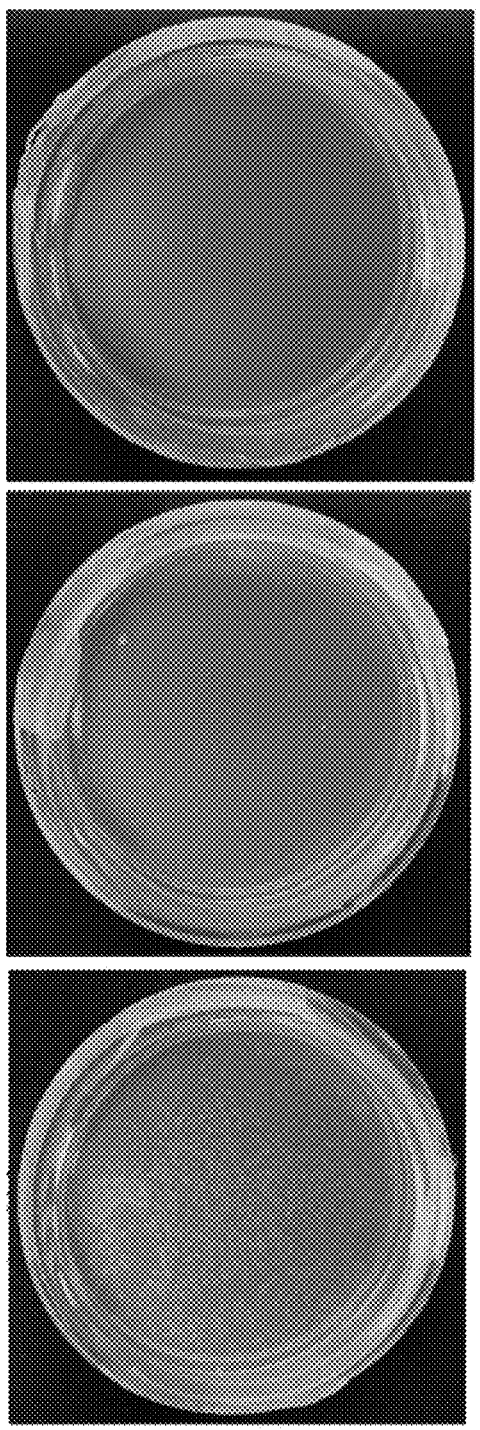
Figure 29A, Figure 29B, Figure 29C, Figure 29D, Figure 29E, Figure 29F

TEMPLATED ANTIMICROBIAL MICROGELS AND METHODS OF MAKING AND USING THE SAME

CROSS-REFERENCE TO RELATED APPLICATIONS

This patent application is a national stage filing under 35 U.S.C. § 371 of International Patent Application No. PCT/US2020/016771, filed Feb. 5, 2020, which claims the benefit of priority of U.S. Provisional Application Ser. No. 62/801,358, filed Feb. 5, 2019, the contents of each are incorporated by reference in their entireties.

STATEMENT OF GOVERNMENT SUPPORT

This invention was made with government support under CHE-1305543 awarded by the National Science Foundation. The government has certain rights in the invention.

BACKGROUND

Antimicrobial resistance is increasing in the United States and worldwide. Infections with drug-resistant bacteria result in prescription of higher doses of drugs, addition of treatments with higher toxicity, longer hospital stays, and increased mortality. However, many bacteria express resistance genes that allow for reduced uptake and/or increased efflux of specific types of antibiotics rendering those compounds ineffective. Typically, antibiotics target and disrupt the synthesis of bacterial cell walls, which is a composite macromolecule consisting of peptidoglycan layers for both gram-positive and -negative bacteria. Due to its complex nature and constant modifications, medicinal and synthetic organic chemists face an ongoing need for improved chemical methods and tools to develop antimicrobial compounds with high killing potency toward a broad spectrum of bacteria.

BRIEF SUMMARY OF THE INVENTION

Disclosed herein are antimicrobial material having catalytic activity and methods of making and using the same. The antimicrobial or catalytic material comprises a carbohydrate-templated microgel, wherein the carbohydrate-templated microgel comprises a network copolymer molecule comprising a monoacrylate monomer, a crosslinking monomer, and ligand monomer. The antimicrobial material may also comprise a plurality of metal ions complexed to the ligand of the carbohydrate-templated microgel. The carbohydrate-templated microgel is prepared by the copolymerization of the monoacrylate monomer, the crosslinking monomer, and the ligand monomer in the presence of a carbohydrate or a carbohydrate derivative.

In some embodiments, the monoacrylate monomer comprises one or more compounds of the formula $CH_2CHC(=O)OR$ and/or $CH_2C(CH_3)C(=O)OR$ wherein R is selected from a branched or unbranched, substituted or unsubstituted alkyl, a branched or unbranched, substituted or unsubstituted cycloalkyl, a branched or unbranched, substituted or unsubstituted aryl, or any combination thereof. In some embodiments, the crosslinking monomer comprises one or more compounds selected from the group consisting of a diacrylate, a triacrylate, a tetraacrylate, a pentaacrylate, a hexaacrylate, an alkoxylated crosslinking monomer thereof, or any combination thereof. In some embodiments, the ligand monomer comprises VB(bpdpo), VB(bsdpo), or VB(IDA). In some embodiments, the plurality of metal ions comprise a plurality of copper ions. In some embodiments, the carbohydrate is a monosaccharide or a disaccharide. In some embodiments, the carbohydrate derivative is a glycosidase inhibitor and/or a glyconoamidine.

Another aspect of the invention is a method for inhibiting proliferation of or killing a microbe. The method may comprise contacting the microbe with any of the compositions described herein.

Another aspect of the invention is a method for treating a microbial infection. The method may comprise administering any of the compositions described herein to a subject in need of a treatment for a microbial infection.

Another aspect of the invention is methods for hydrolyzing a glycosidic bond. The method may comprise contacting any of the compositions described herein with a substrate, wherein the substrate comprises a carbohydrate or a carbohydrate derivative.

Another aspect of the invention is a method for preparing an article having lowered susceptibility to the formation of a biofilm thereon. The method may comprise applying any of the compositions described herein to a surface of the article.

Additional aspects of the invention provide a pharmaceutical composition or an article having a lowered susceptibility to the formation of a biofilm thereon comprising any of the compositions described herein.

Another aspect of the invention is a method for preparing the antimicrobial materials described herein. The method may comprise providing an ultrasheered prepolymerization miniemulsion, the ultrasheered prepolymerization miniemulsion comprising (i) a monoacrylate monomer, (ii) a crosslinking monomer, (iii) a ligand monomer, (iv) a first metal ion solution, (v) a hydrophobe, and a (vi) a surfactant; providing a carbohydrate or a carbohydrate derivative; and irradiating the ultrasheered prepolymerization miniemulsion in the presence of the carbohydrate or the carbohydrate derivative, thereby photoinitiating the copolymerization the monoacrylate monomer, the crosslinking monomer, and the ligand monomer to prepare a carbohydrate-templated microgel as described herein.

In some embodiments, the ultrasheered prepolymerization miniemulsion further comprises a buffer. In some embodiments, the method further comprises sonicating a mixture comprising the monoacrylate monomer, the crosslinking monomer, the ligand monomer, the metal ion solution, the hydrophobe, and the surfactant, thereby preparing the ultrasheered prepolymerization miniemulsion. In some embodiments, the method further comprises providing an initiator and irradiating the ultrasheered prepolymerization miniemulsion in the presence of the carbohydrate or the carbohydrate derivative and the initiator. In some embodiments, the method further comprises dialyzing the carbohydrate-templated microgel. In some embodiments, the method further comprises providing a second metal ion solution and activating the material. In some embodiments, the surfactant comprises an anionic surfactant or a neutral surfactant. In some embodiments, the hydrophobe comprises $C_6$-$C_{24}$ saturated or unsaturated, branched or unbranched, substituted or unsubstituted alkyl, a $C_6$-$C_{24}$ saturated or unsaturated, branched or unbranched alkyl or cycloalkyl; a $C_6$-$C_{24}$ saturated or unsaturated, branched or unbranched, substituted or unsubstituted fatty acid; a triglyceride comprising independently selected $C_6$-$C_{24}$ saturated or unsaturated, branched or unbranched, substituted or unsubstituted fatty acids; a $C_5$-$C_{24}$ saturated or unsaturated, branched or unbranched aryl; a hydrophobic caged oligomeric or polymeric substance; or saturated or unsaturated, branched or unbranched, substituted or unsubstituted hydrophobic polymer; or any combination thereof.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 5B) 50 mol % EGDMA, 50 mol % BA and VBbpdpo (pink pentagon, 0.5 mol %) or styrene (blue pentagon, 1 mol %).

FIGS. 29A-29F shows growth of E. coli cells on Müller-Hinton/agar after 12 h without additive (FIG. 29A), and in presence of and $Cu_2$bpdpo (FIG. 29B); lysozyme (FIG.

Figure 1:
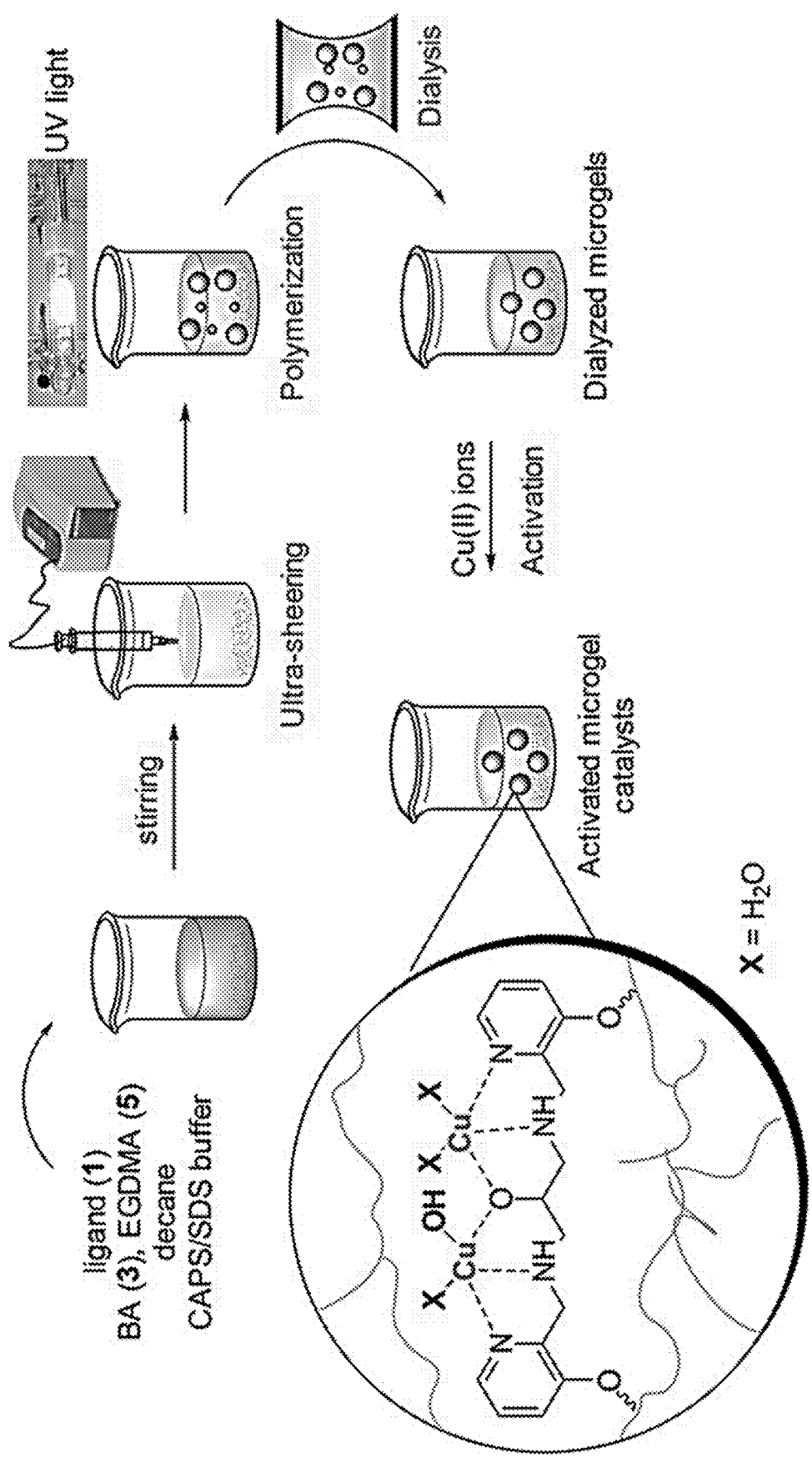
FIG. 1 provides a strategy for a facile one-pot synthesis of crosslinked microgels and catalyst activation.

29C), and microgel droplets $^{Cu_2L}P_{gal}$ (40%) (FIG. 29D), $^{Cu_2L}P_1$ (60%) (FIG. 29E), and $^{Cu_2L}P_1$ (60%) (FIG. 29F).

DETAILED DESCRIPTION OF THE INVENTION

Disclosed herein are templated antimicrobial microgels and methods of making and using the same. The microgels disclosed herein allow for implementation of multiple, simultaneous mechanisms of antimicrobial action. The development of microbial resistance against these microgels is thus unlikely, as multiple coinciding gene mutations in the same bacterial cell would be required. As demonstrated herein, the disclosed microgels are among the most potent biomimetic catalysts known and surpass the potency of catalytic antibodies. The observed catalytic proficiency of templated microgels is a result of the synergy of catalytic activity of the metal complex, hydrolysis-supporting matrix effects, and matrix templating.

Enzymes accelerate reactions through very strong stabilization of the corresponding transition states using multiple interactions. Glycosidases are among the most proficient enzymes known that use a sophisticated combination of interactions to support and stabilize the transition state of glycoside hydrolyses. [Wolfenden, R. et al. J. Am. Chem. Soc. 1998, 120, 6814-6815] While catalytically active amino acids, such as glutamic and aspartic acids, are crucial for the catalytic turnover in both retaining and inverting glycosidases, additional stabilizing interactions with a myriad of other amino acids in the active site are equally important. The glycon of a substrate is thereby strongly stabilized by H-bonding or electrostatic interactions, while the aglycon frequently engages in $\pi$-$\pi$ or CH-$\pi$ stacking, H-bonding, and/or van-der-Waals interactions. The synergy of all those contributions results in highly proficient and selective catalysts.

Additionally, induced fit, chair flattening in an $S_N2$-like transition state and loop closure interactions upon substrate binding are noted to support the catalytic turnover. [Pedersen, C. M. et al. Org. Biomol. Chem. 2017, 15, 1164-1173; Adero, P. O. et al. Chem. Rev. 2018; Pickens, J. B. et al. Med. Chem. 2017, 25, 5194-5202] Anticipated key interactions of the enzymatic glycoside turnover can be implemented in enzyme mimics separately or used in selected combinations to probe their contributions to the overall catalytic performance.

To transfer the principles found in Nature into biomimetic catalysis and guide the development of efficient homogeneous catalysts, stabilizing interactions beyond the first coordination sphere of a transition metal complex are often necessary. In this context, mimicking the variety of contributions found in an active site of an enzyme into a second coordination sphere close to the metal core of a synthetic catalyst is of particular interest. Controlling electronic and structural properties in a secondary coordination sphere are crucial for the construction of supramolecular assemblies with improved catalytic activity.

We previously synthesized water-dispersed microgels at elevated temperatures that immobilized pentadentate ligand VBbpdpo as a precursor of dormant binuclear catalysts. [Striegler et al. ACS Catal. 2012, 2 (1), 50-55; Striegler et al. Inorg. Chem. 2011, 50 (18), 8869-8878] After activation with Cu(II) ions, the microgel catalysts show catalytic efficiency for the hydrolyses of selected glycosides that is 14.5-fold higher ($k_{cat}/k_{non}$=160000 M) than the efficiency of their low molecular weight analog Cu$_2$bpdpo (2) ($k_{cat}/k_{non}$=11000 M) in alkaline solution. These observations indicate substantial contributions of the matrix to the overall observed catalytic performance.

The amount of immobilized ligand in the polymers was quantitative and determined by elemental analysis of the overall nitrogen content of the material. The catalyst activation with Cu(II) ions was monitored by isothermal titration calorimetry and confirmed as near quantitative as well. Attempts to characterize the ligand content in the microgels by NMR spectroscopy failed due to its small amount relative to the surrounding matrix ($\leq$1 mol %). [Striegler et al., Inorg. Chem. 2010, 49 (6), 2639-2648] However, analysis using EPR spectroscopy disclosed that the acceleration of the reaction is correlated to an intact immobilized complex and not to a distorted ligand or randomly distributed Cu(II) ions. [Striegler 2011]

The free radical polymerization of equimolar mixtures of butyl acrylate (BA) and styrene proceeds effortlessly after ultrasheering in aqueous solution when initiated thermally between 70 and 120° C., as observed by us and others. [Strieger 2012; Strieger 2011; Kuo et al. Macromolecules 1987, 20 (6), 1216-1221] Up to 1 mol % of the ligand relative to the overall monomer content can be immobilized applying this protocol. Higher ligand amounts were found to lead to monomer agglomeration and unstable miniemulsions. While the overall monomer conversion is typically above 95%, the use of elevated temperatures is not favorable for the design of the first coordination sphere of a catalyst via matrix effects. [Wulff et al. Acc. Chem. Res. 2012, 45 (2), 239-247.] The increased vibrational energy of all molecules under these conditions may hamper efforts to tailor its immediate electronic and structural environment and thus necessitates a different approach. [Wulff 2012; Wulff et al. Chem. Rev. 2002, 102 (1), 1-28] Consequently, a polymerization protocol allowing material preparation at ambient temperature or below lends itself as an ideal strategy for the synthesis of such catalytic entity. Contrary to thermally initiated free radical polymerization, UV-initiated polymerizations can be performed under the desired conditions avoiding enlarged vibrational energy. Additional advantages include shortened polymerization times, a limited number of side reactions including chain-transfer reactions, and polymer growth with spatial and temporal resolutions.

The photoinitiated polymerization of an equimolar mixture of BA and styrene using our previously developed strategy was obstructed at ambient temperature and found negligible at 0° C. Similar observations were reported by others when using styrene, BA, or mixtures thereof for freeradical polymerizations at temperatures below 70° C. [Bhanvase et al. Chem. Eng. Process. 2014, 85 (Supplement C), 168-177; Chern et al. Polym. J. 1999, 31, 516.] Gravimetric analyses of sample aliquots disclosed that even the use of a powerful high-pressure Hg lamp as a light source and concentrations of various photoinitiators of up to 20 mol % remained futile (data not shown). To advance polyacrylate microgels as a general platform and support of catalysts with tailored matrix effects, we thus introduce here a new polymerization protocol that is applicable to photoinitiated free-radical polymerization at ambient temperature or below using a crosslinking monomer.

The microgels described herein catalyze the hydrolysis of both $\beta$- and $\alpha$-glycosidic bonds. The catalytic activity of the microgels results in a 5 orders of magnitude increase in the rate of reaction over the uncatalyzed reaction. Moreover, the microgels result in substantial increases in reaction rate over the low molecular weight analog.

In addition, the microgels described herein have antimicrobial activity. As demonstrated in the examples that follow, the microgels are effective in hydrolyzing model compounds of the bacterial polysaccharide layer and demonstrate inhibition of the proliferation of or result in killing of microbes with their native defenses to the breakdown of their cellular wall or envelope.

Templated Microgels

The templated microgels described herein comprise a network copolymer prepared by the copolymerization of the monomers in the presence of a carbohydrate or a carbohydrate derivative. The templated microgels comprises three different monomers: a monoacrylate monomer, a crosslinking monomer, and a ligand monomer. In addition, the microgels are activated by complexing metal ions to the ligand moieties immobilized in the templated microgel.

The monoacrylate monomer may comprise one or more compounds of the formula $CH_2CHC(=O)OR$ and/or $CH_2C(CH_3)C(=O)OR$. R may be selected from a branched or unbranched, substituted or unsubstituted alkyl, a branched or unbranched, substituted or unsubstituted cycloalkyl, a branched or unbranched, substituted or unsubstituted aryl, or any combination thereof. Selection of monoacrylate monomers for the proposed systematic substitution is driven by binding interactions between amino acids in the active site of β-galactosidases and galactonoamidines with transition state-like features. H-bond interactions between matrix and the glycon of the substrate will be most relevant for stabilization of the transition state that in turn translates into advanced catalytic turnover. Hydrophobic, CH-π and π-π stacking interactions between matrix and the aglycon of the glycoside will provide further supporting interactions during the transition state of glycoside hydrolyses in biomimetic microgels, but are not predominant.

The monoacrylate monomer may comprise monoacrylates having R groups as defined above to allow for H-bonding interactions. Such R groups may comprise substituents having hydroxyl, alkoxyl, carboxy, or amino substituents. Suitably, the monoacrylate monomer may comprise an R groups selected from a branched or unbranched $C_1$-$C_{12}$ alkylhydroxy, a branched or unbranched $C_1$-$C_{12}$ alkylalkoxyl, a branched or unbranched $C_1$-$C_{12}$ alkylcarboxy, a branched or unbranched $C_1$-$C_{12}$ alkylamino, or any combination thereof. In some embodiments, R is selected from a branched or unbranched $C_1$-$C_6$ or $C_1$-$C_4$ alkylhydroxy, a branched or unbranched $C_1$-$C_6$ or $C_1$-$C_4$ alkylalkoxyl, a branched or unbranched $C_1$-$C_6$ or $C_1$-$C_4$ alkylcarboxy, a branched or unbranched $C_1$-$C_6$ or $C_1$-$C_4$ alkylamino, or any combination thereof. Exemplary R groups include, without limitation, ethylhydroxy, ethylmethoxy, ethylcarboxy, and ethylamino groups.

The monoacrylate monomer may comprise monoacrylates having R groups selected to allow for CH-π or π-π interactions. Such R groups may comprise an aryl moiety such as a phenyl ring. Suitably, the monoacrylate monomer may comprise an R group selected from a branched or unbranched, substituted or unsubstituted $C_5$-$C_{18}$ aryl or a branched or unbranched, substituted or unsubstituted $C_5$-$C_{12}$ aryl groups. Exemplary R groups include, without limitation, phenyl and benzyl.

The monoacrylate monomer may comprise monoacrylates having R groups selected to allow for hydrophobic interactions. Such R groups may lack a H-bonding moiety, a polar moiety, and/or a charged moiety. Suitably, the monoacrylate monomer may comprise an R group selected from a $C_1$-$C_{18}$ unsubstituted, branched or unbranched alkyl; a $C_5$-$C_{18}$ unsubstituted, branched or unbranched aryl; a $C_3$-$C_{18}$ unsubstituted, branched or unbranched cycloalkyl. In some embodiments, the R groups may be selected from a $C_1$-$C_{12}$ unsubstituted, branched or unbranched alkyl; a $C_5$-$C_{12}$ unsubstituted, branched or unbranched aryl; a $C_3$-$C_{12}$ unsubstituted, branched or unbranched cycloalkyl. Exemplary R groups include, without limitation, butyl, benzyl, dodecyl, and methylcyclohexyl.

Suitably the monoacrylate monomer may comprise more than one monoacrylate. Miniemulsions with up to 20 wt % of hydrophilic monomers are colloidally stable without diffusion of the hydrophilic monomers out of the nanodroplet and into the aqueous layer. Colloidal stability will be ensured by using a hydrophobe and by promoting electrostatic stabilization of the nanodroplets. These interaction will be provided by employing optimized blends consisting of neutral and ionic surfactants. The same approach may be used to avoid undesirable bimodal distributions of particle sizes.

In some embodiments, the monoacrylate monomer may comprise one monoacrylate selected to provide H-bonding interactions and another different monoacrylate selected to provide CH-π or π-π interactions or hydrophobic interactions. In some embodiments, the monoacrylate monomer may comprise one monoacrylate selected to provide CH-π or π-π interactions and another different selected to provide H-bonding interactions or hydrophobic interactions. In some embodiments, the monoacrylate monomer may comprise one monoacrylate selected to provide hydrophobic interactions and another different monoacrylate selected to provide H-bonding interactions or CH-π or π-π interactions. In certain embodiments, the monoacrylate monomer comprises a monoacrylate selected to provide CH-π or π-π interactions, another different monoacrylate selected to provide H-bonding interactions, and yet another different monoacrylate selected to provide hydrophobic interactions.

In some embodiments, the monoacrylate monomer may comprises two different monoacrylates and each are selected to provide H-bonding interactions or each selected to provide CH-π or π-π interactions or each selected to provide hydrophic interactions. When the monoacrylate monomer comprises two different monoacrylates and each are selected to provide the same type of interaction, the monomer may comprise yet another monoacrylate selected to provide a different type interaction. For example, the monomer may comprise two (2) different monoacrylates selected to provide H-bonding interactions and another selected to provide CH-π or π-π interactions or hydrophobic interactions, the monomer may comprise two (2) different monoacrylates selected to provide CH-π or π-π interactions and another selected to provide H-bonding or hydrophobic interactions, or the monomer may comprise two (2) different monoacrylates selected to provide hydrophobic interactions and another selected to provide CH-π or π-π interactions or H-bonding interactions.

When the monoacrylate monomer mixture comprises more than one different monoacrylate, the relative amount as measured by mol % or wt % of each monoacrylate may be selected over wide ranges. For example, a binary monoacrylate monomer may comprise between 1-99 mol % of a first monoacrylate and 99-1 mol % of a second monoacrylate, between 10-90 mol % of a first monoacrylate and 90-10 mol % of a second monoacrylate; between 25-75 mol % of a first monoacrylate and 75-25 mol % of a second monoacrylate; or between 40-60 mol % of a first monoacrylate and 60-40 mol % of a second monoacrylate.

The crosslinking monomer may comprise one or more compounds selected from the group consisting of a diacrylate, a triacrylate, a tetraacrylate, a pentaacrylate, a hexaacrylate, or any combination thereof. Crosslinking monomers having a greater number of acrylate moieties promote higher degrees of branching and higher rigidity of the microgel matrix at lower molar amounts of crosslinking monomer. As an example, microgels prepared from 60 mol % EGDMA allow variation of butyl acrylate monomer between 0 and 40 mol % to generate catalysis-supporting matrix effects. By contrast, a microgel prepared from 30 mol % PETA will have the same degree of branching as the microgel described first, but will allow substitutions of the butyl acrylate monomer between 0 and 70 mol % thereby providing an opportunity to fine-tune the microgel architecture and optimize the catalytic proficiency to a significantly larger extent. Thus, alteration of the crosslinking agent will result in high flexibility to adjust matrix compositions in correlation to the resulting catalytic proficiency of the material.

Suitably, the crosslinking monomer may comprise a compound of formula

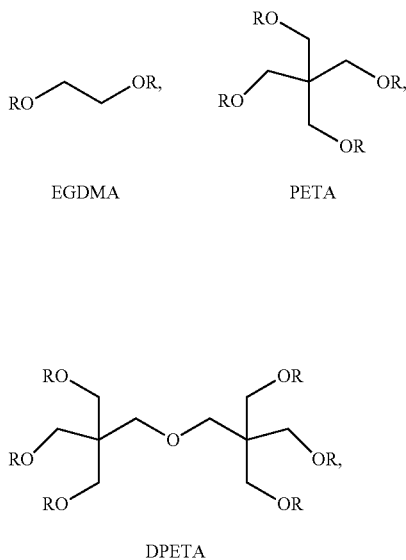

or any combination thereof. Each R is independently selected from hydrogen, —C(=O)CHCH$_2$, and —C(=O)C(CH$_3$)CH$_2$ provided that the compound comprises at least two R independently selected from —C(=O)CHCH$_2$ and —C(=O)C(CH$_3$)CH$_2$. In some embodiments, the crosslinking monomer may be an alkoxylated crosslinking monomer such as an ethoxylated crosslinking monomer. The alkoxylated crosslinking monomer may be an alkoxylated diacrylate, an alkoxylated triacrylate, an alkoxylated tetraacrylate, an alkoxylated pentaacrylate, an alkoxylated hexaacrylate, or any combination thereof. An exemplary alkoxylated crosslinking monomer is an alkoxylated tetraacrylate such as

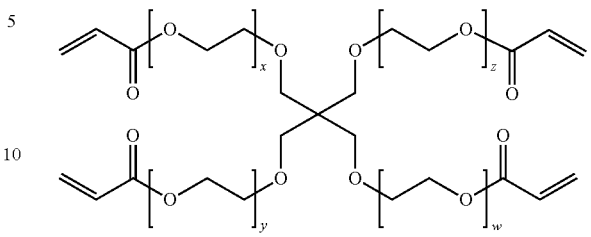

where n=w+x+y+z and n is between 1 and about 10.

The ligand monomer comprises monomer molecules having a ligand moiety capable of complexing with two metal ions. Suitably, the ligand moiety is a pentadentate ligand moiety. The catalyst selection is driven by the hydrolytic ability of resulting binuclear complexes over mononuclear analogues for the hydrolysis of glycosidic bonds. The distance between complexed metal ions may be tailored by modifying the backbone ligand. Suitably, the ligand monomer may comprise a compound of formula

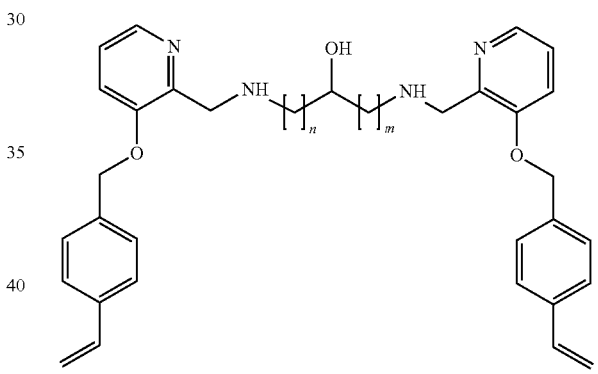

wherein n and m are independently selected from 1 or 2. In some embodiments, both n and m are equal to 2, n or m is equal to 1 and the other is equal to 2, or both n and m are equal to 1. When n and m are each equal to 1, the ligand is referred to as VB(bpdpo). When complexed with Cu ions, the Cu—Cu distance may be tailored from about 2.93 Å (where n=m=2) to about 3.36 Å (n=1, m=2) to about 3.50 Å (n=m=1) as determined in silico.

In some embodiments, the ligand monomer is VB(bsdpo)

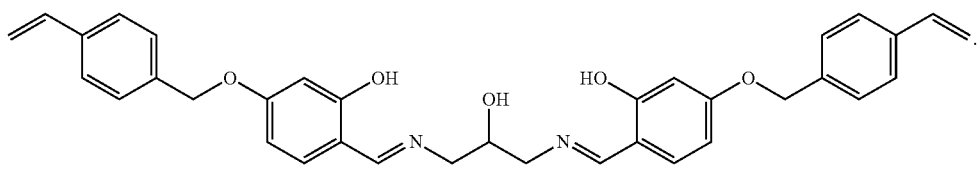 [SMILES: C=Cc1ccc(COc2ccc(/C=N/CC(O)C/N=C/c3ccc(OCc4ccc(C=C)cc4)cc3O)c(O)c2)cc1]

When VB(bspdo) is incorporated into the catalytic materials, this metal ligand may also coordinate two Cu ions

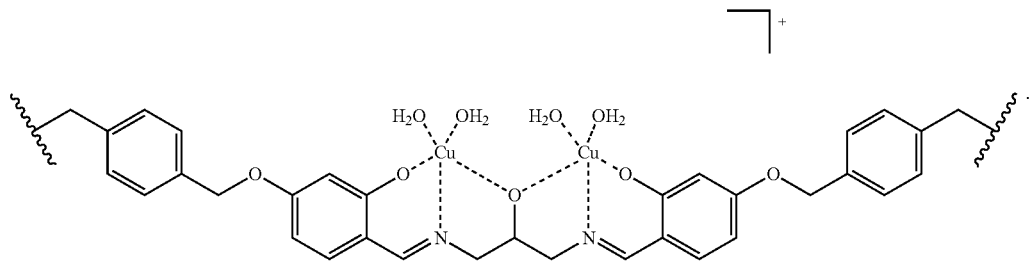

The complex is capable of exchanging the coordinated acetate against water and hydroxyl ions depending on the pH when exposed to water. [Striegler et al., Org. Lett., Vol. 10, No. 2, 2008, 241-244; Striegler et al., Inorg. Chem. 2011, 50, 8869-8878]

In other embodiments, the ligand monomer may be a tridentate ligand monomer. Suitably the ligand monomer may be N-(4-Vinylbenzyl)iminodiacetic acid, VB(IDA). When VB(IDA) is incorporated into catalytic materials, the metal ligand may coordinate one Cu ion

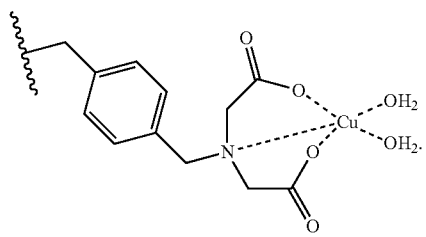

The relative proportion of the monoacrylate monomer and the crosslinking monomer may be varied over the relative amount as measured by mol % or wt % of each monoacrylate and may be selected over wide ranges. The mol % of the monoacrylate monomer relative to each of the three monomers, i.e., the monoacrylate monomer, the crosslinking monomer, and the ligand monomer, may be between 5-80 mol % and suitably between about 10-80 mol %, 15-80 mol %, 20-80 mol %, 25-80 mol %, 30-80 mol %, 35-80 mol %, 40-80 mol %, 10-70 mol %, 15-70 mol %, 20-70 mol %, 25-70 mol %, 30-70 mol %, 35-70 mol %, 40-70 mol %, 10-65 mol %, 15-65 mol %, 20-65 mol %, 25-65 mol %, 30-65 mol %, 35-65 mol %, or 40-65 mol %. The mol % of the crosslinking monomer relative to each of the three monomers, i.e., the monoacrylate monomer, the crosslinking monomer, and the ligand monomer, may be between 5-80 mol % and suitably between about 10-80 mol %, 15-80 mol %, 20-80 mol %, 25-80 mol %, 30-80 mol %, 35-80 mol %, 40-80 mol %, 10-70 mol %, 15-70 mol %, 20-70 mol %, 25-70 mol %, 30-70 mol %, 35-70 mol %, 40-70 mol %, 10-65 mol %, 15-65 mol %, 20-65 mol %, 25-65 mol %, 30-65 mol %, 35-65 mol %, or 40-65 mol %. Formation of the microgel is more sensitive to the inclusion of the ligand monomer and is typically included as a minor component. The ratio of the mol % of the monoacrylate monomer and the crosslinking monomer to the ligand monomer is typically greater than 98.0:2.0. Suitably the mol % is greater than 99.0:1.0 or 99.5:0.5.

The microgels described herein will form particles having sub-micron dimensions. Suitably, the microgels have a hydrodynamic diameter of less than 300 nm and in some cases less than about 275 nm, 250 nm, 225 nm, 200 nm, 175 nm, 150 nm, 125 nm, 100 nm, 75 nm, or 50 nm. In some embodiments, the particles have the morphology described in the Examples that follow.

The microgels are prepared by the copolymerization of the monoacrylate monomer, the crosslinking monomer, and the ligand monomer in the presence of a carbohydrate or a carbohydrate derivative. Suitably, carbohydrates include monosaccharides, disaccharides, trisaccharides, or polysaccharides. Exemplary monosaccharides include, without limitation, galactose, mannose, glucose, and fructose. Exemplary disaccharides include, without limitation, maltose, isomaltose, cellobiose, and gentibiose. Exemplary trisaccharides, include, without limitation, maltotriose, cellotriose, panose, and raffinose. Exemplary polysaccharides include, without limitation, amylose and cellulose.

For disaccharides or larger saccharides, the monomeric saccharide units may be bonded via α(1-2), α(1-4), α(1-6), β(1-4), or β(1-6) glycosidic bonds, including any combination thereof. For example, maltose is comprised of glucose monomers linked via a α(1-4) glycosidic bond, isomaltose is comprised of glucose monomers linked via a α(1-6) glycosidic bond, cellobiose is comprised of glucose monomers linked via a β(1-4) glycosidic bond, and centiobiose is comprised of glucose monomers linked via a β(1-6) glycosidic bond. The trisaccharide maltotriose comprises two α(1-4) glycosidic bonds while cellotriose comprises two β(1-4) bonds, panose comprises a α(1-4) glycosidic bond and a α(1-6) glycosidic bond, and raffinose comprises a α(1-2) glycosidic bond and a α(1-4) glycosidic bond. Amylose and cellulose comprises α(1-4) and β(1-4) glycosidic bonds, respectively.

Carbohydrate derivatives include modified carbohydrates where the modification includes the addition of a substituent other than a hydroxyl group or the replacement of a carbon or oxygen atom by another atom such as nitrogen. Carbohydrate derivatives may include a glyconoamidine, amino sugars, acidic sugars, deoxy sugars, sugar alcohols, glycosylamines, sugar phosphates, or glycoconjugates. Glycoconjugates include carbohydrates covalently linked with other chemical species such as proteins, peptides, lipids and saccharides such as glycoproteins, glycopeptides, peptidoglycans, glycolipids, glycosides and lipopolysaccharides, which are often involved in cell-cell interactions, including cell-cell recognition and in cell-matrix interactions.

Glyconoamidines, such as galactonoamidines, may be useful in preparing templated microgels because they are analogs of the transition state of glycoside hydrolyses. Galactonoamidines are competitive inhibitors. Galactonoamidines may comprise a compound of formula

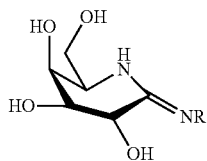

or its tautomer, wherein R is selected from the group consisting of a branched or unbranched, substituted or unsubstituted alkyl, or a branched or unbranched, substituted or unsubstituted cycloalkyl, a branched or unbranched, substituted or unsubstituted alkyl. Exemplary galactonoamidines include 2a-f

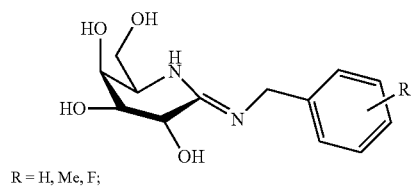

R = H, Me, F;

or where 2g-i

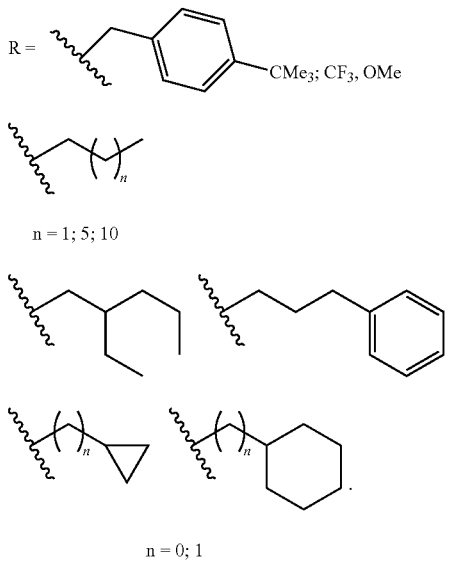

2j-l 2m, n 2o-r n = 0; 1

The exemplary galactonoamidines 2α-r are potent competitive inhibitors (Fan 2014a) with inhibition constants $K_i$ as low as 60 pM (for β-galactosidase from bovine liver). [Pickens 2017] This observation places galactonoamidines among the most potent competitive inhibitors for glycosidases known. The galactonoamidines feature $sp^2$-hybridization of the anomeric C-atom, a flattened chair, imitation of the partially positive ring-oxygen, and the lengthening of the glycosidic bond, which are all key elements of the $S_N2$-like enzymatic hydrolysis of glycosides. [Adero 2018]

Galactonoamidines coordinate metal ions of binuclear metal complexes. For example, amidine 2a chelates the binuclear complex $Cu_2bpdpo$ over three binding sites

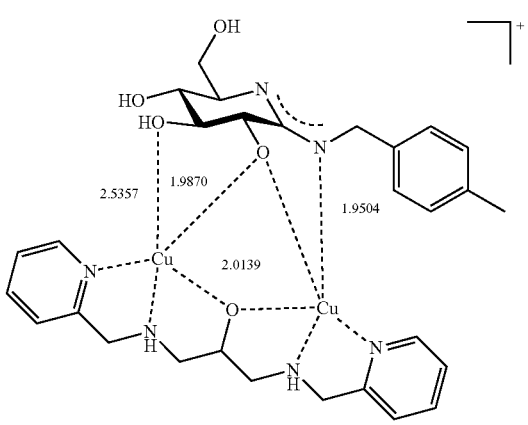

The coordination pattern conforms with a tridentate binding site model for carbohydrate coordination to metal complexes. [Gyurcsik 2000; Ghaschghaie 2010] The coordination sites of 2a include its deprotonated amidine function and hydroxyl groups at C-2 and at C-3. Similar H-bond interactions of the glycon moiety in 2a with amino acids are described above for the stabilization of the amidine in the active site of β-galactosidases. [Pickens 2018]

Galactonoamidines suitable for use in preparing the microgels disclosed herein may be synthesized starting from galactose via galactonolactam and galactothionolactam was developed based on reports by Overkleeft, Heck and Vasella. [Overkleeft 1994; Heck 2004; Kanso 2011]

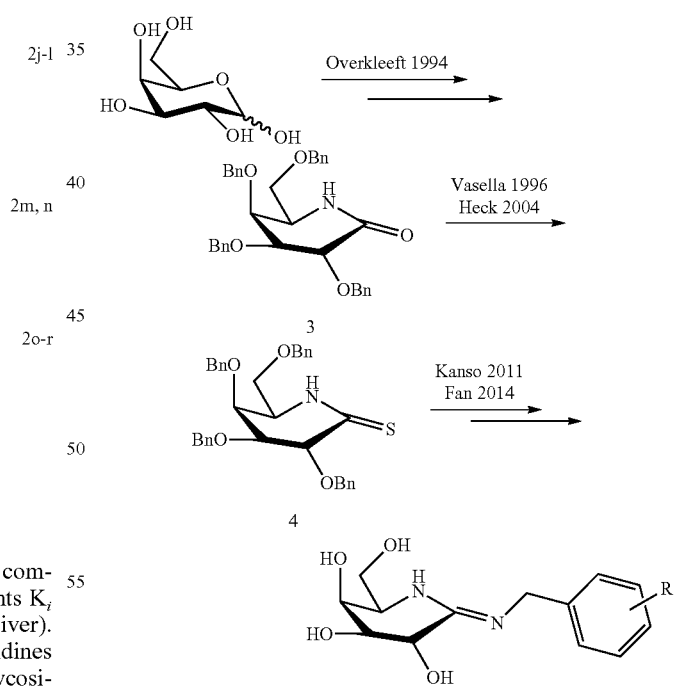

The microgels may be activated by the complexation of metal ions to the binuclear ligands. Suitably the metal ions are Cu ions.

Methods of Making Templated Microgels

The templated microgels described herein may be prepared by providing an ultrasheered prepolymerization miniemulsion, providing a carbohydrate or a carbohydrate derivative, and irradiating the ultrasheered prepolymerization miniemulsion in the presence of the carbohydrate or the carbohydrate derivative, thereby initiating the polymerization reaction. The resulting carbohydrate-templated microgel comprises a network copolymer molecule comprising (i) a monoacrylate monomer, (ii) a crosslinking monomer, and (iii) a ligand monomer and may have a plurality of metal ions complexed to the ligand moieties in the carbohydrate-templated microgel.

The ultrasheered prepolymerization miniemulsion may comprise (i) a monoacrylate monomer, (ii) a crosslinking monomer, (iii) a ligand monomer, (iv) a metal ion solution, (v) a hydrophobe, a (vi) a surfactant, a (vii) buffer, or any combination thereof. Components (i)-(iii) are described above.

The components of the ultrasheered prepolymerization miniemulsion may be selected to control Ostwald ripening, or the formation of larger droplets. The use of the hydrophobe differentiates the disclosed method from emulsion polymerization by the application of high shear through ultrasonication in the first step to generate very small droplets. In contrast to emulsion polymerization, the addition of hydrophobes prevents Ostwald ripening for about 100 hours, provides stability to the nanodroplets, and allows their treatment as individual nanoreactors. [Plamper 2017] The synthetic protocol extends UV-initiated photopolymerization of miniemulsions derived from acrylate and methacrylates in presence of crosslinking agents at ambient temperature and below. The copolymerization may be performed at a temperature less than 10° C., optionally less than 5° C. Thus, this synthetic protocol is ideal for the immobilization of transition metal complexes in presence of sensitive biomacromolecules to introduce catalytic function in microgels (FIG. 1).

The hydrophobe may be selected from a saturated or unsaturated, branched or unbranched, substituted or unsubstituted $C_6$-$C_{24}$ alkyl, a saturated or unsaturated, branched or unbranched $C_6$-$C_{24}$alkyl or $C_6$-$C_{24}$ cycloalkyl; a saturated or unsaturated, branched or unbranched, substituted or unsubstituted $C_6$-$C_{24}$ fatty acid; a triglyceride comprising independently selected saturated or unsaturated, branched or unbranched, substituted or unsubstituted $C_6$-$C_{24}$ fatty acids; a saturated or unsaturated, branched or unbranched $C_5$-$C_{24}$ aryl; a hydrophobic caged oligomeric or polymeric substance; or saturated or unsaturated, branched or unbranched, substituted or unsubstituted hydrophobic polymer; or any combination thereof. Suitably the alkyl hydrophobe may be selected decane or hexadecane. Exemplary caged oligomeric or polymeric substances include polyoctahedral silsesquioxanes (POSS) having substituents independently selected from hydrogen, a saturated or unsaturated, branched or unbranched, substituted or unsubstituted $C_1$-$C_{24}$ alkyl, or a saturated or unsaturated, branched or unbranched $C_5$-$C_{24}$ aryl.

The surfactant may be selected to control the resulting particle size of the templated microgel. The surfactant may be selected from an ionic surfactant, such as an anionic surfactant or a neutral surfactant. Suitably, ionic surfactants may include a saturated or unsaturated, branched or unbranched, substituted or unsubstituted $C_6$-$C_{24}$ alkylsulfate or $C_6$-$C_{24}$ arylsulfate; a saturated or unsaturated, branched or unbranched, substituted or unsubstituted $C_6$-$C_{24}$ alkylsulfonate or $C_6$-$C_{24}$ arylsulfonate; a saturated or unsaturated, branched or unbranched, substituted or unsubstituted $C_6$-$C_{24}$ alkylcarboxylate or $C_6$-$C_{24}$ arylcarboxylate; a saturated or unsaturated, branched or unbranched, substituted or unsubstituted $C_6$-$C_{24}$ alkylphosphate or $C_6$-$C_{24}$ arylphosphate; a saturated or unsaturated, branched or unbranched, substituted or unsubstituted quaternary $C_6$-$C_{24}$ alkylamine or quaternary $C_6$-$C_{24}$ arylamine. Suitably the ionic surfactant may be selected from sodium dodecyl sulfate, sodium stearate, or decyltrimethylammonium chloride. Suitably, neutral surfactants may include sorbitan monoesters, such as Span 20, Span 40, Span 60, Span 80, Span 83, Span 85, or Span 120, or polyethoxylated sorbitan monoester, such as Tween 20, Tween 40, Tween 60, Tween 65, or Tween 80.

Smaller particle size will increase the apparent proficiency of glycoside-hydrolyzing microgels through increased number of particles with increased total number of accessible catalytic sites. To create such microgels using miniemulsion polymerizations, the droplets must be stabilized against coalescence and diffusional instability (Ostwald ripening). [Reimers 1996] The stabilization against coalescence is influenced by the amount and nature of the added surfactant system. Diffusional stability of droplets in miniemulsions will be achieved by addition of a very small quantity of a hydrophobe. Hexadecane is one of the most active hydrophobes known in this regard and will be used without further alteration. [Landfester 2006] The frequently used anionic surfactant, SDS allowed the preparation of efficient catalytic microgels.

In miniemulsion polymerization, the particle size is linearly dependent on the amount and nature of surfactants used during microgel synthesis. In short, while the droplet size adjusts rapidly during ultrasonication to approach a pseudo-steady state, it does not change during polymerization afterward because of constant fusion and fission processes in hydrophobe-stabilized droplets. [Landfester 1999a] The droplet surfaces are typically incompletely covered with surfactant molecules, and micelle formation does not occur in the continuous phase of miniemulsions. Thus, for a given monomer mixture in a constant amount of aqueous layer, the size of the later microgel particle is directly dependent on the quality of the prepared miniemulsions and precisely controlled by the type and amount of surfactant. The size of the microgels is not influenced by the progress of a polymerization itself. Instead, the employed hydrophobic agents prevent or slow down premature Ostwald ripening of generated droplets in the miniemulsion after ultrasonication and allow their polymerization as is. [Landfester 2006] The equality of droplet pressure makes such systems insensitive against net mass exchange by diffusion processes when a minimum molar ratio of hydrophobe to monomer of approximately 1 to 250 is maintained. Droplet growth of such critically-stabilized miniemulsions occurs on the timescale of hundreds of hours. [Kabalnov 1987]

Neutral surfactants lack of dissociation in water and possess the broadest range of properties achievable that depend on their hydrophilic-lipophilic balance (HLB values between 0 and 20). The HLB values of the emulsifiers are additive and therefore allow the formulation of surfactant blends that are designed towards the desired properties. [Griffin 1949] A mixture of surfactants can be used to tailor the HLB. For example, hydrophilic emulsifiers based on polyoxyethylene sorbitanes (TWEEN 20-80) may be mixed with hydrophobic emulsifiers based on fatty acid sorbitans (SPAN 20-80) to match the HLB value of the targeted pre-polymerization mixture prior to microgel synthesis. The HLB value of the microgel pre-polymerization mixture using chemically different emulsifier blends with that same combined HLB value to optimize the emulsifier toward our screening parameters, i.e. a minimized particle size and translucency of the overall miniemulsion. This strategy improves current efforts in biomimetic catalysis with macromolecular catalysts by avoiding a lengthy synthesis of one particular emulsifiers that may or may not be applicable to the target system; by allowing flexible and convenient adjustments to altered compositions of pre-polymerization mixtures; and by general applicability.

Exemplary HLB values provided in Table XX reflect mixtures of SPAN 80 (HLB=4.3) and TWEEN 80 (HLB=15). Because HLB values are additive, the HLB can be tailored by altering the ratio between the mixtures of SPAN80 and TWEEN80 as needed. For example, 50 w % SPAN 80 and 50 w % TWEEN 80 give a surfactant mixture with an HLB value of 9.65

The metal ion solution may comprise any suitable metal ion that allows for the complexation of the ligand and carbohydrate or carbohydrate derivative to allow for templating of the microgel. Suitably the metal ion comprises a Cu(II) ion, suitably the solution is aqueous copper(II) acetate.

The buffer may be selected to maintain an alkaline pH. Suitable buffers include, without limitation, MOPS, TED, HEPES, DIPSO, MOBS, acetamidoglycine, TAPSO, TEA, POPSO, HEPPSO, EPS, HEPPS, tricine, tris, glycinamide, glycylclycine, HEPBS, bicine, TAPS, AMPB, CHES, AMP, AMPSO, CAPSO, CAPS, CABS, or any combination thereof.

The method may also comprise sonicating a pre-polymerization mixture. Suitably the sonicated prepolymerization mixture comprises monoacrylate monomer, the crosslinking monomer, the ligand monomer, the metal ion solution, the hydrophobe, and the surfactant, thereby preparing the ultrasheered prepolymerization miniemulsion. Sonication of the prepolymerzation mixture may be performed with or without a template. In other words, the sonication may be performed with or without a carbohydrate or carbohydrate derivative component in the mixture.

The method may also comprise providing an initiator to initiate the polymerization reaction. The ultrasheered prepolymerization miniemulsion may be irradiated in the presence of the carbohydrate or the carbohydrate derivative and the initiator. Suitably the initiator comprises 2,2'-dimethoxy-2-acetophenone.

The method may further comprise dialyzing the carbohydrate-templated microgel. The microgel may be dialyzed with one or more liquids over one or more intervals. Suitably the liquid used for dialysis may be selected from water, an EDTANa2 solution, a CAPS solution, a SDS solution, a CAPS/SDS solution, an EDTA/SDS solution, or other suitable solution.

The method may further comprise providing a second metal ion solution and activating the material. The second metal ion solution may be the same as the first metal ion solution but need not be. Suitably the second metal ion solution is a copper acetate solution.

Methods of Using Templated Microgels

The templated microgels disclosed herein may be used in methods of hydrolyzing a glycosidic bond. The templated microgels are materials demonstrating high catalytic activity many orders of magnitude higher than a comparable reaction where the antimicrobial material is not present. The method for hydrolyzing a glycosidic bond may comprise contacting any of the antimicrobial materials described herein or any of the antimicrobial materials prepared by a method described herein with a substrate. The substrate suitably is a carbohydrate or a carbohydrate derivative. Suitably the carbohydrate is selected from disaccharides, trisaccharides, oligosaccharides, or polysaccharides where the monomeric saccharide units are bonded by at least one $\alpha(1\text{-}2)$, $\alpha(1\text{-}4)$, $\alpha(1\text{-}6)$, $\beta(1\text{-}4)$, or $\beta(1\text{-}6)$ glycosidic bonds, including any combination thereof. Suitably carbohydrate derivatives is selected from a glycoconjugate such as a glycoprotein, a glycopeptide, a peptidoglycan, a glycolipid, a glycoside, a lipopolysaccharide, or any combination thereof.

In some embodiments, the carbohydrate or carbohydrate derivative is a membrane-bound carbohydrate or an extracellular polymeric substance. Suitably the membrane-bound carbohydrate or extracellular polymeric substance is associated with a microbe. The microbe may be a prokaryote such as a Gram-positive, Gram-negative bacteria, or a biofilm forming microbe.

Another aspect of the invention is methods for inhibiting proliferation of or killing a microbe. As demonstrated in the Examples, the templated microgels have antimicrobial activity and antimicrobial materials comprising the templated microgels may be prepared. Methods for inhibiting proliferation of or killing a microbe comprise contacting the microbe with an antimicrobial composition comprising any of the templated microgels described herein or any of the antimicrobial materials prepared by a method described herein. The microbe may be a prokaryote such as a Gram-positive, Gram-negative bacteria, or a biofilm forming microbe.

Another aspect of the invention is methods for treating a microbial infection. As demonstrated in the Examples, the templated microgels have antimicrobial activity and pharmaceutical compositions comprising the templated microgels may be prepared. Pharmaceutical compositions comprise an effective amount of one or more compounds as disclosed herein; and one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a microbial proliferative disease, disorder, or condition such as a microbial infection.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the compositions disclosed herein. For example, a "subject in need of treatment" may include a subject having a microbial proliferative disease, disorder, or condition such as a microbial infection. Suitably, the microbial infection is a prokaryotic infection such as a Gram-positive bacterial infection, a Gram-negative bacterial infection, or a microbial infection having a biofilm associated therewith.

Another aspect of the invention is methods for preparing articles having lowered susceptibility to the formation of a biofilm thereon. Suitably the method comprises applying any of the compositions described herein to a surface of the article. Suitably, the article is a dressing, bandage, medical instrument, or medical device.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1: Crosslinked Microgels as Platform for Hydrolytic Catalysts

1. Introduction

Miniemulsions were derived by ultrasheering of solutions containing BA (3), ethylene glycol dimethacrylate (EGDMA; 5), and VBbpdpo ligand (1) or styrene (4) followed by photoinitiated free radical polymerization at ambient temperature or below. The obtained particles were characterized for their hydrodynamic diameter, turbidity, composition, morphology, and thermal stability using dynamic light scattering (DLS), UV/vis, IR and EDX spectroscopy, transmission electron microscopy (TEM) imaging, and thermogravimetric analysis. Data was obtained to correlate the crosslinking content of the microgels to their catalytic ability using the hydrolysis of 4-methylumbelliferyl β-D-galactopyranoside (6) as a model reaction.

2. Materials and Methods 2.1. Instrumentation.

Images of microgels were acquired using a JEM 1011 (JEOL) Transmission Electron Microscope at 100 kV equipped with AMI Image Capture Engine software, version 602. Thermal stability data were obtained using a thermogravimetric analyzer TGA Q50 (TA Instruments) version V20.13 build 39. Energy-dispersive X-ray spectroscopy (EDX) was performed using a Nova NanoLab system (FEI) consisting of a dual-beam workstation with a FEG Scanning Electron Microscope and a focused ion beam. The system is fitted with an in-lens SE and BSE detector, and a Bruker Xflash 5010 detector. IR spectra were acquired using an ATR-FTIR 8000 spectrophotometer (Shimadzu) equipped with Lab Solutions IR software, version 2.15. Elemental analyses were obtained from Atlantic Microlab, Atlanta, GA. DLS of microgel dispersions was observed using a DynaPro-99E photometer (Protein Solutions/Wyatt Technology) equipped with a DynaPro Diode Laser at 825.1 nm, a temperature controlled microsampler (Protein Solutions) and Dynamics V6 software (Protein Solutions) for data recording and analysis. UV/vis spectra of microgel dispersions were obtained on a Cary 50 UV/vis spectrometer (Varian) equipped with WinUV Analysis Suite software, version 3.0. Glycoside hydrolyses were observed on a FilterMax F5Multi-Mode Microplate Reader (Molecular Devices) equipped with SoftMax Pro 6 software version 6.3. MALDI mass spectrometry data were obtained in the statewide mass spectrometry facility at the University of Arkansas on an Ultraflex II MALDI-TOF mass spectrometer with an upper weight limit of 80 kDa. A Digital Sonifier (Branson) with flat cap was used for ultrasonication. A UV medium-pressure lamp TQ 150 (Heraeus Noblelight) with a current of 2.0 A, a voltage of 90 V, a radiation flux Φ of 47 W between 200 and 600 nm, and an outer diameter of 13.50 mm was used for free radical polymerization. Polymer aliquots were dried by lyophilization using a FreeZone 1 L benchtop freeze-dry system (Labconco) or by air-drying using an IKA Dry Block Heater (VWR). A Barnstead E-Pure ultrapure water purification system (ThermoScientific) was used to obtain nanopure water at a resistance of 18.2 MΩ.

2.2. Reagents and Materials.

Styrene (4), sodium dodecyl sulfate (SDS), and 4-methylumbelliferone (7) were purchased from TCI America; EGDMA (5) from Alfa Aesar; BA (3) and neutral aluminum oxide from Acros Organics; decane, N-cyclohexyl-3-aminopropanesulfonic acid (CAPS), 2,2'-dimethoxy-2-phenylacetophenone, copper(II) acetate monohydrate, sodium hydroxide, pyrocatechol, and D galactose from Sigma-Aldrich; and 4-methylumbelliferyl β-D-galactopyranoside (6) from Carbosynth US. All monomers were purified by filtration over alumina immediately prior to use. All other chemicals were used as received. The polymerizable ligand N,N'-bis((3-(4-vinylbenzyloxy)-2-pyridylmethyl)-1,3-diaminopropan-2-ol (VBbpdpo, 1) [Striegler 2011] and the low molecular weight complex $Cu_2$bpdpo (2) [Striegler et al., J. Am. Chem. Soc. 2003, 125 (38), 11518-11524] were synthesized as described.

All pH values were measured after three-point calibration using a Φ 250 pH meter (Beckman) equipped with a refillable combination pH electrode (ROSS Orion). The electrode had a 165 mm long epoxy body and a 95 mm long semimicro tip with a diameter of 8 mm. Spectra/Por membranes (Spectrum Laboratories) with a molecular weight cutoff (MWCO) of 15000 were used for dialysis. The membranes were soaked in nanopure water for at least 30 min prior to use. Bottle-top filters (Nalgene) with 500 mL volume, 0.22 µm pore size, and poly(ether sulfone) (PES) membrane were used for filtration of aqueous buffer and SDS solutions. Formvar-coated Cu grids (Ted Pella) Type-A at 300 mesh with an approximate grid hole size of 63 µm were used for TEM imaging. A two-sided Hellma QS semimicro quartz cuvette with a 10 mm path length and 1400 µL volume was used for UV/vis studies. Disposable cuvettes (BrandTech) with four optically clear sides and a 10 mm light path were used for DLS experiments. Clear bottom 96-well black polystyrene microplates (Greiner Bio-One) were used for fluorescence assays. Heat-resistant polyester films (VWR) were used as 96-well plate adhesives.

2.3. Synthesis of Microgels.

2.3.1. Solutions of Aqueous Buffers and Other Reagents for Microgel Synthesis. CAPS/SDS Buffer. Typically, 0.221 g (1.00 mmol) of CAPS was dissolved in nanopure water. The resulting solution was titrated with aqueous sodium hydroxide solution to pH 10.08 at 23° C. and adjusted to a volume of 200 mL translating into a buffer solution with a pH of 10.50 at 0° C. Then, SDS (3.0000 g, 10.403 mmol) was dissolved in a portion of this CAPS buffer solution to yield 200.00 g of an aqueous SDS/CAPS buffer solution that is approximately 5 mM in CAPS and 52 mM in SDS. The buffer solution was stored at ambient temperature until use.

Galactose Stock Solution. Typically, 0.3147 g (1.747 mmol) of galactose were dissolved in 5 mL of nanopure water. The 350 mM stock solution was kept at ambient temperature and used in 250 µL aliquots.

Ethylene Glycol Stock Solution. Typically, 0.1118 g (1.801 mmol) of ethylene glycol were dissolved in 5 mL of nanopure water. The 360 mM stock solution was kept at ambient temperature and used in 250 µL aliquots.

Copper(II) Acetate Stock Solution. Typically, 0.1747 g (875.0 µmol) of copper(II) acetate were dissolved in 5 mL of nanopure water. The 175 mM stock solution was kept at ambient temperature and used in 100 µL aliquots.

Initiator Stock Solution. Typically, 0.2189 g (854.1 µmol) of 2,2'-dimethoxy-2-acetophenone were dissolved in 900 µL of methanol immediately prior to use. A 200 µL aliquot of this stock solution was used to initiate the polymerization and any remainder of the solution was discarded.

Pyrocatechol Solution. Typically, 0.0839 g (0.7620 mmol) of pyrocatechol were dissolved in 2 mL of nanopure water. The resulting stock solution was used in 10 µL aliquots.

Sonication of Solutions. Ultrasheering of prepolymerization miniemulsions was achieved by sonication at 0° C. using an amplitude of 40% over 2 min in pulse mode (5 s on and 2 s off).

2.3.2. General Procedure for the Preparation of Microgels Containing Styrene. Monomer Composition. All polymers contain a combined monomer amount of 1.75 mmol and differ in the respective EGDMA and BA amounts corresponding to 5, 10, 25, 40, 50, 60, and 80 mol % of crosslinker; that is, EGDMA (0.087-1.400 mmol) and BA (1.663-0.350 mmol). The styrene amount was kept constant at 1 mol % of the overall monomer content, that is, 0.0175 mmol.

UV-Initiated Free Radical Polymerization. In a typical experiment, the respective monomer mixture was added to 9.6 g of CAPS/SDS buffer solution at ambient temperature and stirred after addition of 80 mg of decane, 250 µL of the galactose stock solution, and 100 µL of the copper acetate stock solution. After 5 h, the prepolymerization mixture was cooled in an ice bath and sonicated in the cold. The resulting miniemulsion was treated with 200 µL of the initiator solution in the cold and immediately placed under UV light. All reaction mixtures were stirred and kept in an ice-bath to ensure a temperature of 3° C. or below during the polymerization over 90 min. Additionally, microgels were prepared in a similar fashion using 250 µL of the ethylene glycol stock solution in place of the galactose stock solution and used for control experiments.

Gravimetric Analysis. To follow the proceedings of the polymerization reaction, 100 µL aliquots of the reaction mixture were taken after 2, 5, 10, 20, 30, 45, 60, 75, and 90 min and treated with 10 µL of the pyrocatechol stock solution. The resulting aliquots were air-dried at 60° C. for at least 48 h prior to gravimetric analysis. The progress of the reaction (P) was calculated using eq 1

$$P\ [\%] = m_{solid}/(m_m + m_{surfactant}) \times m_{all}/m_{aliquot} \times 100 \quad (eq\ 1)$$

where $m_{solid}$ is the mass of remaining solid obtained after drying corrected for the weight of galactose and buffer solution, $m_m$ is the mass of the combined monomer weights, $m_{all}$ is the mass of reaction mixture, and $m_{aliquot}$ is the mass of each aliquot taken.

Likewise, polymers from miniemulsions in 2.4, 3.6, 4.8, and 7.2 g of SDS/CAPS buffer were prepared using the same procedure. Each polymerization was carried out in duplicate and the reported values are averages of at least two independent data sets. Control polymers were prepared in absence of Cu(II) acetate and galactose in a similar fashion.

2.3.3. General Procedure for the Preparation of Microgels Containing VBbpdpo Ligand. VBbpdpo Ligand Stock Solution. Typically, 0.1352 g (252.1 µmol) of VBbpdpo (1) were dissolved in 3.1664 g of DMSO, and the resulting solution was used in 0.1146 g portions that correspond to 8.75 µmol of ligand.

Monomer Mixtures. All polymers contain a combined monomer amount of 1.75 mmol and differ in the respective EGDMA and BA amounts as specified above. Instead of styrene, a suitable increment of the ligand stock solution was added to each polymerization mixture to keep the ligand amount constant at 0.05 mol % of the overall monomer content, that is, 8.75 µmol.

UV-Initiated Free Radical Polymerization. The prepolymerization mixtures were treated as described for microgels containing styrene, but exposed to UV light for 60 min only.

2.4. Characterization of Microgels in Solution.

Sample Preparation. All samples were dialyzed and diluted with filtered 52 mM aqueous SDS solution in volumetric flasks. Typically, a 1000 µL aliquot of the synthesized microgel dispersion was dialyzed against 20 mL SDS solution for 10 h in 2 h intervals 5× each. A 200 µL aliquot of the purified microgel dispersions was then diluted 1250-fold by serial dilution of corresponding aliquots for DLS experiments and 250-fold for UV/vis experiments.

Dynamic Light Scattering. The scattered light was detected at a 90° angle to the incident beam at 20±1° C. The fluctuation of the measured scattering intensity was transformed into the hydrodynamic diameter of the samples using the method of cumulants for a monomodal system, as implemented in the Dynamics V6 software. [Koppel et al. J. Chem. Phys. 1972, 57 (11), 4814-4820; Frisken, B. J. et al. Appl. Opt. 2001, 40 (24), 4087-4091] The mean hydrodynamic diameter $D_h$ and the polymer dispersity D were derived as an average of 10 scans with 10 acquisitions over 10 s each. The obtained mean hydrodynamic diameter $D_h$ was then plotted against the crosslinking content of the respective microgel.

UV/Vis Spectroscopy. The absorbance of the microgel samples was recorded between 300 and 800 nm at 37.0±0.1° C. The resulting data are given as an accumulated average of 3 scans and corrected for the absorbance of the buffer solution.

2.5. Characterization of Microgels in the Solid State.

Sample Preparation. Typically, a 1000 µL aliquot of the synthesized microgel dispersion was dialyzed against 40 mL of 0.2 mM disodium ethylenediamine tetraacetate (EDTANa$_2$) solution (5× each) and 40 mL of nanopure water (5× each) for a total of 10 h in 2 h intervals. The dialyzed solutions of the microgels were freeze-dried for 36 h, and the resulting solid was used for further analysis unless stated otherwise.

IR Spectroscopy. Absorbance spectra were acquired in % transmittance mode using freeze-dried microgels at ambient temperature between 500 and 4000 cm$^{-1}$ with a resolution of 2 cm$^{-1}$. The data are given as an average of three accumulated scans.

Energy-Dispersive X-ray Spectroscopy (EDX). All experiments were performed at 15 kV accelerating voltage. Freeze-dried microgel samples were fixed on the specimen holder using double-sided carbon tape and sputtered with gold to increase conductivity.

Thermogravimetric Analysis (TGA). The thermal stability of freezedried microgels was determined by heating of samples from 20 to 800° C. at a rate of 10° C./min in a nitrogen atmosphere with a flow rate of 20 mL/min. The polymers were equilibrated at 70° C. for 60 min.

Elemental Analysis. The composition of polymers derived from 5, 25, 40, 60, and 80 mol % EGDMA prepared in the presence of galactose or ethylene glycol was determined by combustion analysis; Anal. Calcd for $^L P_{gal}$ (5% EGDMA): C, 65.38; H, 9.23; N, 0.21. Found: C, 65.27; H, 9.08; N, 0.23; $^L P_{gal}$ 1 (25% EGDMA): C, 64.07; H, 8.63, N, 0.19. Found: C, 63.85; H, 8.48; N, 0.13; Anal. Calcd for $^L P_{gal}$ (40% EGDMA): C, 63.24; H, 8.25; N, 0.18. Found: C, 62.97; H, 8.12; N, 0.13; Anal. Calcd for $^L P_{gal}$ (60% EGDMA): C, 62.28; H, 7.81; N, 0.16. Found: C, 62.22; H, 7.70; N, 0.14, Anal. Calcd for $^L P_{gal}$ (80% EGDMA): C, 61.47; H, 7.45; N, 0.15. Found: C, 60.75; H, 7.31; N, 0.20; Anal. Calcd for $^L P_{eg}$ (60% EGDMA): C, 62.28; H, 7.81; N, 0.16. Found: C, 61.35; H, 7.72; N, 0.14.

2.6. Chemical Stability of Microgels in Solution.

Sample and Buffer Preparation. Typically, 200 mL of 50 mM aqueous buffer solutions were prepared by standard procedures at ambient temperature. Then, SDS (3.0000 g, 10.403 mmol) was dissolved in a portion of this buffer solution to yield 200.00 g of an aqueous SDS/buffer solution that is approximately 50 mM in buffering agent and 52 mM in SDS. The aqueous buffer solution was stored at ambient temperature until use; For pH 1, a 0.1 M aqueous hydrochloride solution was used; at pH 3, formate; pH 5, acetate; pH 7, 4-(2-hydroxyethyl)-1-piperazineethanesulfonic acid; pH 9, [tris(hydroxymethyl)-methylamino]-propanesulfonic acid; pH 11, CAPS; and at pH 13, a 0.1 M aqueous sodium hydroxide solution.

Stability Assay. Typically, 200 μL aliquots of the aqueous microgel dispersions with 5, 25, 40, 60, and 80 mol % of crosslinking EGDMA were diluted into 10 mL with aqueous SDS solution. A 1000 μL aliquot of the resulting solutions each was then dialyzed against 70 mL of the respective aqueous buffer solution over 24 h in 4, 10, and 10 h intervals, followed by dialysis against 70 mL of aqueous SDS solution for an additional 12 h. The purified microgels were diluted into 5 mL solutions with aqueous SDS solution. Prior to analysis, 1000 μL aliquots of these microgel dispersions were further diluted with 2000 μL of aqueous SDS solution, yielding an overall 750-fold dilution of the original samples. Aliquots of the diluted microgel samples were then analyzed by DLS assays, as described above (see section 2.4)

2.7. Microgel Imaging via Transmission Electron Microscopy.

SDS Stock Solution. Typically, 6.00 g (20.8 mmol) of SDS were dissolved in 1000 mL of nanopure water, yielding a 20 mM aqueous SDS solution. Aliquots of the solution were used for dialysis and dilution of microgel dispersions as described.

Styrene-Containing Polymers. In a typical procedure, 500 μL of the polymer solution were diluted with 500 μL of SDS solution. The resulting solution was sonicated for 10 min at 40% amplitude in pulse mode (5 s on, 5 s off) under cooling in an ice bath using a tapered microtip and then dialyzed against 60 mL of the same aqueous SDS stock solution six times in 2 h time intervals each. One drop of the resulting solution was put on a Cu grid, air-dried at ambient temperature for 48 h prior, and used for imaging without any further preparation.

Ligand-Containing Polymers. In a typical procedure, 500 μL of the polymer solution were dialyzed in 2 h time intervals 5 times each, and diluted with 500 μL SDS stock solution. One drop of the resulting solution was put a Cu grid, air-dried at ambient temperature for 48 h prior and used for imaging without any further preparation.

TEM Imaging. Images of the dried microgel samples were obtained at 100 kV using 25000- to 200000-fold magnification.

2.8. Evaluation of Microgels as Catalysts.

General Remarks. A 50 mM aqueous CAPS buffer solution corresponding to pH 10.50 at 37° C. was prepared using standard procedures and stored at ambient temperature until use. All experiments were performed in a 96-well plate format at 37.0±0.1° C. All microgel dispersions are purified by dialysis, and the catalysts are activated by appropriate amounts of aqueous copper(II) acetate solutions as needed.

2.8.1. Microgel Preparation for Kinetic Evaluation. EDTANa$_2$/SDS Solution for Dialysis. In a typical experiment, 8.25 mg (22.2 μmol) EDTANa$_2$ and 1.50 g (5.20 mmol) of SDS were dissolved in 100 mL of nanopure water. The resulting solution was used in 20 mL aliquots.

EDTANa$_2$ Solution for Dialysis. In a typical experiment, 0.0762 g (0.205 mmol) of EDTANa$_2$ were dissolved in 1000 mL of nanopure water and used in 200 mL aliquots.

SDS Solution for Dialysis. In a typical experiment, 3.00 g (10.4 mmol) of SDS were dissolved in 100 mL of nanopure water. The resulting solution was used in 20 mL aliquots.

CAPS/SDS Solution for Dialysis. In a typical experiment, 200 mL of a 50 mM CAPS buffer solution was prepared by standard procedures at ambient temperature at pH 10.63. Then, 3.00 g (10.4 mmol) of SDS were dissolved in the buffer and the overall weight of the resulting solution was kept at 200.00 g. The resulting solution was used in 20 mL aliquots.

Microgel Dialysis Prior to Elemental Analysis. In a typical experiment, a 1000 μL aliquot of five different microgel dispersions were purified by dialysis against 200 mL of aqueous EDTANa2 solution and 200 mL of water in 2 h intervals 5x each. The purified microgel dispersions were freeze-dried, and their resulting weight was recorded. The immobilized ligand content was then calculated from the overall N-content of the sample, as determined by elemental analysis. [Streigler 2012; Streigler 2011]

Microgel Dialysis Prior to Kinetic Evaluation. In a typical experiment, 500 μL of a microgel dispersion were purified by dialysis using a sequence of aqueous EDTA/SDS, SDS, and CAPS/SDS solutions in 2 h intervals 5x each. The purified microgel dispersion was diluted with CAPS/SDS buffer solution to about 4.5 mL and followed by catalyst activation.

Catalyst Activation. A 25-40 μL aliquot of an aqueous copper(II) acetate stock solution (18.46 mg in 5 mL of water) was added to the microgel dispersion purified by dialysis. The volumes of the aliquots reflect the metal ion content calculated for complete saturation of the immobilized ligand for each individual microgel. The resulting microgel dispersions were further diluted with aqueous CAPS/SDS solution to 5 mL of overall solution and stored at ambient temperature prior to use. All solutions were used within 7 days or discarded. For control experiments, a metal-ion free, nonactivated polymer $^L$P$_{gal}$ was prepared in a similar fashion; however, the addition of aqueous copper (II) acetate solution was substituted by corresponding amounts of buffer solution.

2.8.2. Apparent Extinction Coefficients $\varepsilon_{app}$. Stock Solution of 4-Methylumbelliferone (7). In a typical experiment, 6.38 mg (36.2 μmol) of 4-methylumbelliferone (7) were dissolved in 500 μL of DMSO and diluted into 5 mL with aqueous buffer solution. By serial dilution, a 0.3 μM stock solution of 7 was prepared immediately prior to use. Three independent stock solutions were made this way.

Assay. A selected constant aliquot of the activated microgel dispersion (0, 10, 15, 20, 25, 30, 35, or 40 μL) was added to aliquots (0-160 μL) of the stock solution of 7, followed by addition of aqueous buffer solution to keep the nominal volume of the resulting solutions at 200 μL. The resulting solutions were prepared in triplicate from the independent stock solutions of 7 and equilibrated at 37° C. for 30 min. The fluorescence of 7 was read at $\lambda_{ex}$=360 nm and $\lambda_{em}$=465 nm.

Data Analysis. The fluorescence was plotted over the molar substrate concentration. The apparent extinction coefficients $\varepsilon_{app}$ were then determined from the slope of the linear fit of the plotted data and given as an average of three independent experiments for each catalyst solution at a specified volume.

2.8.3. Determination of a Suitable Catalyst Concentration Range. Substrate Stock Solution. Typically, 10.34 mg (30.58 μmol) of 4-methylumbelliferyl β-D-galactopyranoside (6) were dissolved in 1000 μL of DMSO and diluted to 10 mL with 50 mM aqueous CAPS buffer solution, yielding a 3.4 mM substrate stock solution. As the glycoside precipitates at ambient temperature over time, the resulting solution was kept above 50° C. and prepared immediately prior to use.

Stock Solution of Catalyst Cu2bpdpo (2). Typically, 5.91 mg (9.00 μmol) of Cu2bpdpo (2) was dissolved in 5 mL of buffer solution. Then, a 500 μL aliquot was further diluted into 10 mL, yielding a use.

Stock Solution of Microgel Catalysts. Typically, the activated microgel dispersions were prepared as described above and used without any further modification.

Assay. In a 96-well plate, 0-40 μL aliquots of the respective catalyst stock solutions were added in to a constant 100 μL aliquot of the substrate stock solution followed by corresponding aliquots of the buffer solution to keep the nominal total volume at 200 μL in each well. The substrate hydrolysis was followed at 37° C. by monitoring the formation of 4-methylumbelliferone (7) using fluorescence spectroscopy ($\lambda_{ex}$=360 nm; $\lambda_{em}$=465 nm) over 8 h. All experiments were performed in triplicate.

Data Analysis. The collected fluorescence data were plotted over time, and a linear fit was applied to the data collected between 140 and 480 min. The calculated rates of the reaction were then corrected by the corresponding apparent extinction coefficient and catalyst amount, averaged from at least two independent experiments and plotted over the catalyst concentration. A linear fit was applied to the linear range of the data to visualize the concentration range, in which the catalyst concentration depends linearly on the reaction rate; for microgel $^{Cu2L}P_{gal}$: a=4.3×10-10; b=3.2× 10-9; $R^2$=0.999; 6 at 3.4 mM; catalyst concentration range: 0-7 μM; for Cu$_2$bpdpo (2): y=a+bx, a=4.5×10-10, b=5.4× 10-9, $R^2$=0.998; 6 at 3.1 mM; catalyst concentration range: 0-12 μM.

2.8.4. Catalytic Glycoside Hydrolysis. CAPS Buffer Solution for Catalysis. In a typical experiment, 100 mL of a 50 mM CAPS buffer solution were prepared by standard procedures at ambient temperature, accounting for temperature differences for the intended use at pH 10.50 and 37° C.

Substrate Stock Solution. Typically, 5.68 mg (16.8 μmol) of 4-methylumbelliferyl β-D-galactopyranoside (6) were dissolved in 500 μL of DMSO and diluted to 5 mL with 50 mM aqueous CAPS buffer solution, yielding a 3.4 mM substrate stock solution. As the glycoside precipitates in this concentration from aqueous solutions at ambient temperature, the resulting solution was kept above 50° C. until use.

Catalyst Stock Solutions. The microgel dispersions were used as described above. The stock solutions of Cu2bpdpo (2) were prepared by dissolving 5.53 mg (8.42 μmol) in 5 mL of 50 mM CAPS buffer solution.

Kinetic Assay. In a typical experiment, 20 μL of an activated microgel dispersion were added to aliquots of the glycoside stock solution (0-100 μL) and corresponding amounts of buffer solution, keeping the nominal volume of the resulting solutions at 200 μL. The hydrolysis of 6 was monitored over 8 h by following the formation of 4-methylumbelliferone (7; $\lambda_{ex}$=360 nm; $\lambda_{em}$=465 nm). The product formation was read in 20 min intervals after orbital shaking of the solutions over 5 s each. All experiments were performed in duplicate or triplicate.

Data Analysis. The collected fluorescence intensity was plotted over time, and a linear fit applied to the data collected between 140 and 480 min. The calculated rates of the reaction were then corrected by the corresponding apparent extinction coefficient and catalyst amount, averaged from two independent experiments, and plotted over the molar substrate concentration. Nonlinear regression of the resulting hyperbolic data yielded the rate constant $k_{cat}$ and the apparent substrate affinity KM. The rate constant of the uncatalyzed reaction $k_{non}$ was determined by applying a linear fit to the corrected rates of the collected data obtained in absence of catalyst. Data obtained in the presence of metal-ion free control polymer $^{L}P_{gal}$ and from control polymer $^{Cu2L}P_{EG}$ were treated likewise to estimate their catalytic efficiency.

3. Results and Discussion 3.1. Protocol Development for Polymerization of Miniemulsions at Low Temperature.

For the development of a protocol suitable for the immobilization of pentadentate ligand VBbpdpo (1) at ambient temperature or below, mixtures of ligand 1, BA (3), EGDMA (5), and decane were stirred in CAPS/SDS buffer for 4-5 h (Chart 1).

Chart 1. Structures of the VBbpdpo Ligand and Other Reagents

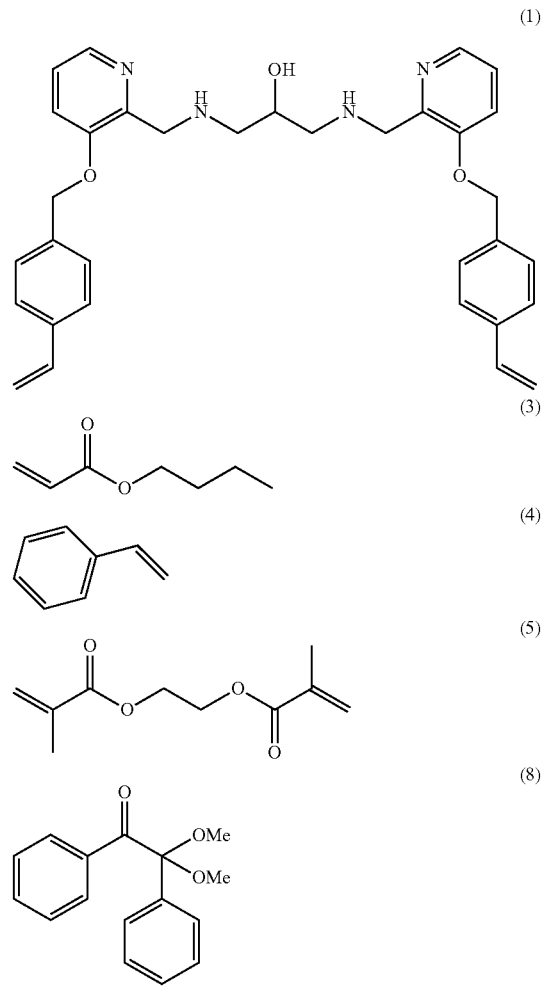

Figure 2:
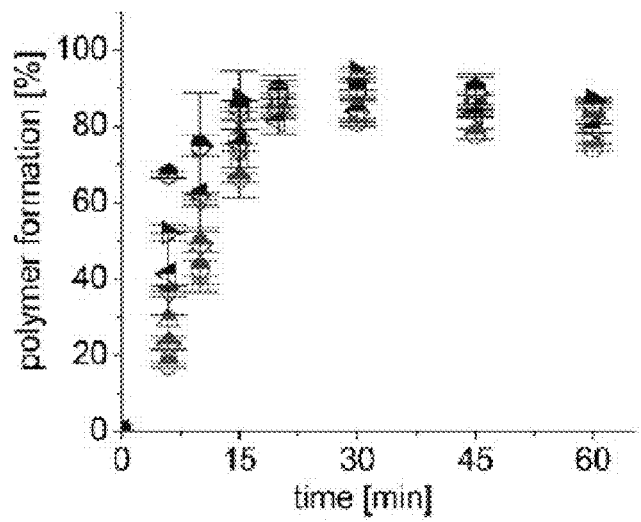
FIG. 2 shows progress of the photoinitiated free radical polymerization of mini-emulsions containing 0 (yellow square), 0.25 (red circle), 0.50 (red triangle), 0.75 (purple down-pointing triangle), 1.00 (blue tilted square), 1.25 (black left-pointing triangle), 1.50 (blue right-pointing triangle), and 1.75 (purple hexagon) mmol of EGDMA; corresponding amounts of BA, in the presence of 2 mol % styrene and 5 mol % photoinitiator in 5 mM aqueous CAPS buffer solution at pH 10.50 and ambient temperature (20-22° C.)

Miniemulsions thereof were then prepared by ultrasheering of the resulting solution. Decane was used as a hydrophobe to suppress the thermodynamic instability of the resulting miniemulsions caused by Ostwald ripening and coalescence. [Antonietti, M. et al. Prog. Polym. Sci. 2002, 27 (4), 689-757] Addition of 2,2-dimethoxy-2-phenylacetophenone (8) in methanol initiated the free radical polymerization under UV light at ambient temperature. [Bryant, S. J. et al. J. Biomater. Sci., Polym. Ed. 2000, 11 (5), 439-457.] As VBbpdpo 1 requires a multistep synthesis and labor-intensive purifications, equimolar amounts of styrene (4) were used for the optimization of the polymerization protocol in early stages of this study. Styrene is commercially available and represents the polymerizable end groups of the VBbpdpo ligand (1). Gravimetric analyses of reaction aliquots were used to follow the proceedings of the polymerization reaction and demonstrated satisfactory conversion of BA (1.75-0 mmol) in the presence of EGDMA (0-1.75 mmol), and styrene (≤2 mol %) using 5 mol % photoinitiator in 5 mM SDS/CAPS buffer at pH 10.50 and ambient temperature (FIG. 2).

Figure 3A:
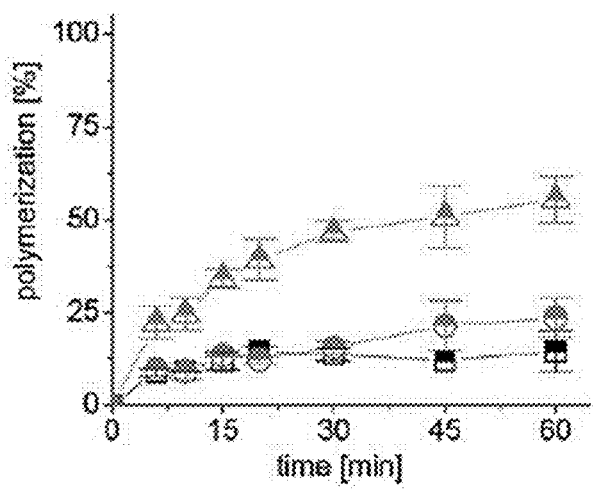
FIGS. 3A and 3B shows progress of the photoinitiated free radical polymerization using (FIG. 3A) 5 mol % and (FIG. 3B) 10 mol % of photoinitiator to convert miniemulsions derived from monomer mixtures containing 14 mol % (black square), 28 mol % (red circle), and 42 mol % (green triangle) of EGDMA; corresponding amounts of BA and 2 mol % of styrene in 5 mM aqueous CAPS buffer solution at pH 10.50 and 0° C.

However, when repeating the reaction under ice-cooling, incomplete monomer conversion for miniemulsions with low EDGMA content (≤50 mol %) and extended reaction times to reach maximal monomer conversion were noted (FIG. 3A). We consequently increased the concentration of the photo initiator from 5 to 10 mol % for all subsequent experiments.

Figure 3B:
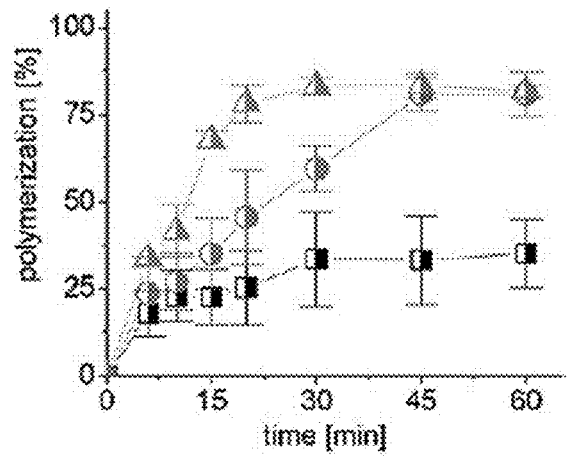

While the polymerization then levels out at around 80% monomer conversion for microgels derived from EGDMA at 28 or 42 mol %, the use of 14 mol % of crosslinking agent remains insufficient and still leads to incomplete monomer conversions (FIG. 3B).

Figure 4:
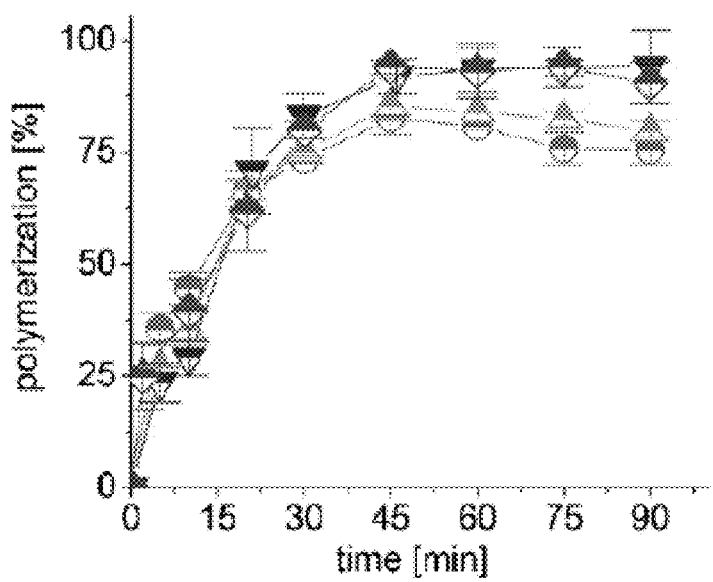
FIG. 4 shows monomer conversion over time at 0° C. for mini-emulsions derived from 60 mol % EGDMA, 40 mol % BA and 1 mol % styrene in (a) 4.8 g (green circle), (b) 7.2 g (yellow triangle), (c) 9.6 g (red tilted square), and (d) 12.0 g (wine red down-pointing triangle) of SDS/CAPS buffer solution.
Figure 5A:
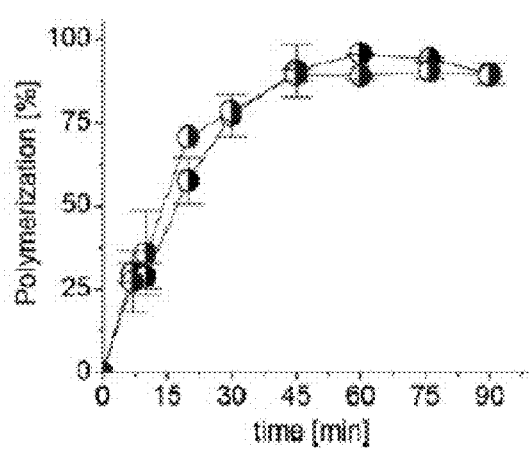
FIGS. 5A-5B show monomer conversion over time in 9.6 g of SDS/CAPS buffer solution at pH 10.50 and 0° C. for miniemulsions derived from (FIG. 5A) 60 mol % EGDMA, 40 mol % BA and 1 mol % styrene in presence (blue circle) and absence (black circle) of Cu(II) ions and galactose.

The polymerization conditions were then further optimized for each EGDMA concentration by an increase in the amount of SDS/CAPS buffer solution from the previously used 4.8 g to 9.6 g per reaction, thereby increasing the ratio of surfactant to monomer. The number of particles and their size, as well as the degree and rate of polymerization are directly dependent on the concentration of the surfactant. [Capek, I. et al. Makromol. Chem. 1987, 188 (7), 1723-1733; L. Dimonie, V.; Sudol, D.; El-Aasser, M. et al. Rev Chim (Bucureti) 2008, 59, 1218-1221] Employing the outlined adjustments, the monomer conversion reaches over 93% at about 60 min for any crosslinking content of the miniemulsions. As a representative example, the monomer conversions for miniemulsions derived from 60 mol % EGDMA at different dilutions are depicted (FIG. 4). The optimized dilution conditions were consequently used as a standard for any subsequent microgel preparation. In addition, the reaction time of the microgel synthesis is substantially shortened from previous 180 to less than 75 min.42 As the preparation of microgels via free radical polymerization may be hampered in the presence of paramagnetic Cu(II) ions, a previously developed masking protocol using excess of coordinating anions was additionally employed. [Striegler 2012] As expected, the monomer conversion was not notably influenced by Cu(II) ions in the presence of deprotonated galactose in alkaline solution and equals the polymerization proceedings in absence of metal ions (FIG. 5A).

Figure 5B:
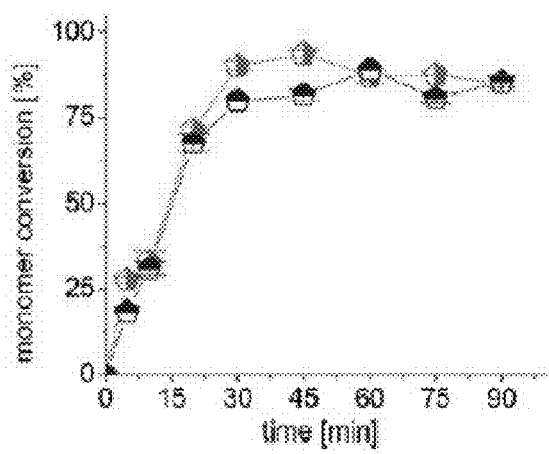

The developed protocol shows also comparable polymerization proceedings for the synthesis of microgels $^SP$ and $^LP$ with equal crosslinking content after exchange of 4 by molar equivalents of ligand 1 (FIG. 5B). With a successful polymerization protocol on hand, a series of microgels containing polymerizable ligand VBbpdpo (1) at crosslinking amounts between 5 and 80 mol % was prepared, their physical properties characterized and catalytic activity established. All styrene-containing microgels $^SP$ were prepared likewise, but contain the molar equivalent of 4 instead of 1.19 All polymers were prepared in the presence of Cu(II) ions and excess galactose. For control experiments, polymers using ethylene glycol instead of galactose were synthesized under otherwise identical conditions.

3.2. Microgel Characterization in Solution.

Gravimetric analyses of both polymer series LP and SP with crosslinking content between 5 and 80 mol % disclosed similar monomer conversion during the polymerization reaction over time (see above). However, the resulting particles may still differ in their mean hydrodynamic diameter, polydispersity, and apparent turbidity, which all influence their intended use as catalysts. Consequently, all microgels were initially characterized in solution using DLS and UV-vis spectroscopy. Attempts to analyze the microgels by gel permeation chromatography were futile due to their high crosslinking content (≥5%).

Figure 6:
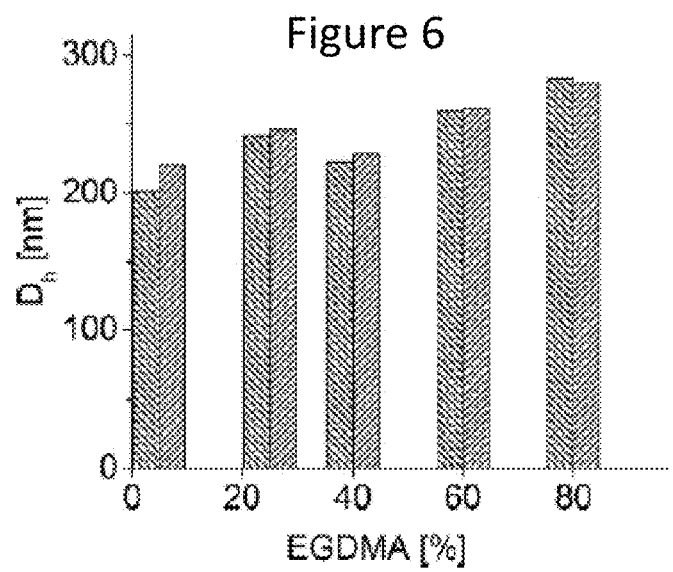
FIG. 6 shows mean hydrodynamic diameters ($D_h$) of microgels derived from ligand VBbpdpo (magenta; right) and styrene (blue; left) with crosslinking content between 5 and 80 mol %; T=20° C.

3.2.1. Microgel Characterization via Dynamic Light Scattering. The synthesized microgels were purified by dialysis prior to analysis using DLS. The mean hydrodynamic diameter ($D_h$) and the sample dispersity (D) were obtained after dilution of dialyzed microgels with aqueous SDS solution in order to eliminate concentration-dependent scattering effects. [Murphy, R. W. et al. J. Colloid Interface Sci. 2017, 505, 736-744] All ligand- and styrene-containing polymers show mean hydrodynamic diameters between 200 and 285 nm that are comparable at the same crosslinking content (FIG. 6). The substitution of ligand 1 by 4 during optimization of polymerization procedures in the early stages of the project is thus unlikely to have altered the composition, size, or swelling behavior of the resulting microgels. The dispersity of the microgels is narrow and ranges from 0.10 to 0.18. Ligand-containing microgels with a crosslinking content at 5 mol % display a mean hydrodynamic diameter of 210±10 nm, which is smaller than the corresponding value for polymers with 25% (245±5 nm) or 80% crosslinking content (280±2 nm). The particle size increases as a consequence of the increased crosslinking content of the matrix. At the same time, the increased matrix rigidity reduces their swelling capacity, which decreases the hydrodynamic diameter and rivals the particle enlargement caused by a higher crosslinking content. As a result of these competing phenomena, the microgels at 25 mol % crosslinking content are on average 15 nm larger than a microgel prepared at 40% crosslinking content and 35 nm larger than a microgel synthesized at 5 mol % of crosslinking EGDMA.

To assess the chemical stability, aliquots of styrenecontaining microgels with different crosslinking content were exposed to aqueous SDS/buffer solutions between pH 1 and 13 for 24 h each. The mean hydrodynamic diameter of the microgels remained constant for a given crosslinking content over the selected pH range. Related microgels were previously reported with comparable stability against particle hydrolysis by others. [Bhattacharya, S. et al. Small 2007, 3(4), 650-657]

Figure 7:
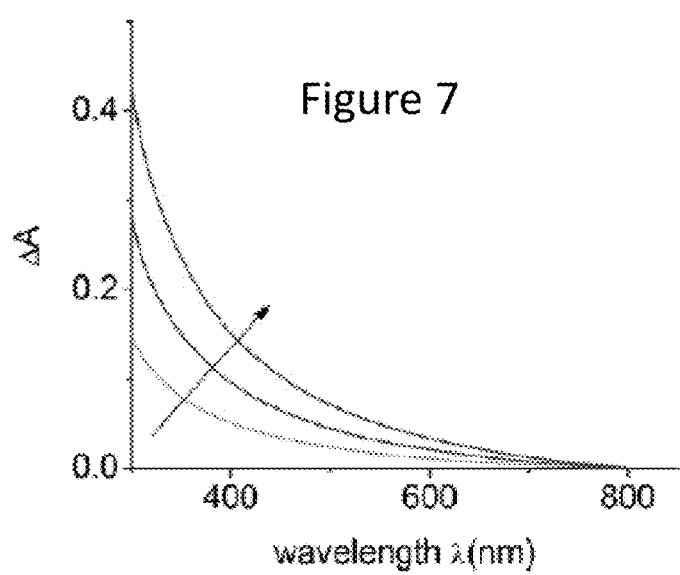
FIG. 7 shows absorbance of dispersed microgels in aqueous SDS solution containing 5 mol % (orange; bottom curve), 40 mol % (red; middle curve), and 60 mol % (olive; top curve) of EGDMA.

3.2.2. Microgel Characterization via UV/Vis Spectroscopy. Any turbidity of solutions derived from crosslinked microgels may hamper their later spectroscopic evaluation as catalysts when using UV/vis spectroscopy. Consequently, the absorbance of the dispersed microgels was determined between 300 and 800 nm relative to the aqueous SDS solution used as a solvent (FIG. 7).

Solutions of ligand-containing microgels and their styrene counterparts show near identical absorbance spectra in the selected wavelength range (data not shown) that increase relative to the crosslinking content of the dispersed particles. Similar observations were noted for related crosslinked microgels by others previously. [Kim, J. W. et al. Colloid Polym. Sci. 2000, 278 (6), 591-594; Al-Manasir, N. et al. J. Appl. Polym. Sci. 2009, 113 (3), 1916-1924; Xia, X.; Hu, Z. Langmuir 2004, 20 (6), 2094-2098] The results imply that the extinction coefficient for each solution containing microgel has to be determined to account for turbidity effects when using microgels as catalysts.

3.3. Characterization of Microgels in the Solid State.

The composition and morphology of the dispersed particles forming the microgels were characterized by IR and EDX spectroscopy and MALDI mass spectrometry. The thermal stability of the polymers was determined by thermal gravimetric analysis and the particle morphology was visualized by tunneling electron microscopy. Toward this end, the microgels were dialyzed against nanopure water to remove all traces of buffer and emulsifier and freeze-dried. Elemental analysis data confirmed incorporation of the VBbpdpo ligand with near quantitative yield based on analysis of the N-content, as described on different occasions before. [Striegler 2012; Striegler 2011; Gichinga, M. G. et al. Polymer 2010, 51(3), 606-615] Attempts to further characterize the N-content of microgels derived from VBbpdpo by EDX spectroscopy failed, indicating a N-content below the detection limit (i.e., ≤1 wt %). Analysis of samples by MALDI mass spectrometry indicated molar masses of the crosslinked microgels above 100 kDa that could not be further specified due to experimental limitations of the method.

Figure 8A:
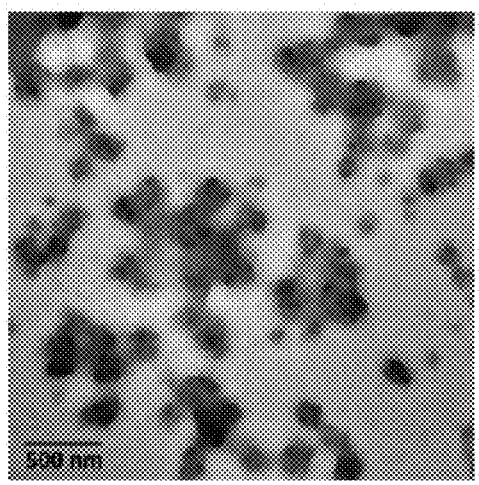
FIGS. 8A-8B show TEM images of freeze-dried microgel samples with 60 mol % crosslinking content derived from (FIG. 8A) VBbpdpo ligand and (FIG. 8B) styrene.
Figure 8B:
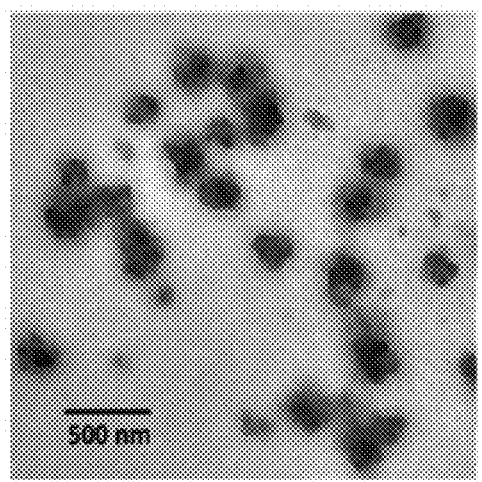

3.3.1. Particle Imaging. The morphology of the microgels in the solid state was visualized by tunneling electron microscopy. In the presence of emulsifier in a concentration used for material preparation, only blurry images with high background scattering were obtained. In the absence of emulsifier, particle agglomeration or precipitation was observed. A modified dialysis protocol to include SDS in reduced amounts eventually allowed imaging of samples with a crosslinking content of 60 mol % (FIGS. 8A and 8B).

Popcorn-like particles with a mean diameter of ~250 nm and visible deformation were detected. This particle deformation is ascribed to a high local crosslinking density and the resulting nonuniform swelling of the microgels during the nucleation step as already noted by others. [Lee, K.-C.; et al. Macromol. Res. 2007, 15(3), 244-255] As our microgels are synthesized for an intended use as homogeneous catalysts in aqueous solution, characterization of the particle size by DLS in water appears more appropriate than TEM imaging in the dry state. Further attempts to image other microgels in the solid state were thus not made. However, the mean diameters of the imaged microgels at 60% crosslinking are only slightly smaller than their mean hydrodynamic diameter in aqueous solution as determined via DLS analysis. This observation underscores again the reduced particle swelling ability of microgels with high crosslinking content in aqueous solution as discussed above and noted by others previously. [Martinez, V. S. et al. Chem. 2007, 45 (17), 3833-3842]

3.4. Evaluation of Crosslinked Microgels as Catalysts for the Hydrolysis of Glycosidic Bonds.

The synthesized microgels were prepared for catalysis by applying modified protocols for purification by dialysis and metal ion reloading that were originally developed for noncrosslinked microgel systems. [Striegler 2012; Striegler 2011; Gichinga 2010] In short, aliquots of the aqueous microgel dispersions were dialyzed against aqueous EDTA solution to remove Cu(II) ions, excess galactose, and any nonpolymerized monomer, followed by dialysis against water and aqueous alkaline CAPS buffer solution to prepare for metal ion reloading. In contrast to previous protocols, all dialysis solutions contained SDS emulsifier at a concentration equivalent to that used during microgel synthesis to prevent particle agglomeration or precipitation.

The catalyst in the dialyzed microgels was then activated by the addition of appropriate aliquots of aqueous Cu(II) acetate solutions. The respective metal ion amount was correlated to the content of immobilized ligand, assuming near quantitative complex formation and based on the overall N-content, as determined by elemental analysis. Corresponding procedures were described in detail for related, noncrosslinked systems and result in near quantitative catalyst activation, as monitored by isothermal titration calorimetry and EPR spectroscopy.

Figure 9:
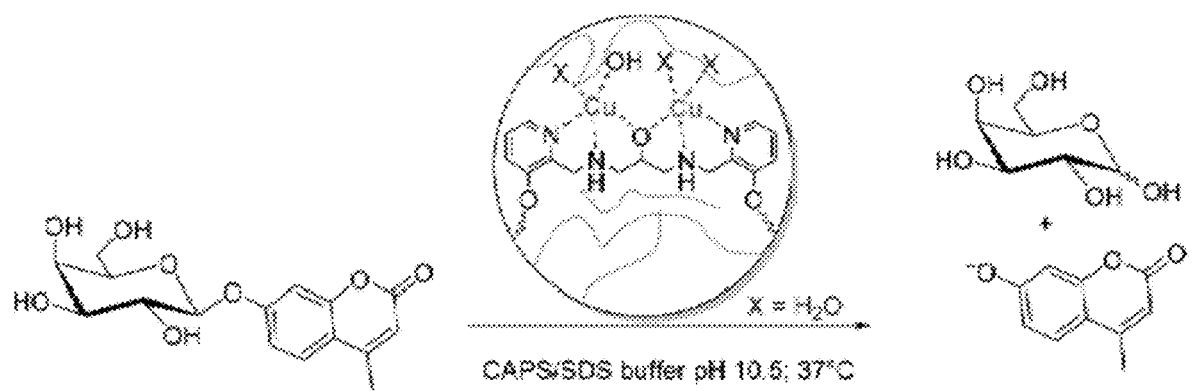
FIG. 9 shows a model reaction to monitor the catalytic hydrolysis of glycosidic bonds.

The turbidity of the aqueous microgel dispersions under consideration here increases visibly to the naked eye with the crosslinking content from 5 to 80 mol % EGDMA. As a consequence, the apparent extinction coefficient ($\varepsilon_{app}$) was determined for each microgel under the respective assay conditions prior to analysis of related spectroscopic data. The cleavage of the glycosidic bond of 4-methylumbelliferyl β-D-galactopyranoside (6) was then monitored by fluorescence readouts ($\lambda_{ex}$=360 nm; $\lambda_{em}$=465 nm) to follow the formation of 4-methylumbelliferone (7) in aqueous CAPS/SDS buffer at pH 10.50 and 37° C. (FIG. 9). [Chen, R. F Anal. Lett. 1968, 1(7), 423-428] The alkaline conditions were selected to match previous investigations of glycoside hydrolyses with low molecular complexes. [Striegler 2010] and used here to establish catalytic activity of the newly synthesized crosslinked microgels. The assay was developed in a 96-well plate format to allow fast catalyst screening under various reaction conditions, including lower pH values in future efforts.

Figure 10:
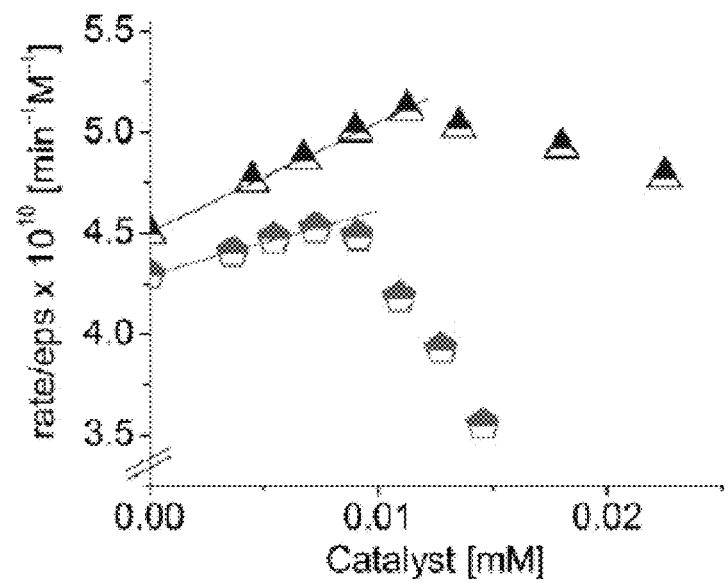
FIG. 10 shows linear range of catalytic activity for the hydrolysis of a constant amount of 6 in the presence of increasing concentration of catalysts Cu2LPgal (pink pentagon) and Cu2bpdpo) (blue triangle); SDS/CAPS buffer solution at pH 10.50 and 37° C.

Prior to in-depth kinetic evaluation of the microgels as catalysts, the dependence of the glycoside hydrolysis on the catalyst concentration was determined. Along these lines, a microgel dispersion with 60 mol % crosslinking content was used in overall ligand concentrations between 0 and 15 μM to hydrolyze a constant 3.4 mM aqueous solution of glycoside 6 in 50 mM CAPS buffer at pH 10.50 and 37° C. A microgel concentration up to 7 μM correlates linearly to the product formation, validating the subsequent analysis of kinetic data in this concentration range by the Michaelis-Menten model (FIG. 10).

Figure 11:
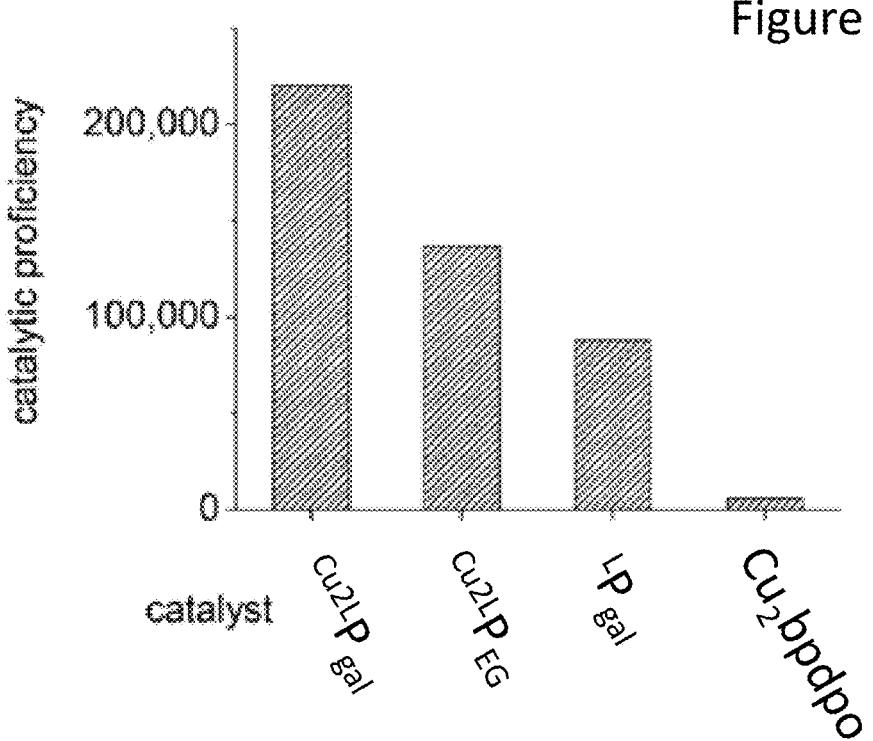
FIG. 11 shows the proficiency of selected catalysts for the hydrolysis of 6 in aqueous 50 mM CAPS buffer at pH 10.50 and 37° C.

Likewise, a linear correlation between the concentration of the low molecular weight complex $Cu_2$bpdpo (2) and the product formation of the glycoside hydrolysis was observed when the catalyst was used in concentrations up to 12 μM under assay conditions. With a fast screening assay on hand, the hydrolysis of glycoside 6 was evaluated with two different microgel catalysts at 60% crosslinking content: a polymer $^{\alpha}P_{gal}$ prepared in the presence of galactose and its metal-free, nonactivated analogue $^{L}P_{gal}$. Control experiments were conducted using a microgel $^{Cu2L}P_{EG}$ that has the same crosslinking content as those polymers above, but is prepared in the presence of ethylene glycol instead of galactose. Additionally, hydrolysis of 6 was followed in the presence of low molecular weight complex $Cu_2$bpdpo (2) and in the absence of catalyst in the buffer solution itself. The resulting hyperbolic data for the glycoside hydrolyses were analyzed by applying the Michaelis-Menten model to obtain the rate of the reaction ($k_{cat}$), the substrate affinity ($K_M$), and the rate of the uncatalyzed reaction ($k_{non}$) in aqueous buffer solution. The catalytic proficiency ($k_{cat}/(K_M \times k_{non})$), catalytic efficiency ($k_{cat}/K_M$), and acceleration of the reaction over the uncatalyzed background reaction ($k_{cat}/k_{non}$) were then calculated therefrom as described (Table 1, FIG. 11).

For the metal ion-free, nonactivated control polymer $^{L}P_{gal}$, only a linear fit could be applied to the data to derive an approximation of the catalytic efficiency. The control polymer $^{Cu2L}P_{EG}$ behaves likewise. The hydrolysis of the glycoside 6 is 38-fold faster when catalyzed by $^{Cu2L}P_{gal}$ (Table 1, entry 1) in comparison to low molecular weight complex 2, and 2.5-fold faster when compared to metal-free microgel $^{L}P_{gal}$. In turn, the catalytic proficiency of a metal-free microgel $^{L}P_{gal}$ toward the hydrolysis of 6 is 1 order of magnitude higher than the catalytic proficiency of the low molecular weight complex Cu$_2$bpdpo (2) (Table 1, entries 3 and 4). Thus, the influence of the matrix of the microgel is most significant for the overall catalyst performance during hydrolysis of 6.

Figure 12:
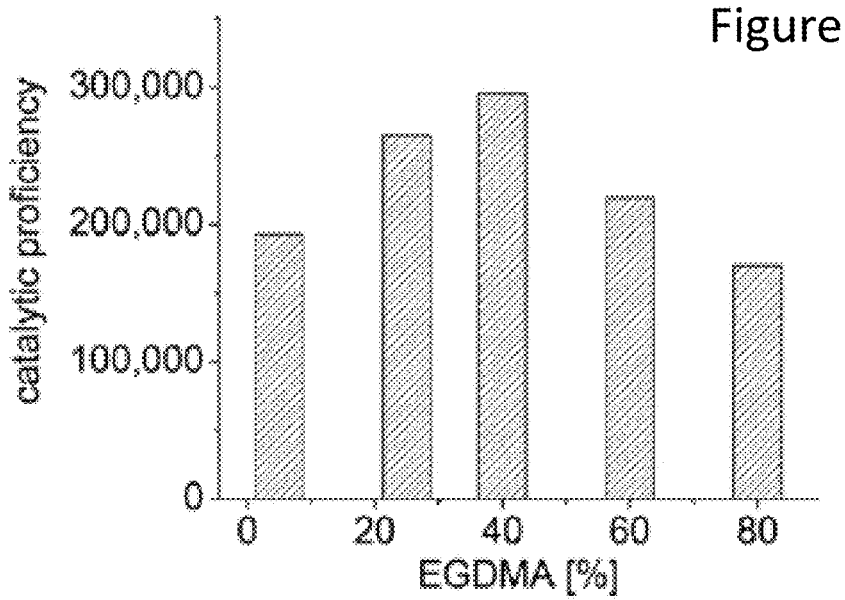
FIG. 12 shows the proficiency of microgel $^{Cu_2L}P_{gal}$ catalysts with a crosslinking content between 5 and 80 mol % of EGDMA for the hydrolysis of 6 in aqueous 50 mM CAPS buffer at pH 10.50 and 37° C.

The choice of the counterion during microgel preparation also had an effect on the overall catalyst performance resulting in a 1.6-fold higher catalytic proficiency of $^{Cu2L}P_{gal}$ over $^{Cu2L}P_{EG}$ under otherwise identical conditions (Table 1, entries 1 and 2). A variation of the crosslinking content in the microgel matrix between 5 and 80 mol % discloses the highest catalytic proficiency for the hydrolysis of glycoside 6 by microgels with 40 mol % EGDMA (FIG. 12). We hypothesize that the active sites of the microgels with enhanced crosslinking content are not freely accessible to the substrate. This finding further highlights the contributions of the matrix to the overall catalytic performance of the otherwise identical microgels. [Golker, K. et al. Eur. Polym. J. 2016, 75, 423-430]

The kinetic study establishes a high catalytic proficiency of water-soluble microgels that rivals those of corresponding glycoside-transforming catalytic antibodies 54 and outperforms the catalytic activity of its low molecular weight analog 2. Most notably, the microgel matrix contributes significantly to the overall catalytic performance and will be subject to modifications in future efforts.

3.5. Conclusion.

A new polymerization procedure was developed for the synthesis of microgels from BA and EGDMA with a crosslinking content between 5 and 80 mol % at ambient temperature or below. Near quantitative immobilization of a pentadentate ligand as catalyst precursor was achieved. The microgels were characterized using DLS, TEM, TGA, elemental analysis, EDX, and MALDI, UV/vis, and IR spectroscopies. The mean hydrodynamic diameters of the resulting microgels were between 210 and 280 nm in aqueous solution. The study disclosed competing phenomena with increasing crosslinking content encompassing particle enlargement and reduced swelling capacity in dependence of matrix rigidity. Sufficient thermal stability of the microgels below 100° C. and high chemical stability between pH 1 and 13 were also recognized, indicating a large range of operation for the synthesized microgels during catalysis.

Lastly, the catalytic activity of the microgels was demonstrated using the hydrolysis of 4-methylumbelliferyl β-D-galactopyranoside (6) as a model reaction. The reaction is more than 5 orders of magnitude, or 220000-fold, faster in the presence of catalyst $^{Cu2L}P_{gal}$ than the uncatalyzed reaction. The same catalyst accelerates the reaction 38-fold over its low molecular weight analog Cu$_2$bpdpo (2) and 1.6-fold over metal ion free control polymers, indicating a large contribution of the matrix to the overall observed proficiency of the catalyst. A comparison of the catalytic activity of microgels synthesized with 5 to 80 mol % of crosslinking EGDMA reveals differences in their catalytic turnover ability depending on the rigidity of the matrix. A bell-shape correlation between catalyst proficiency and crosslinking content was observed that peaks at 40 mol %.

Example 2: Biomimetic Glycoside Hydrolysis by a Microgel Templated with a Competitive Glycosidase Inhibitor 1. Introduction We have developed biomimetic catalysts for the hydrolysis of glycosidic bonds with high proficiency under conditions where enzymes are not suitable, functional, or stable. Biomimetic catalysts may also be used to transform glycosides that are not substrates of conveniently available natural enzymes. In order to design such catalytic entities, we initially studied the inhibition of selected glycosidases with a small library of 25 galactonoamidines to elucidate stabilizing interactions in their active sites by inhibitor design. [Pedersen 2017; Wang, B. et al. Chem. Sci. 2017, 8, 7383-7393.] All galactonoamidines are very potent competitive inhibitors toward β-galactosidases from A. oryzae and bovine liver. [Murakami, Y. et al. Chem. Rev. 1996, 96, 721-758; Pickens, J. B. et al. Bioorg. Chem. 2018, 77, 144-151; Fan, Q.-H. et al. Org. Biomol. Chem. 2014, 12, 2792-2800; Kanso, R. et al. Tetrahedron 2012, 68, 47-52] However, only a few, e.g. galactonoamidine (1), were experimentally characterized as transition state analogues (TSAs) of the reaction (Chart 2), while others were identified as fortuitous binders in the active site. The transition state like character of 1 was determined by correlating inhibition constants ($K_i$) to catalytic efficiencies ($k_{cat}/K_m$) in a kinetic analysis with various substrate analogues. [Bartlett, P. A. et al. Biochemistry 1983, 22, 4618-4624] Toward the development of potent biomimetic glycosidase mimics, we describe here the mimicry of induced-fit interactions in microgels. The study focuses on illuminating the contribution of shape recognition toward the overall catalytic proficiency of cross-linked microgels using TSAs of the reaction during material preparation. For comparison, the performance of the water-dispersed microgels is contrasted with the proficiency of β-galactosidase (bovine liver) in alkaline and neutral aqueous solution.

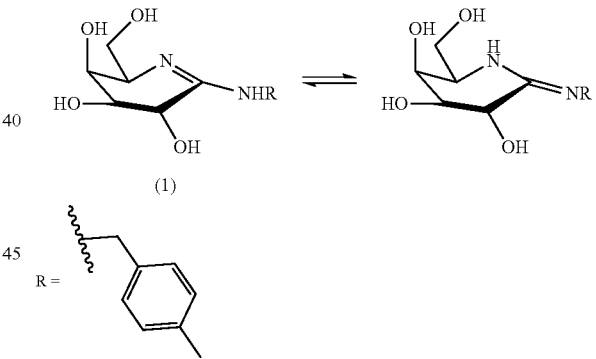

Chart 2. Structure of p-Methylbenzyl-D-galactonoamidine

2. Materials and Methods 2.1. General Remarks.

The instrumentation, reagents, and materials for this study were recently described. [Sharma, B. et al. Biomacromolecules 2018, 19, 1164-1174; Sharma, B. et al. ACS Catal. 2018, 8, 7710-7718] The computational analysis was performed with PQSmol as reported. [Sharma Biomacromolecules 2018; Sharma ACS Catal. 2018; Striegler, S. et al. Dalton Trans. 2016, 45, 15203-15210; Becke, A. D. J. Chem. Phys. 1993, 98, 5648-5652; Lee, C. et al. Phys. Rev. B: Condens. Matter Mater. Phys. 1988, 37, 785-789; PQSmol, Version 4.1; Parallel Quantum Solutions: Fayetteville, A R, 2013; Mitin, A. V. et al. J. Chem. Phys. 2003, 118, 7775-7782] Additionally, NMR spectroscopy was performed on a 400 MHz instrument (Bruker) in D$_2$O, and the stability of galactonoamidine 1a was monitored on a HPLC system (Shimadzu). [Pickens, J. B. et al. Bioorg. Med. Chem. 2016, 24, 3371-3377]

2.2. Microgel Synthesis and Characterization.

The TSA-templated microgel was synthesized with a matrix composition of 60 mol % EGDMA using 1a as a template following previously disclosed procedures with some modifications as specified. [Sharma Biomacromolecules 2018; Sharma ACS Catal. 2018] The galactonoamidine (25.25 mg, 94.46 µmol) was added after and not before sonication to the prepolymerization mixture to avoid premature decomposition of the biomolecule. The polymerization then progressed as described. The microgel was purified by dialysis prior to elemental analysis and freeze-dried. Anal. Calcd for $^LP_1$ (60% EGDMA): C, 62.08; H, 7.81; N, 0.16. Found: C, 61.42; H, 7.86; N, 0.15.

2.3. Microgel-Catalyzed Glycoside Hydrolyses.

All glycoside hydrolyses were observed at 37° C. in 50 mM CAPS buffer at pH 10.50 or in 5 mM HEPES buffer solution at pH 7.00. Activated microgel catalysts were prepared as described. [Sharma Biomacromolecules 2018] Typical stock solutions were as follows: Cu2bpdpo (5) 2 mM, β-galactosidase as described [Sharma ACS Catal. 2018], 4-methylumbelliferyl α-D-galactopyranoside (α-9) 8-9 mM, and 4-methylumbelliferyl α-D-galactopyranoside (β-9) 3-4 mM. The formation of 4-methylumbelliferone (8) was followed by fluorescence spectroscopy ($\lambda_{ex}$ 360 nm; $\lambda_{em}$ 465 nm) over 1-6 h. Detailed procedures to perform kinetic assays based on fluorescence spectroscopy [Sharma Biomacromolecules 2018; [Sharma ACS Catal. 2018] and the subsequent data analyses in the presence and absence of inhibitors, the determination of kinetic parameters, inhibition constants, efficacy studies, and $IC_{50}$ values are described in detail elsewhere. [Pickens, J. B. et al. Bioorg. Med. Chem. 2017, 25, 5194-5202; Fan, Q.-H. et al. Bioorg. Med. Chem. 2016, 24, 661-671; Pickens 2016]

3. Results and Discussion

Glyconoamidines are prone to nucleophilic attack at the anomeric C atom and subsequent hydrolysis in alkaline solution. Various glyconoamidines have been previously synthesized. [Bleriot, Y. et al. Bioorg. Med. Chem. Lett. 1995, 5, 2655-60; Bleriot, Y. et al. Tetrahedron Lett. 1994, 35, 1867-70; Heck, M.-P. et al. J. Am. Chem. Soc. 2004, 126, 1971-1979; Ganem, B Acc. Chem. Res. 1996, 29, 340-347] We evaluated the hydrolysis of galactonoamidine 1 under various buffer and temperature conditions to ensure its stability under polymerization conditions.

3.1. Stability of Galactonoamidine 1 Under Polymerization Conditions.

Figure 13:
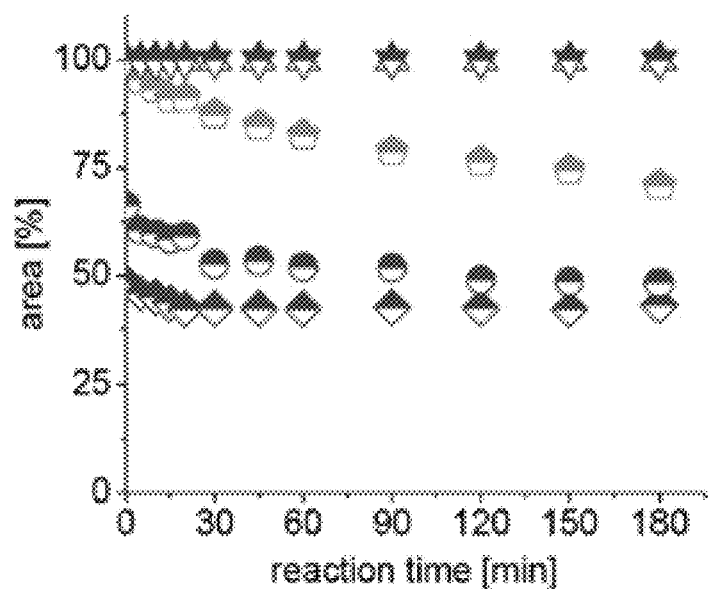
FIG. 13 shows the stability of galactonoamidine against hydrolysis in 5 mM HEPES, TAPS, or CAPS buffer at 0 and 10° C. (green ∇), 5 mM TAPS at 20° C. (green Δ), mM TAPS buffer at 30° C. (orange ☌), 50 mM TAPS buffer at 30° C. (red ○), and 50 mM TAPS or CAPS buffer 72° C. (red ◇).
Figure 14:
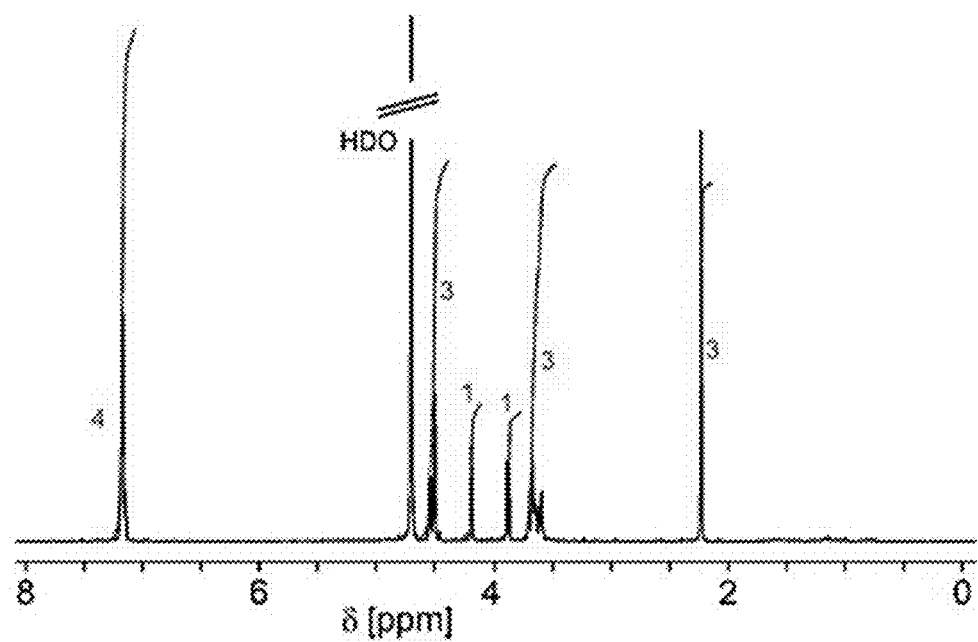
FIG. 14 shows a $^1$H NMR spectrum of 1 after exposure to $D_2O$ at 72° C. over 3 h.

Initially developed protocols for microgel synthesis involved thermally initiated free-radical polymerization conditions in 50 mM CAPS buffer at pH 10.50 and 72° C.37 Under these conditions, 1 undergoes instant hydrolysis and formation of galactonolactam (2), as concluded by a combination of preparative HPLC, $^1$H NMR spectroscopy, and ESI mass spectrometry studies. Lowering the buffer strength from 50 to 5 mM while the temperature and pH were maintained slowed the hydrolysis of 1 and allowed following the formation of 2 by time-dependent analysis of aliquots using HPLC, but it did not prevent it. However, galactonoamidine 1 is stable in pure deuterium oxide at 72° C. over a 3 h time period, identifying the alkaline conditions and not the temperature as the driving force for the hydrolysis (FIG. 14). The stability of 1 was also observed at 0 and 10° C. over a 3 h time period in 5 mM CAPS buffer solution at pH 10.50. Buffer solutions with similar molarity at lower pH values behave likewise (FIG. 13).

Figure 15:
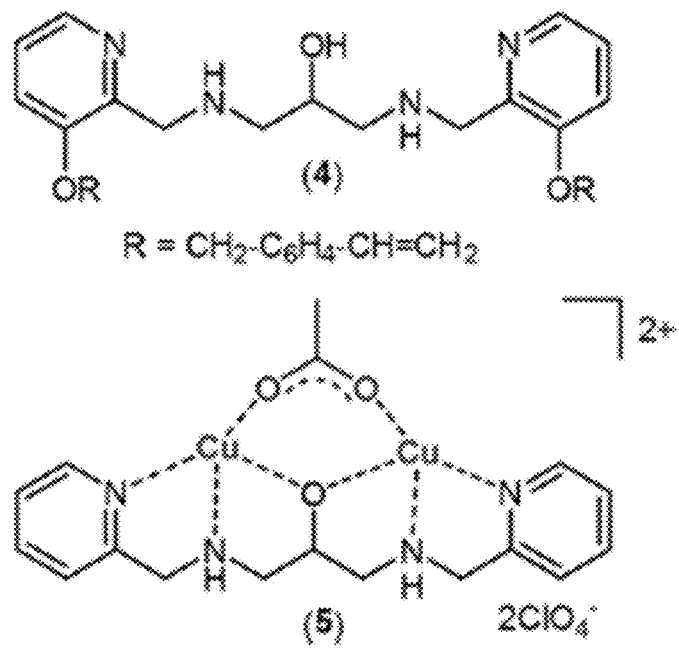
FIG. 15 shows the structures of polymerizable ligand VBbpdpo and the binuclear complex $Cu_2$bpdpo.

The results indicate that a thermally initiated polymerization protocol in alkaline solution is not suitable for preparing microgels in the presence of galactonoamidines. The free radical polymerization is initiated by UV light under ice cooling and allows quantitative immobilization of the binuclear complex $Cu_2$VBbpdpo (3) in the presence of sugar ligands in alkaline solution. The complex is prepared in situ from the polymerizable ligand VBbpdpo (4) and copper acetate as described (FIG. 15). [Striegler 2011] The coordination between metal temperature and high pH values due to the decreased flexibility of bonds and deprotonation of sugar binding sites. For further catalyst design, characterization of binding sites and binding strengths between TSA-like amidine 1 and the metal complex core is desirable.

3.2. Coordination of Galactonoamidine 1 under Polymerization Conditions.

Figure 16:
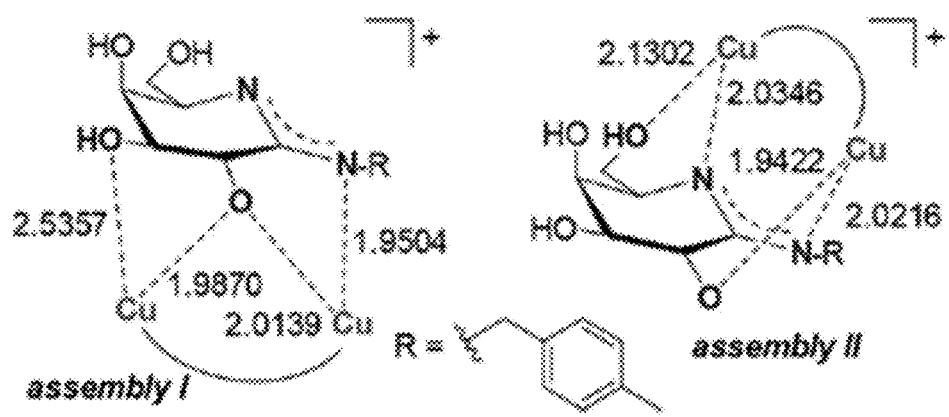
FIG. 16 shows a schematic display of computed coordination sites in galactonoamidine upon interaction with $Cu_2$bpdpo involving the hydroxyl group at C-3 (assembly I) and C-6 (assembly II). Distances are given in Å.

The coordination of galactonoamidine 1 to binuclear complexes was already evaluated in part and included $Cu_2$bpdpo (5), a nonpolymerizable analogue of 3 (FIG. 15). [Striegler, S. et al. J. Catal. 2016, 338, 349-364; Striegler, S.; et al. J. Am. Chem. Soc. 2003, 125, 11518-11524; Gajda, T. et al. J. Chem. Soc., Dalton Trans. 2002, 1757-1763] As the two metal complexes are different in the ligand backbone periphery, but not the metal site itself, the coordination of galactonoamidine 1 to both metal complexes is comparable. [Striegler 2011; Striegler 2010] Strong chelation of 1 to 5 over three binding sites was observed in aqueous CAPS buffer solution at pH 10.50 and 10° C. Coordination experiments with various galactonoamidines revealed a Gibbs free energy of binding of −10.3 kcal mol$^{-1}$ for the 1-5 assembly that translates into a pKa,1-5 of 3.5 using isothermal titration calorimetry. The coordination of 1 involves its deprotonated amidine function, the hydroxyl group at C-2, and a third unspecified site. [Striegler 2016] The experimental data excluded coordination of 1 over the hydroxyl group at C-4 but did not elucidate possible coordination of the amidine over the hydroxyl groups at C-3 or C-6. To characterize the association between 1 and 5 further, a computational approach based on density functional theory is used herein. The B3LYP exchange correlation functional was employed with an m6-31G(d) basis set that contains improved functions for transition metals. Structures and Gibbs free energies of 1-5 assemblies were computed in aqueous solution by applying the COSMO model under standard conditions. [Klamt, A. et al. J. Chem. Soc., Perkin Trans. 2 1993, 799-805] The computed assemblies include the already experimentally identified coordination sites of the amidine in addition to the hydroxyl group at C-3 yielding assembly I and at C-6 for assembly II (FIG. 16).

The computed Gibb's free energy for assembly I is 23.4 kcal mol$^{-1}$ lower than for assembly II. Therefore, we assign the hydroxyl group at C-3 of amidine 1 as a third coordination site upon interaction with 5. The result of the calculations is in very good agreement with coordination sites reported for carbohydrates as ligands of metal ions and complexes. [Gyurcsik, B. et al. Coord. Chem. Rev. 2000, 203, 81-149] With suitable conditions for amidine stability and a fully characterized 1-5 assembly in hand, we synthesized the corresponding microgel catalysts.

3.3. Microgel Synthesis and Characterization.

Figure 17:
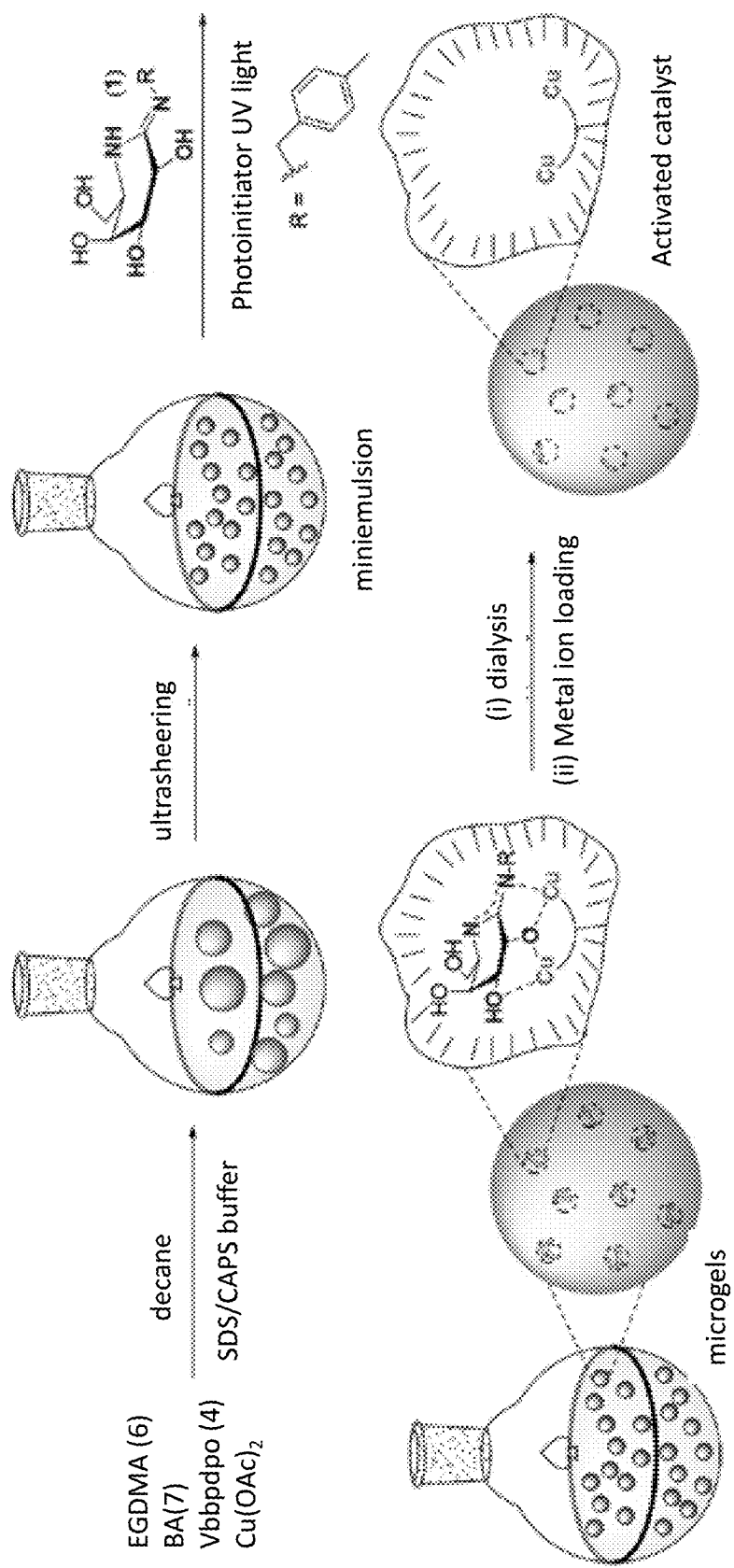
FIG. 17 shows the synthesis of amidine-templated microgels $^{Cu_2L}P_1$.

Example 1 discloses the highest catalytic proficiency for microgels prepared in the presence of galactose at a cross-linking content of 40 mol %. However, galactose weakly coordinates to the metal complex under the conditions of microgel synthesis (pKa, gal=2.70; pH 10.50, 10° C.). The catalytic performance of corresponding microgels was thus related to contributions of the matrix and not to a templating effect of the sugar. In contrast, microgels prepared in the presence of strongly coordinating carbohydrates, such as mannose, peak in catalytic proficiency at 60 mol % cross-linking and show an increased catalytic performance related to a small templating effect. Due to strong binding interactions in the 1-5 assembly, galactonoamidine-templated polymers are prepared at a cross-linking content of only 60 mol %. Given the time-dependent stability of 1 against hydrolysis in alkaline solution, the elaborated polymerization protocol of Example 1 altered and 1 was added after sonication of the otherwise identically prepared prepolymerization mixture. In more detail, microgels $^{Cu2}L_{P1}$ were prepared at 60 mol % of cross-linker by mixing corresponding amounts of ethylene glycol dimethacrylate (6) and butyl acrylate (7) with the ligand VBbpdpo (4), copper(II) acetate, and decane in SDS/CAPS buffer (FIG. 17). After ultrasheering of the resulting mixture, amidine 1 was added in a 5-fold molar excess relative to the in situ formed metal complex Cu$_2$VBbpdpo (3). To ensure saturation of all binding sites, the microgel synthesis was initiated under UV light after a 30 min waiting time and then maintained over 60 min. For control experiments, microgels were synthesized in the presence of galactose as described. All microgels were purified by repetitive dialysis cycles against aqueous EDTA, SDS, and SDS/CAPS solution as elaborated previously.

Dynamic light scattering experiments with $^{L}P_1$ revealed a narrow dispersity of the particles (PDI=0.097) and a hydrodynamic diameter D$_h$ of 283±0.5 nm. The molar weight of the microgel was estimated as 3.6×108 Da. Combustion data of freeze-dried aliquots of $^{L}P_1$ confirmed near-quantitative incorporation of the polymerizable ligand 4. Activation of the microgel catalysts was achieved by addition of the corresponding amounts of aqueous copper(II) acetate solution as described in Example 1. The metal ion reloading procedure was previously shown to be near-quantitative and results in catalytically active microgels. Extensive efforts aiming at the characterization of related microgels by NMR and EDX spectroscopy, GPC, TEM, and MALDI-TOF mass spectrometry were futile and are thus not repeated here.

3.4. Evaluation of Catalytic Glycoside Hydrolyses in Alkaline Solution.

To assess the catalytic ability of the TSAtemplated microgel and allow comparisons with previously synthesized microgels, the protocol as described in Example 1 to monitor glycoside hydrolyses in alkaline solution was employed. The 96-well plate assay follows the formation of 4-methylumbelliferone (8) from 4-methylumbelliferyl glycopyranosides using fluorescence spectroscopy. Here, 4-methylumbelliferyl-α-D-galactopyranoside (α-9) and its β-analogue (β-9) were hydrolyzed in 50 mM CAPS buffer at pH 10.50 and 37° C.

Model Reaction for Catalyst Screening

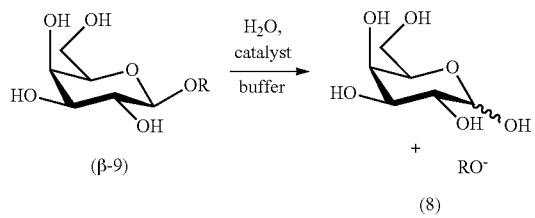

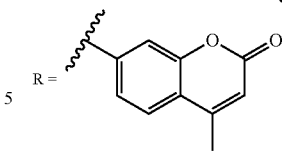

The catalytic proficiency of microgels prepared in the presence of galactose and amidine 1 was then evaluated in comparison to the performance of the low-molecular-weight complex Cu2bpdpo (5). The collected fluorescence data were transformed into concentrations using apparent extinction coefficients that were separately determined for each microgel dispersion at a constant catalyst concentration. The obtained product concentrations were plotted over time to deduce the rates of the reactions from the initial slopes. The obtained data were then graphed over the corresponding substrate concentration and analyzed by nonlinear regression. The application of the Michaelis-Menten model yielded the kinetic rate constant (k$_{cat}$) and the binding affinity (K$_M$) (Table 2) by standard methods. [Striegler 2011; Striegler 2012] For control reactions, the uncatalyzed substrate hydrolysis was treated likewise, yielding the kinetic rate constant in the absence of a catalyst (k$_{non}$). The catalytic efficiency (k$_{cat}$/K$_M$) and proficiency (k$_{cat}$/K$_M$×k$_{non}$) of each microgel was finally deduced from the kinetic parameters. As the uncatalyzed hydrolysis of the substrates α-9 and β-9 differs by 2 orders of magnitude (Table 2), only the catalytic proficiency of the catalysts is discussed herein.

Microgels prepared in the presence of galactose show the highest proficiency toward the hydrolysis of α-9 at a cross-linking content of 40 mol % (Table 2, entries 2-6). The result is in very good agreement with previous findings revealing similar performance of the microgels upon catalytic hydrolysis of β-9 (Table 2, entries 10-14). The catalytic proficiency of microgel $^{Cu2}L_{P1}$ for the hydrolysis of both substrates is only about 1.5-fold higher than the proficiency of microgels prepared in the presence of galactose with 40 or 60 mol % of cross-linking content. Thus, a templating effect related to the flattened chair of 1 is noted, but its contribution to increase the catalytic proficiency of $^{Cu2}L_{P1}$ is small. A catalyst design solely relying on templating effects thus appears inferior and insufficient. Instead, a combination of stabilizing interactions will have to be elaborated to support the catalytic turnover of the targeted reaction.

Figure 18:
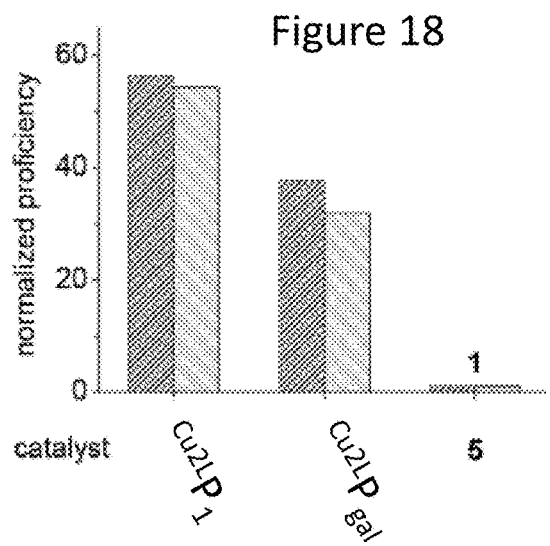
FIG. 18 shows the catalytic proficiency of microgel catalysts relative to the performance of $Cu_2$bpdpo in 50 mM CAPS buffer at pH 10.50 and 37° C. for the hydrolysis of α-9 (cyan; right) and β-9 (blue; left).

However, when the catalytic proficiency of the microgel catalysts is normalized against the performance of the low molecular-weight complex 5, microgel $^{Cu2}L_{P1}$ shows comparable proficiency toward the hydrolysis of both substrates, α-9 and β-9 (FIG. 18). The catalytic proficiency of $^{Cu2}L_{P1}$ is 1.21×106 for the hydrolysis of α-9 and, remarkably, more than 56-fold higher than that of 5. This result classifies $^{Cu2}L_{P1}$ as one of the most proficient biomimetic catalysts known. A discrimination of substrates was not expected, as the current catalyst design does not include elements to promote stereoselectivity. Additionally, we used β-galactosidase (bovine liver) in alkaline solution for the hydrolysis of β-9 and determined its kinetic parameters (Table 2, entry 16). Compound α-9 is not a substrate for the enzyme and was consequently not evaluated.

The calculated catalytic proficiency is about 3250-fold higher than that of the metal complex 5 and about 57-fold higher than that of the amidine-templated microgel $^{Cu2}L_{P1}$. To further assess the performance of the microgels as biomimetic models and use conditions optimized for enzymatic reactions, we evaluated the catalytic glycoside hydrolysis at physiological pH.

3.5. Evaluation of Catalytic Glycoside Hydrolysis at Neutral pH.

A previous evaluation of more than 25 galactonoamidines as inhibitors of enzymatically catalyzed glycoside hydrolyses classified glyconoamidines as competitive inhibitors of various glycosidases with inhibition constants in the low nano- or picomolar concentration range. [Pickens 2017; Pickens 2018; Fan 2016] To evaluate the synthesized microgel $^{Cu2}L_{P1}$ as a biomimetic catalyst of β-galactosidases, the efficacy of its inhibition with 1 was determined as a first step, followed by determination of the inhibition type, inhibition constant, and evaluation of dependence of catalytically active sites. As the enzyme only transforms β-glycosidic bonds, β-9 was used as a model substrate. The study was conducted in 5 mM HEPES buffer at pH 7.00 using fluorescence spectroscopy.

Figure 19:
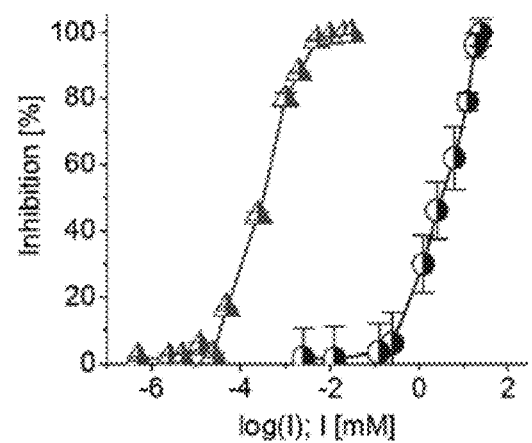
FIG. 19 shows the efficacy of the inhibition of hydrolysis of β-9 by β-galactosidase (bovine liver, green triangle) and microgel $^{Cu_2L}P_1$ (blue circle)

For the determination of the efficacy of inhibition, the hydrolysis of β-9 was correlated with its partial hydrolysis in the presence of inhibitor 1. The obtained data were plotted as percent inhibition over the logarithmic inhibitor concentration to determine the efficacy for β-galactosidase and the microgel catalyst $^{Cu2}L_{P1}$ (FIG. 19). The $IC_{50}$ values were estimated graphically (Table 3).

The efficacy of inhibition is about 5 orders of magnitude higher for the enzyme in comparison to the microgel and nonetheless classifies 1 as an efficient inhibitor of both catalysts. While the stabilization of 1 in the active site of the β-galactosidase is, as expected, significantly better than that in the catalytic site of the microgel, the activity of $^{Cu2L}P_1$ can be nearly quantitatively inhibited in the presence of 1. This observation points at strong interactions of 1 with the metal complex core active sites in the microgel and simulates inhibitor binding in the active sites of an enzyme.

Figure 20:
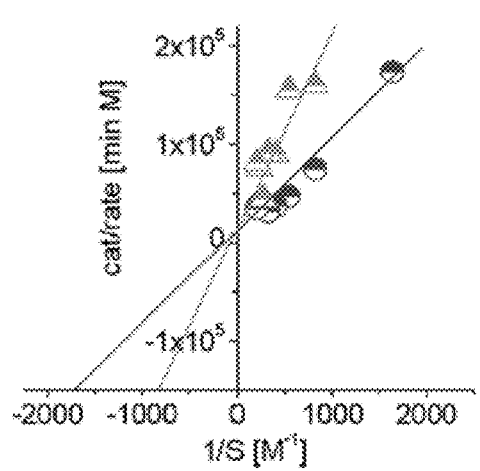
FIG. 20 shows Lineweaver-Burk plot showing competitive inhibition of $^{Cu_2L}P_1$ by galactonoamidine: I=0 μM (red circle); I=0.01 μM (orange triangle).

Galactonoamidine 1 was then further characterized as a competitive inhibitor toward microgel $^{Cu2L}P_1$ and β-galactosidase using standard kinetic assays. The obtained data were depicted as a Lineweaver-Burk plot to visualize 1 as a competitive inhibitor of the microgel-catalyzed glycoside hydrolysis (FIG. 20). Subsequently, the apparent kinetic parameters k'cat and K'M were determined for the hydrolysis of β-9 by $^{Cu2L}P_1$ in the presence of 1 and $k_{cat}$ and $K_M$ in the absence of 1. The inhibition constant Ki of the microgelcatalyzed glycoside hydrolysis was deduced from these values using standard methods and discloses millimolar inhibition of the microgel and picomolar inhibition of the enzyme (Table 3). [Segel, I. H. Enzyme kinetics: Behavior and Analysis of Rapid Equilibrium and Steady-State Enzyme Systems; Wiley Classics Library: New York, 1993; Jencks, W. P. Catalysis in Chemistry and Enzymology; Dover Publications: New York, 1986]

Thus, the stabilization of 1 by the enzyme is more sophisticated than that by the microgel, but the determined inhibition nevertheless points at a very potent microgel catalyst. Additionally, the binding affinity KTS of a transition state of a reaction to the active site in an enzyme can be expressed as the reciprocal catalytic proficiency $K_M \times (k_{non}/k_{cat})$ (Table 3). While the affinity of binding of the transition state during the hydrolysis of β-9 by the enzyme is as low as 10-14, the microgel $^{Cu2L}P_1$ still reaches 10-7, which again indicates a remarkable stabilization of the transition state of glycoside hydrolysis through the man-made catalyst. The stabilization of the enzyme-catalyzed hydrolysis of β-9 is 3.5×106 fold higher than that of the microgel. However, considering that glycosidases are known as being the most proficient among all enzymes, 9 the catalytic performance of $^{Cu2L}P_1$ remains unprecedented. The TSA-templated microgel surpasses the activity of catalytic antibodies prepared for the same reaction [Choi, S.-Y. et al. Mol. Cells 2002, 13, 463-469], shows very high catalytic activity in aqueous buffered solution without the addition of organic solvents, and thereby distinguishes itself from other biomimetic catalysts.

Figure 21:
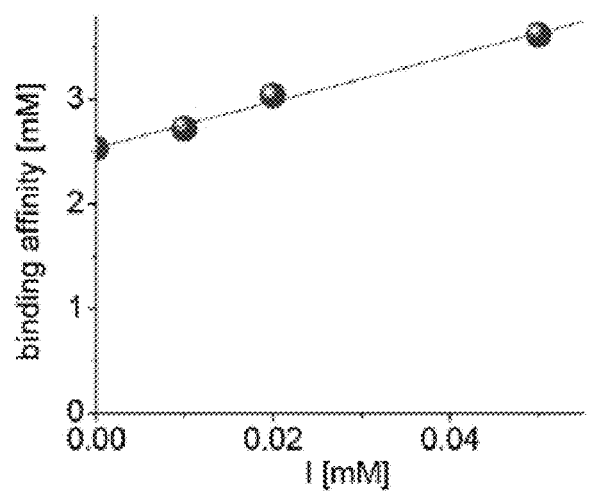
FIG. 21 shows independence of catalytic sites in $^{Cu_2L}P_1$ ($R^2$=0.992).

Finally, β-galactosidase (bovine liver) exists as a monomer at pH 7.00, and thus all catalytic activity is ascribed to a single active site. Each particle of the microgel $^{Cu2L}P_1$, however, contains at least 6000 molecules of backbone ligand 4. Using the known volume of the overall solution at 9.6 mL, the mean hydrodynamic diameter $D_h$ of the microgels as 283 nm, and the ligand content in the microgel as determined by elemental analysis as 0.789 mM allows the calculation of a minimum number of ligand molecules per particle. To determine whether those sites interact with each other during catalytic turnover, the apparent binding affinity was correlated to the inhibitor concentration. The linear correlation of the data discloses independence of the catalytically active sites (FIG. 21).

3.6. Conclusions.

The study evaluated contributions of shape recognition on catalytic glycoside hydrolyses by microgel catalysts to increase stabilizing interactions during the transition state of the reaction. A galactonoamidine, previously identified as a potent competitive inhibitor and putative transition state analogue of β-galactosidases, was coordinated to a binuclear metal complex and used for the synthesis of a TSA-templated microgel. The resulting material was characterized by almost quantitative incorporation of a catalytic center, yielding microgel particles with a hydrodynamic diameter of about 283 nm, narrow dispersity, and more than 6000 independent catalytic sites per particle.

The catalytic performance of microgels $^{Cu2L}P_1$ and $^{Cu2L}P_{gal}$ was subsequently elaborated in aqueous alkaline and neutral solution. The catalytic performance of all microgels is in the same order of magnitude, 1.5-fold higher for the TSA-templated microgel $^{Cu2L}P_1$ in comparison to the most proficient microgel $^{Cu2L}P_{gal}$, and independent of substrate. Thus, a templating effect due to the shape of the galactonoamidine template is noted to contribute to the catalytic proficiency of the latter microgel catalyst $^{Cu2L}P_1$, but it does not control its performance. Instead, the synergy of stabilizing interactions comprised of strong interactions with a binuclear metal complex core, the cross-linking content of the matrix, and templating of the immediate surrounding of the metal site allow constructing a microgel catalyst with advanced catalytic proficiency. Notably, the microgel is not specific toward a single substrate and allows the hydrolysis of α- and β-glycosidic bonds. Our findings thus contradict various reports in the field of molecularly imprinted catalysts ascribing major and dominating effects on the catalytic outcome to templating effects. This work demonstrates that proficient biomimetic catalysts for the hydrolysis of glycosides may be achieved by tailoring the matrix of biomimetic microgels by other means.

Example 3: Tailored Interactions of the Secondary Coordination Sphere Enhance the Hydrolytic Activity of Crosslinked Microgels 1. Introduction We previously immobilized a polymerizable derivative of binuclear copper(II) complex $Cu_2$bpdpo (1) in a microgel matrix consisting of ethyleneglycol dimethacrylate and butyl acrylate. [Striegler 2011] Complex 1 is known to catalyze the hydrolysis of glycosidic bonds and discriminate monosaccharides upon binding in aqueous alkaline solution (Scheme 1). [Striegler 2003]

Ultra-sheering of the monomer mixture in aqueous alkaline solution in presence of SDS surfactant and decane as a hydrophobe yielded water-dispersed microdroplets as described in Examples 1 and 3. UV-light initiated free radical polymerization in the cold provided water dispersed microgels with diameters between 250 and 280 nm. To ensure proliferation of the polymerization despite the presence of Cu(II) ions, strongly chelating monosaccharides and sugar derivatives were employed as templates during material preparation to mask the paramagnetic character of the metal ions. The resulting templating effect does contribute to the overall catalytic performance of the obtained macromolecular catalysts, but it does not control it. Instead, significant contributions to the overall catalytic proficiency of the microgels by the matrix surrounding the metal complex were noted. These preliminary results prompted a detailed study to elaborate the contributions of the secondary coordination sphere of an immobilized metal complex to the catalytic performance of hydrolytic microgels. Consequently, interactions of a metal complex-bound hydrophilic template, here mannose (2), and its surrounding matrix were examined (Chart 3).

3. Results and Discussion

3.1. Microgel Synthesis and Physical Characterization.

H-bond donating and accepting, π-π or CH-π stacking, and electrostatic and hydrophobic interactions were identified as dominating effects during the stabilization of the transition state of enzyme-catalyzed glycoside hydrolyses. [Wolfenden, R. Chem. Rev. 2006, 106, 3379-3396] To transfer these observations into the design of biomimetic catalysts, mannose-templated microgels with altered acrylate co-monomers were synthesized. It was hypothesized that the transition state-stabilizing interactions in the man-made material would increase by interactions in the second coordination sphere of the metal complex center. Those stabilizing interactions were then implemented in the microgels by partial substitution of the non-crosslinking butyl acrylate monomer. Therefore, 20 mol % of the butyl acrylate (3a) monomer were replaced by methoxyethyl acrylate (MEA, 3b), hydroxyethyl acrylate (HEA, 3c), heptafluorobutyl acrylate (HFBA, 3d), benzyl acrylate (BnA, 3e), dodecyl acrylate (DdA3f) and carboxyethyl acrylate (CEA, 3g) in the pre-polymerization mixture (Chart 4). The catalytic center in the microgels were generated as described by immobilization of 0.5 mol % of polymerizable ligand VBbpdpo (4) (Chart 5), and 1 mol % of copper(II) acetate in presence of 5 mol % of mannose during material synthesis.

Chart 3. Interactions of the metal complex 1 in the second coordination sphere

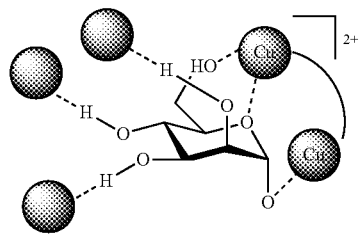

Along these lines, the hydrophobic butyl acrylate was partially substituted by acrylate co-monomers that enable H-bonding and electrostatic interactions. Acrylates that promote π-π or CH-π stacking interactions as well as strong hydrophobic van-der-Waals interactions were included in this study as controls. A very good correlation between the H-bond accepting ability of the acrylate co-monomers, their dipole moments, and the catalytic proficiency of the resulting microgels was observed, and is described in detail below.

2 Materials and Methods

Microgel synthesis. All microgels were prepared with 60 mol % EGDMA, 20 mol % BA and 20 mol % of co-monomer, i.e. butyl acrylate (BA, 3a), 2-methoxyethyl acrylate (MEA, 3b), 2-hydroxyethyl acrylate (HEA, 3a), 2,2,3,3,4,4,4-heptafluorobutyl acrylate (HFBA, 3d), benzyl acrylate (BnA, 3e), dodecyl acrylate (3f), carboxyethyl acrylate (CEA, 3g) in presence of 0.5 mol % of VBbpdpo (4), 1 mol % copper(II) acetate and 5 mol % mannose following the protocol described in Example 1 and 2 for photo-initiated polymerization at 3° C.

Chart 4. Acrylate monomers 3a-g

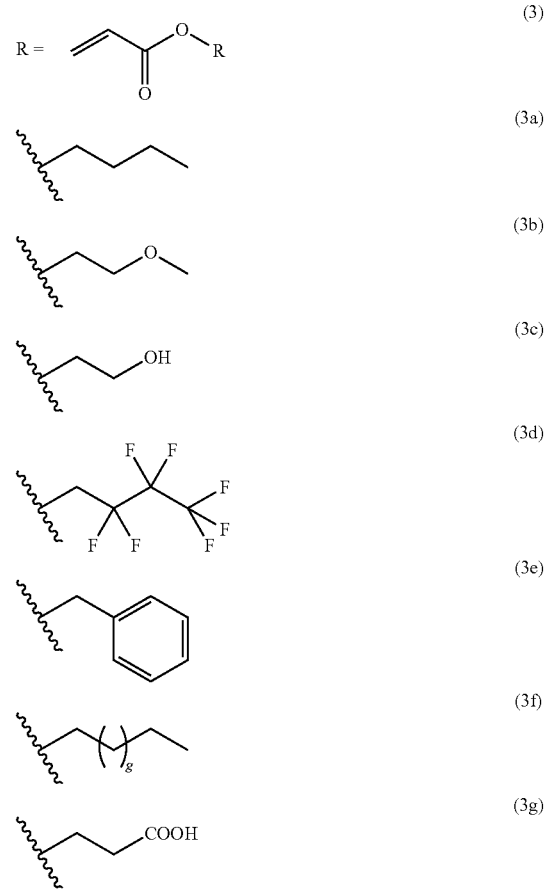

Chart 5. Ligand VB(dpdpo)

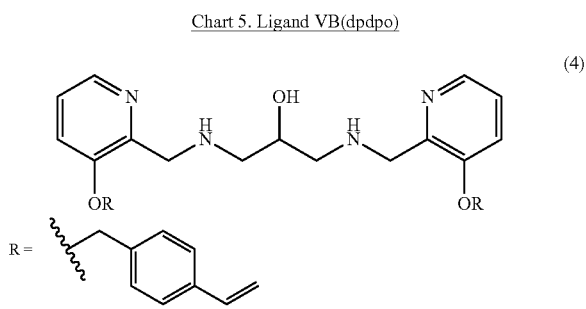

(4)

Figure 22:
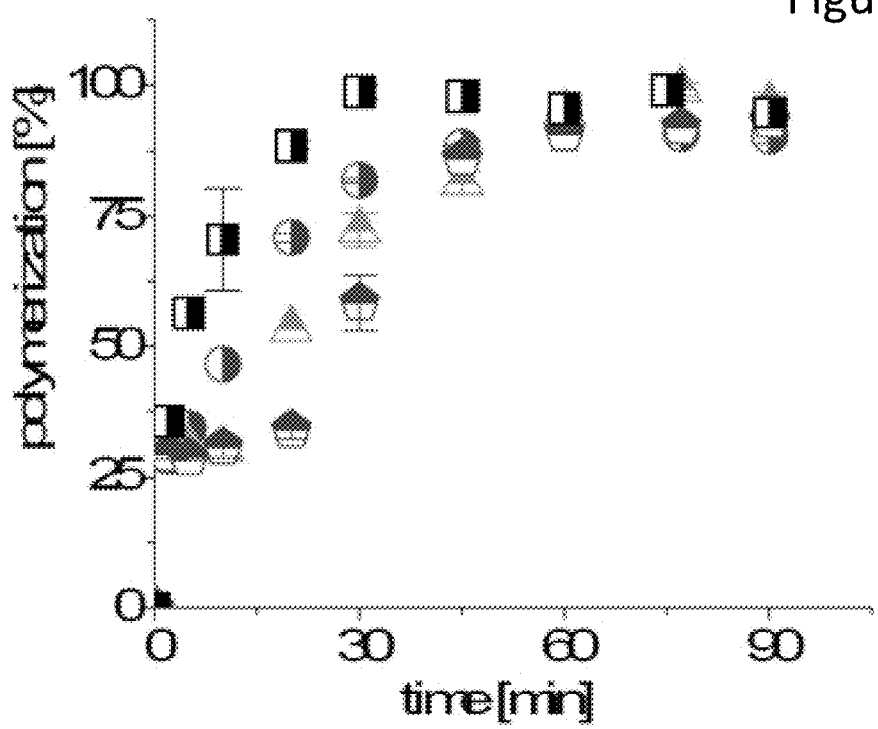
FIG. 22 shows gravimetric analysis of polymerization proceedings for microgels derived from 60 mol % EGDMA, 20 mol % BA, and 20 mol % BA (3a. ※), MEA (3b, ※), BnA (3e, ※), and CEA (3g, ※) co-monomers.

All polymerizations were carried out in presence of 60 mol % EGDMA crosslinking agent, 20 mol % BA, 20 mol % co-monomer and 1 mol % styrene or 0.5 mol % of ligand (4) in 52 mM SDS/CAPS buffer solution at pH 10.50.30-31 The gravimetric analyses of the polymerization proceedings reveal a slightly faster progression of the initial polymerization when polar co-monomers CEA (3g) and MEA (3b) are used in comparison to microgel formulations in presence of BA (3a) or BnA (3e) (FIG. 22). All reactions near completion close to 60 min and reach 95% on average independently of the co-monomers used. Initial attempts to analyze the synthesized microgels using IR and $^1$H NMR spectroscopy were futile and did not provide evidence for the incorporation of the co-monomers.

However, combustion data of microgels, purified by dialysis, reveal near quantitative incorporation of the co-monomers and the polymerizable ligand VBbpdpo (4) that builds the backbone of the catalytic center after activation of the dormant catalyst with Cu(II) ions (Table 4). An analysis of the microgels by dynamic light scattering suggests for all particles hydrodynamic diameters $D_h$ bet between 243 and 283 nm, monomodal distributions, and moderate dispersity. Correlations between the polarity of the co-monomer and the resulting particle sizes are not apparent.

The data are given as an average of combustion analyses of duplicate microgel formulations; the microgels are derived from 60 mol % EGDMA, 0.5 mol % VBbpdpo (4), 20 mol % BA, and 20 mol % of selected co-monomer.

3.2 Evaluation of the Catalytic Performance of the Microgels in Dependence of their Matrix Composition.

Figure 24:
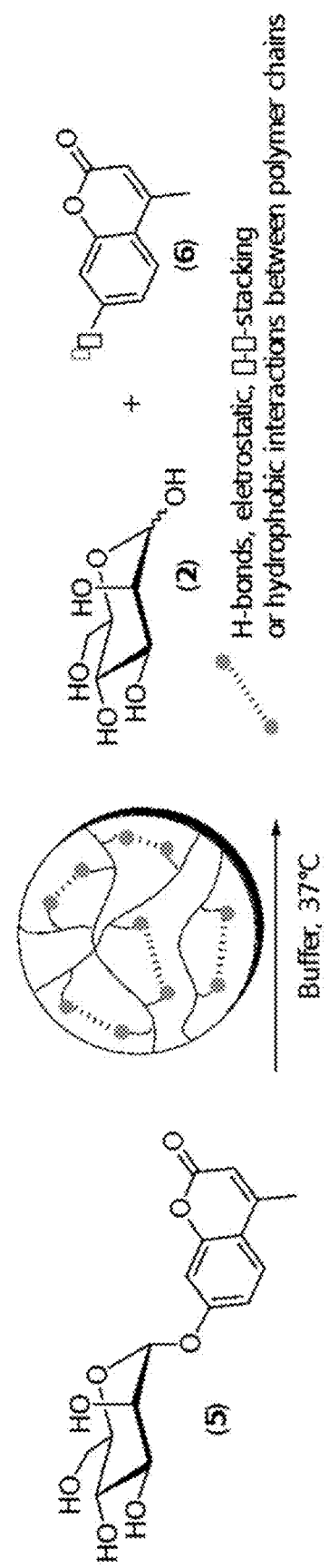
FIG. 24 shows catalyst screening by monitoring the hydrolysis of 4-methylumbelliferyl α-D-mannopyranoside using microgel catalysts with altered matrix composition.

The catalytic proficiency of microgels with altered matrix composition was determined using the hydrolysis of 4-methylumbelliferyl-α-D-mannopyranoside (5) as model substrate yielding mannose (2) and 4-methylumbelliferone (6) in 50 mM HEPES buffer at pH 7.0 (FIG. 24). The ease of hydrolysis of the α-mannoside renders this substrate ideal for fast catalyst screening in 96-well plate assays. The kinetic parameters for the rate constant ($k_{cat}$) and Michaelis-Menten constants ($K_M$) were determined by standard procedures as described above and the catalytic efficiency and proficiency of the microgels were derived therefrom (Table 5).

While the apparent rate constants for the microgel-catalyzed hydrolyses of substrate 5 are fairly similar, the corresponding Michaelis-Menten constants reveal different binding affinities between 5 and the respective microgels that differ up to one order of magnitude (Table 5, entries 1&5). Due to these differences, a 5-fold higher catalytic proficiency results for matrices incorporating 20 mol % of MEA 3b in place of BA 3a. This observation indicates strong stabilizing interactions between the MEA monomer and substrate 5 during the transition state of the glycoside hydrolysis and verifies the underlying hypothesis of this work. Given the free hydroxyl groups in the glycon of 5, H-bond accepting interactions of 3b were attributed to cause the observed stabilization of the glycoside during its hydrolysis. Similar interactions of 5 with the monomers in the matrix are noted for microgels containing hydroxyethyl acrylate 3c although to a much lesser extent. By contrast, the catalytic proficiency of microgels derived from acrylates 3d-g is within experimental errors similar to that of microgels derived from 3a only. This observation indicates a lack of significant additional interactions by 3d-g over 3a that would stabilize the selected glycoside during its hydrolysis by the microgel catalyst. However, H-bond accepting interactions could be also promoted by the highly fluorinated monomer 3d, yet the performance of the corresponding microgel catalyst is not very different from that of the microgel prepared with 3a.

Figure 23:
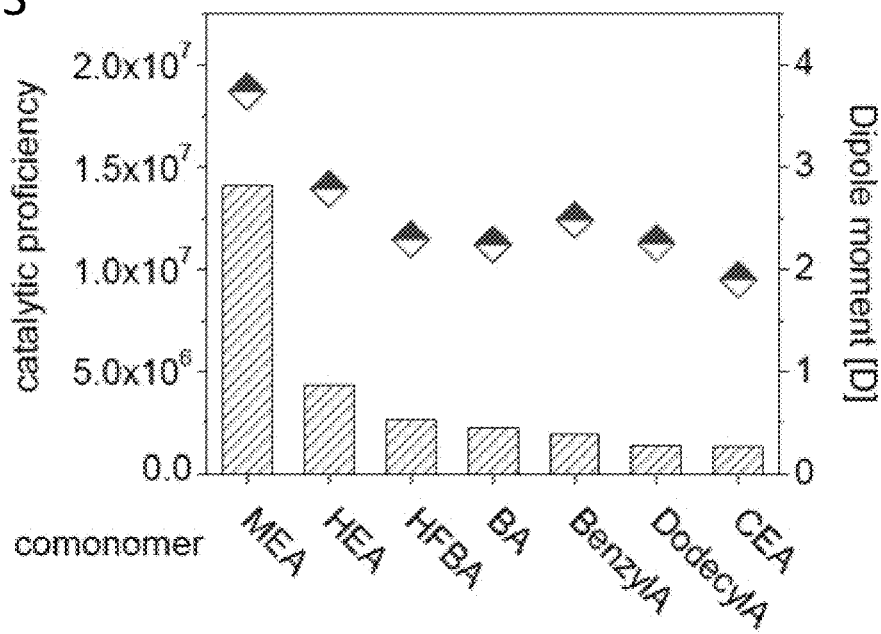
FIG. 23 shows catalytic proficiency (orange bars) of selected microgels and dipole moments (green diamonds) of corresponding co-monomers during the hydrolysis of 5 in 50 mM HEPES buffer at pH 7.00 and 37° C.

Therefore, we calculated the dipole moments of all monomers 3a-g in aqueous solution with density functional theory (DFT) employing the continuous solvation model (COSMO) for water, the B3LYP functional, and the 6-31+G(d) basis set. [Takano, Y et al. J. Chem. Theory Comput. 2005, 1, 70-77; Klamt 1993; Parallel Quantum Solutions] All computations were performed with the PQSmol suite yielding low energy conformers of the monomers at 298.15 K and 1 atm.41 Vibrational analyses confirmed the energy minima of the computed structures with zero imaginary frequency. The dipole moments of MEA and HEA are notably higher than those of all other monomers and correlate well with the increased catalytic proficiency of the corresponding microgels (FIG. 23).

Figure 25:
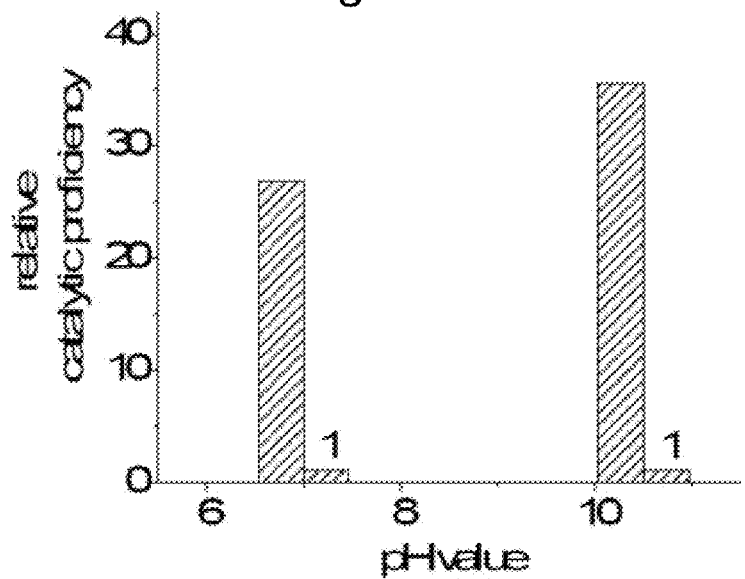
FIG. 25 shows catalytic proficiency of a microgel with 20 mol % CEA at pH 7.00 and 10.50 and 37° C. relative to $Cu_2$bpdpo.

Given the apparent correlation between catalytic proficiency and dipole moment of the co-monomers, we calculated the dipole moment of the sodium salt of CEA as 6.2. Consequently, a CEA containing microgel should show in alkaline solution a catalytic proficiency that is higher than that of a microgel with BA only. As the dissociation constant of CEA in water is to the best of our knowledge not reported, we used the structural similarity between CEA and propionic acid to predict the pKa value of CEA as 4.9.42 We then projected the pKa value of a linear CEA-polymer as 5.6, and estimated the pKa value of a crosslinked microgel with 20 mol % of CEA as 10.1 following the method by Fisher and Kunin as described.43 In short, the apparent pKa values of crosslinked microgels were estimated from the pKa(m=1) value of a linear polymer of the monomeric acid as eq 2

$$pK_{a,app} = pK_{a(m=1)}(2-m) \qquad (eq\ 2)$$

where m is the mol fraction of the monomeric acid. The dissociation constant of the linear polymer is estimated graphically by extrapolation. [Fisher, S. et al. J. Phys. Chem. 1956, 60, 1030-1032] We subsequently determined the catalytic performance of all microgels in 50 mM CAPS buffer at pH 10.50 (Table 3). The alkaline conditions increase the amount of deprotonated CEA monomer from less than 1% at pH 7.00 to more than 71% at pH 10.50. As the uncatalyzed hydrolysis of substrate 5 increases by the change of conditions 150-fold as well, the resulting catalytic proficiencies of the microgel catalysts decrease overall. For a fair comparison of catalytic performances under different conditions, we thus calculated the catalytic proficiencies relative to their low molecular weight complex $Cu_2bpdpo$ (1) (FIG. 25).

Under alkaline conditions, the catalytic proficiency of the microgels increases to 36 relative to the performance of complex $Cu_2bpdpo$ (1), whereas it was only 27-fold higher at neutral pH. However, the corresponding MEA-containing microgel has a 275-fold higher relative catalytic proficiency than $Cu_2bpdpo$ (Table 2, entry 1) rendering the incorporation of CEA in microgels to increase the catalytic turnover during glycoside hydrolyses under these conditions less efficient.

3.4 Conclusions.

A selection of mannose-templated polymers with 60 mol % of crosslinking content was synthesized embedding equal molar amounts of butyl acrylate and supplementary acrylate comonomers. The co-monomers introduced secondary interactions in the microgel matrix, such as H-bond donating and accepting, hydrophobic, π-π stacking, and electrostatic interactions. The obtained microgels were then evaluated for their ability to enhance the hydrolysis of glycosidic bonds in neutral and alkaline solution.

The catalytic proficiency of the resulting microgels was notably enhanced in neutral solution in presence of 20 mol % of MEA comonomer (3b) reaching $1.4 \times 10^7$, and to some smaller extend by HEA (3c). A contribution to the hydrolysis of glycosidic bonds by all other assessed co-monomers 3d-3g was not apparent under these conditions and close to the performance of the standard, i.e. the microgel prepared from butyl acrylate (3a) monomer only. This observation correlates well with the calculated dipole moments of the co-monomers and their H-bond accepting ability. By contrast, contributions of electrostatic interactions promoted by a CEA-containing microgel are only apparent in highly alkaline solutions reflecting the increased pKa value of a protic monomer in a crosslinked matrix. 43

Example 4: Evaluation of Antimicrobial Activity

A) Synthesis and Characterization of Antimicrobial Microgels

CAPS/SDS buffer. Typically, 0.221 g (1.00 mmol) of CAPS were dissolved in nanopure water. The resulting solution was titrated with aqueous sodium hydroxide solution to pH 10.08 at 23° C. and adjusted to a volume of 200 mL translating into a buffer solution with a pH of 10.50 at 0° C. Then, sodium dodecyl sulfate (3.0000 g, 10.403 mmol) was dissolved in a portion of this CAPS buffer solution to yield 200.00 g of an aqueous SDS/CAPS buffer solution that is approximately 5 mM in CAPS and 52 mM in SDS. The buffer solution was stored at ambient temperature until use.

VBbpdpo ligand stock solution. Typically, 0.1352 g (252.1 µmol) of VBbpdpo ligand were dissolved in 3.1664 g of DMSO. Then, a 0.1176 g portion of the resulting solution was used for microgel synthesis corresponding to 8.980 µmol of VBbpdpo per microgel disperson.

Copper(II) acetate stock solution. Typically, 0.1749 g (874.5 µmol) of copper(II) acetate were dissolved in 5 mL nanopure water. The 175 mM stock solution was kept at ambient temperature and used in 100 µL aliquots.

Initiator stock solution. Typically, 0.2189 g (854.1 µmol) of 2,2'-dimethoxy-2-phenylacetophenone were dissolved in 900 µL of methanol immediately prior to use.

Pre-polymerization mixture. In a typical experiment, 0.2088 g (1.053 mmol) of EGDMA, 0.0923 g (7.20 mmol) butyl acrylate, and 0.1172 g of ligand solution were mixed. Then, 9.6082 g of the 5 mM CAPS/52 mM SDS solution and 0.0812 g of decane were added. The resulting mixture was stirred for 2 min prior to addition of 100 µL of the aqueous copper(II) stock solution. The resulting mixture was then stirred for 15 h at ambient temperature. After ice cooling for 15 min, the mixture was sonicated over 2 min (40% amplitude, 5 s pulse on, 2 s pulse off). Lastly, 25.25 mg (94.46 µmol) of galactonoamidine (1) were added to the pre-polymerization mixture in the cold.

Polymerization protocol. After 30 min, a 0.2 ml aliquot of the initiator stock solution was added and the reaction mixture immediately placed under UV light to initiate the polymerization. All reaction mixtures were stirred and kept in an ice-bath to ensure a temperature of 3° C. or below during the polymerization over 60 min. Additionally, microgels $^{Cu2L}P_{gal}$ with crosslinking content between 5 and 80 mol % were prepared in presence of galactose as described. (Sharma/Striegler, Biomacromolecules 2018)

Elemental analysis. Following a previously disclosed protocol, all microgels were purified by dialysis against aqueous EDTA/SDS solution, SDS solution, and nanopure water, and then freeze-dried. Anal. Calcd for LP1 (60% EGDMA): C, 62.08; H, 7.81; N, 0.16. Found: C, 61.42; H, 7.86; N, 0.15. See, Example 2.

B) Evaluation of Microgels as Catalysts to Cleave Glycosidic Bonds in Model Compounds Related to Bacterial Cell Membranes Proof of concept for the catalytic activity of the microgels and their low molecular weight analog $Cu_2bpdpo$ towards hydrolysis of a model compound of the bacterial polysaccharide layer was obtained by evaluating the catalyzed hydrolysis of 4-methylumbelliferyl N-acetyl-β-D-glucosaminide in 50 mM HEPES buffer at pH 7.00.

Aqueous Solutions for Dialysis.

EDTANa$_2$/SDS solution. Typically, 6 g of sodium dodecylsulfate were added to a solution of 0.048 g of disodium ethylenediaminotetraacetate in 400 mL nanopure water.

SDS solution. Typically, 11.25 g of sodium dodecylsulfate were dissolved in 750 mL nanopure water.

CAPS/SDS solution. Typically, a 500 mL aliquot of a 50 mM CAPS buffer solution with a pH of 10.50 for an intended use at 37° C. was prepared by standard methods using 5.5 g of CAPS. A portion of this buffers solution was added to 5.25 g of SDS, and the weight of the resulting solution was kept at 350 g.

Catalyst Stock Solutions:

Stock solutions of microgels. Typically, 200 µL of the synthesized microgel solution were dialyzed at ambient temperature against aqueous EDTANa$_2$/SDS (2 h, 5×), SDS (1 h 10×) and CAPS/SDS solutions (2 h, 4×) in the specified cycles and times using dialysis membranes with a molecular weight cut-off of 15,000. Subsequently, the microgel dispersions were diluted with CAPS/SDS solution, followed by addition of appropriate aliquots of an aqueous Cu(II) acetate solution (10 mg in 5 mL nanopure water) and increased to a 2 mL volume by further addition of CAPS/SDS solution. The catalysts were used as such for all subsequent experiments; $^{Cu2L}P_{gal}$ (40%) 56.3 µM; $^{Cu2L}P_{gal}$ (60%) 72.8 µM; $^{Cu2L}P_1$ (60%) 76.8 µM Stock solution of Cu2bpdpo. Typically, 3.65 mg (5.56 µmol) of Cu$_2$bpdpo were dissolved in 5 mL of nanopure water yielding a 1.11 mM stock solution of the catalyst.

Substrate stock solution. Typically, 18.92 mg (49.87 µmol) of 4-methylumbelliferyl-N-acetyl-β-D-gluconoaminide were dissolved in 1000 µL of DMSO and diluted to 10 mL with 50 mM HEPES buffer yielding a 4.99 mM substrate stock solution. The solution was kept in a warm water bath until use.

Kinetic assay. Typically, 0-175 µL aliquots of the substrate stock solution were added to 20 µL of a catalyst stock solution and corresponding aliquots of buffer solution in 96-well plates yielding 200 µL of the respective reaction mixture. The formation of 4-methylumbelliferone was monitored by fluorescence spectroscopy ($\lambda_{ex}$=360 nm; $\lambda_{ex}$=465 nm) at 37° C. over 8 h. Fluorescence data collected between 60 and 260 min were used for analysis. For control reactions, the amount of catalyst stock solution was substituted by buffer solution.

Data analysis. The collected fluorescence data were transformed in concentrations using apparent extinction coefficients determined in presence of each microgels solution separately. The obtained concentration was plotted over time to deduce the rate of the reaction. The deduced rates were plotted over substrate concentration to yield hyperbolic data that were analyzed using the Michaelis-Menten model to yield kinetic parameters of the respective reaction. The catalytic proficiency of the catalysts was calculated from these values using standard methods. The normalized catalytic proficiency was obtained by correlating the catalytic proficiency of the microgels to that of the low molecular weight complex Cu2bpdpo.

Figure 26A:
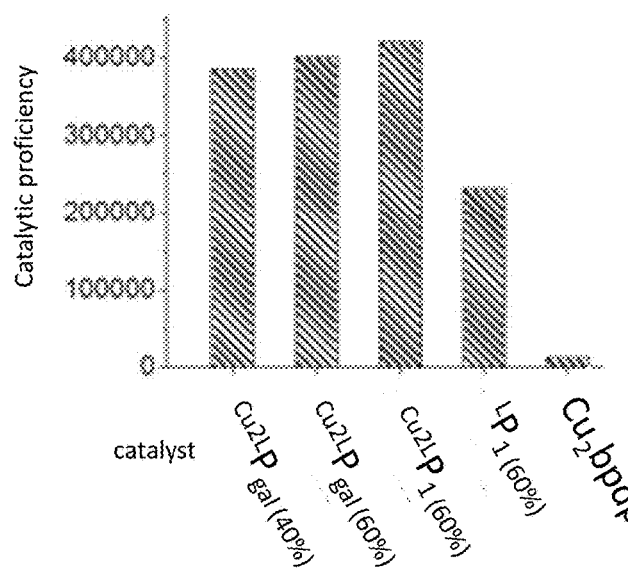
FIGS. 26A-26B show catalytic proficiency of microgels and copper(II) complex $Cu_2$bpdpo toward the hydrolysis of 4-methylumbelliferyl N-acetyl-β-D-glucosaminide in (FIG. 26A) absolute, and (FIG. 26B) relative values. The template is given as suffix and the crosslinking content in brackets.
Figure 26B:
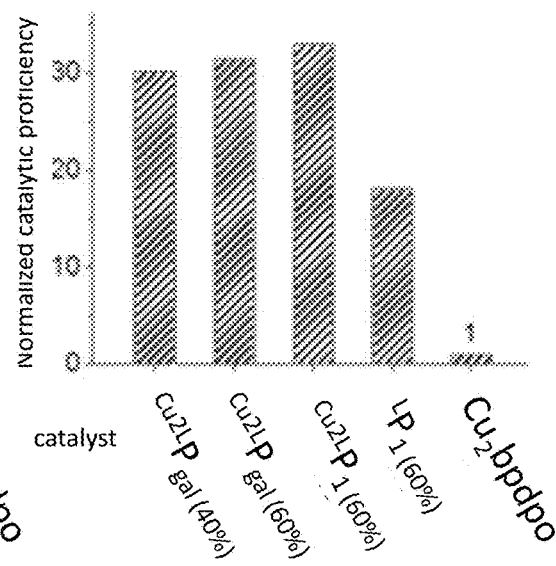

Results: The data reveal increased catalytic activity of the microgels after activation with Cu(II) ions over the metal free catalyst or the low molecular weight analog $Cu_2bpdpo$. The data disclose highest proficiency for a microgel prepared in presence of galactonoamidine (1) $^{Cu2L}P_1$ (60%), that is about 35-fold higher than that of the low molecular weight complex $Cu_2bpdpo$. (FIGS. 26A-26B)

C) Evaluation of Microgels as Antimicrobial Entities Towards Growth of *E. coli* Cells in 96-Well Plate Assays Using UV/Vis Spectroscopy

*E. coli* cell culture. A 1000 µL aliquot of B21DE3 *E. coli* cells, purchased from New England Biolabs, was added to 10 mL of sterile Luria-Bertani broth (Miller's media); the culture was incubated for 6 h at 37° C., and an aliquot of the culture was diluted 200,000-fold with media for further analysis and immediate use.

Stock solution of low molecular weight complex Cu2bpdpo (catalyst 1). In a typical experiment, 3.65 mg of $Cu_2bpdpo$ were dissolved in 5 mL of 50 mM HEPES buffer at pH 7.00; a 130 µl aliquot of the resulting solution was further diluted into 2 mL yielding a 72.3 µM stock solution of $Cu_2bpdpo$.

Stock solution of Hen Egg-white lysozyme (catalyst 2). In a typical experiment, 4.90 mg of lyophilized lysozyme purchased from AMRESCO were dissolved in 5 mL of 50 mM HEPES buffer at pH 7.00 and used as a 68.5 µM stock solution.

Stock solutions of microgels prepared in presence of galactose and 40% EGDMA ($^{Cu2L}P_{gal}$ (40%))—catalyst 3). See described general protocol above; the resulting microgel stock solution after 1:10 dilution during activation is 56.2 µM.

Stock solutions of microgels prepared in presence of galactose and 60% EGDMA ($^{Cu2L}P_{gal}$ (60%))—catalyst 4). See described general protocol above; the microgel stock solution after 1:10 dilution during activation is 72.8 µM.

Stock solutions of microgels prepared in presence of galactonoamidine (1) ($^{Cu2L}P_{gal}$—catalyst 5). See described general protocol above. The synthesized microgels were dialyzed and the catalysts activated by addition of Cu(II) acetate as described (Sharma/Striegler Biomacromolecules 2018) resulting in a microgel stock solution that was used as is for the subsequent kinetic and inhibition of cell growth experiments; the microgel stock solution after 1:10 dilution during activation is 76.8 µM.

Kinetic assay. In a typical experiment, 25, 50 or 100 µL aliquots of the catalyst stock solutions were added to 100 µL of the cell culture in 96-well plates. The volume of all wells was adjusted to 200 µL by addition of aqueous buffer solution. The resulting catalyst concentrations were 38.4 µM, 19.2 µM and 9.6 µM, respectively.

The cell growth was monitored by UV/Vis spectroscopy at 595 nm at 37° C. over 20 h in 2 h cycles. For control experiments, the cell growth was monitored in absence of catalysts and corresponding amounts of catalyst solutions were substituted by buffer solution. Also, the absorbance of the catalysts solutions in absence of *E. coli* cells was determined for data correction. All experiments were performed in duplicate.

Figure 27:
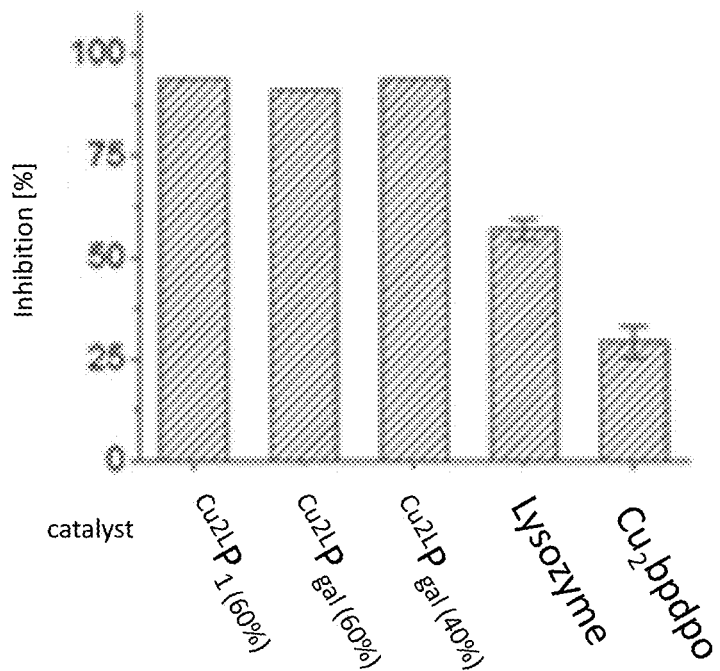
FIG. 27 shows inhibition activity of selected catalysts toward growth of E. coli cells observed by UV/Vis spectroscopy at 595 nm and 37° C. after 20 h.
Figure 28:
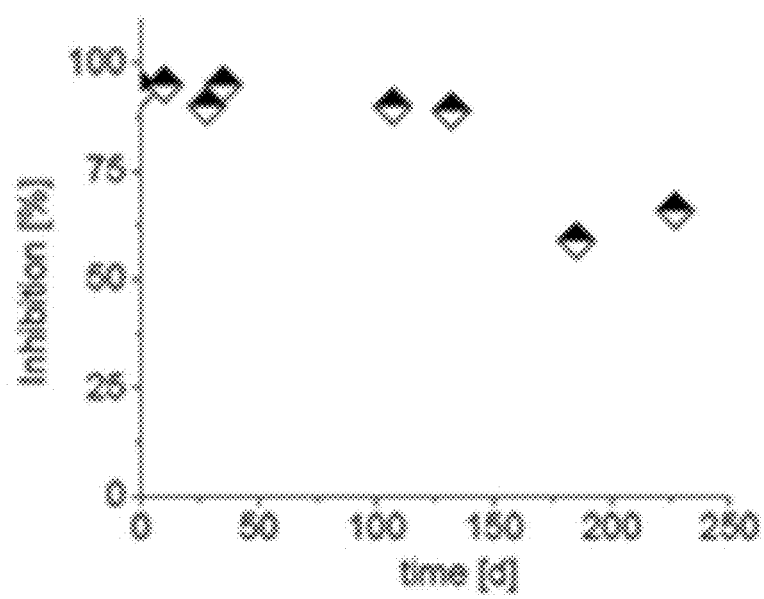
FIG. 28 shows inhibition activity of $^{Cu_2L}P_1$(60%) at 19.2 μM toward growth of E. coli cells dependence of time of catalyst activation; observed by UV/Vis spectroscopy at 595 nm and 37° C.

Data analysis. The collected absorbance changes were corrected for absorbance caused by the respective catalyst solution to yield absorbance data related to cell proliferation. The obtained data were then correlated to the cell growth in absence of catalysts and expressed in percent inhibition. (FIGS. 27-28)

D) Evaluation of Microgels as Antimicrobial Entities Towards Growth of *E. coli* Cells in Petridish Assays with Müller-Hinton/Agar Media Sterile Müller-Hinton/Agar (MH) media. 4.54 g Müller-Hinton media and 5.07 g agar were dissolved in 200 mL deionized water. The media were autoclaved and stored at 4° C. until use.

*E. coli* cell culture. A 100 µL aliquot of B21 DE3 *E. coli* cells, purchased from New England Biolabs, were added to 1 mL of sterile Luria-Bertani broth; the culture was incubated for 2 hours at 37° C. Then, a 100 µL aliquot of this culture was diluted by serial dilution 200,000-fold with sterile LB (Miller's) media yielding 10 mL of a stock solution of the cell culture.

Catalysts.

Stock solution of low molecular weight complex $Cu_2bpdpo$ (catalyst 1). 5.28 mg of $Cu_2bpdpo$ were dissolved in 5 mL of 50 mM HEPES buffer at pH 7.00; a 1000 µl aliquot of the resulting solution was further diluted into 10 mL yielding a 160.3 µM stock solution of $Cu_2bpdpo$.

Stock solution of Hen Egg-white lysozyme (catalyst 2). 11.53 mg of lyophilized lysozyme purchased from AMRESCO were dissolved in 5 mL of 50 mM HEPES buffer at pH 7.00 and used as a 161.1 µM stock solution.

Stock solutions of microgels (catalysts 3-5). All microgel stock solutions were treated as described above, but only diluted 1:5 during activation and then sterilized prior to use for these experiments. The stock solution for $^{Cu2L}P_{gal}$ (40%) is 112.3 µM, for $^{Cu2L}P_{gal}$ (60%) 145.6 µM and for $^{Cu2L}P_1$ (60%) 153.6 µM.

Plate preparation. In a typical set of experiments, 10 mL media were poured into a sterile 6 cm petri dish and allowed to solidify. A 700 µL aliquot of each catalyst stock solution was added to 100 µL of stock solution of *E. coli* cells and mixed. Then, a 50 µL aliquot of the resulting catalyst-cell mixture was added onto a Müller-Hinton agar plate and spread. The plate was incubated at 37° C. over a 12 h time period. The cell growth was documented with images of the plates in 1 h time intervals.

Results. The plates treated with microgel show strong inhibition of cell growth of *E. coli*, while plates with lysozyme, $Cu_2bpdpo$ or without catalyst addition show inhibition of cell growth to a much smaller extend. (FIGS. 29A-29F)

Example 5: Evaluation of the Minimum Inhibitory Concentration of Various Microgels As demonstrated in the results below, the antimicrobial activity of the gels depends on the crosslinking content of the material, the template, the metal complex, and the surfactant used during material preparation.

Experimental Methods and Preparation of Reagents and Cell Growth:

The minimal inhibitory concentration (MIC) and minimal bactericidal concentration (MBC) by broth microdilution assays in 96-well plates to determine antimicrobial activity of selected agents against Gram-positive and Gram-negative bacteria Antimicrobial materials: In a typical experiment, the synthesized polymers were prepared for antimicrobial assays as described for the kinetic assays in Example 4(A), except as indicated in Tables 7-10 and 12.

Mueller Hinton broth (MHB): A sterile broth is prepared with 4.50 g Mueller Hinton base (Hardy Diagnostics) in 200 mL deionized water. The broth is cooled to room temperature after being autoclaved and stored at 4° C. until use.

Mueller Hinton agar (MHA): A sterile agar is prepared from 4.50 g Mueller Hinton base (Hardy Diagnostics) and 5.00 g agar (Sigma) in 200 mL deionized water. The agar is cooled to ambient temperature after being autoclaved and stored at 4° C. until use.

Propagation of bacterial cells: Typically, 500 µL aliquots of S. aureus (ATCC® 25923™) or E. coli (BL21 DE3) cells are used to inoculate 5 mL of Mueller Hinton broth. The inoculum is shaken at 37° C. and 240 rpm for 6 h. Then, 500 µL aliquots are transferred to individual vessels, flash-frozen in liquid nitrogen, and stored as pre-starter cultures at −20° C. until use.

Growth of bacterial cells: A 500 µL pre-starter culture is used to inoculate 5 mL of Mueller Hinton broth at 37° C. After 5 h of shaking at 240 rpm, a 500 µL of the inoculum is diluted to 20 mL with sterile MHB, followed by three successive 1:10 dilutions of 1000 µL of the resulting solutions into 10 mL MHB. Subsequently, 50 µL of the most dilute cell suspension is spread on a Mueller-Hinton agar plate, and incubated at 37° C. After 24 h, selected colonies are re-suspended in 4 mL of Mueller-Hinton broth and diluted until their $OD_{625}$ value matched that of a 0.5 McFarland standard at 37° C. to account for a cell concentration of $1 \times 10^8$ CFU/mL. Typically, a 50 µL aliquot of the cell suspension is diluted into 10 mL of Mueller-Hinton broth to obtain a stock solution of S. aureus cells at a concentration of $5 \times 10^5$ CFU/mL. Typically, two separate inoculums are prepared immediately prior to use.

Preparation of broth microdilution assays and data recording: Following standard procedures for conducting broth microdilution assays, 100 µL aliquots of Mueller-Hinton broth are added to each well. Subsequently, a 100 µL aliquot of the sterile antimicrobial agent solution is added in the first column of the plate and then diluted in a serial manner by subsequent transfers of 100 µL aliquots over the first 10 columns. Finally, 100 µL of the prepared cells are added to the first 11 columns leaving the last column without antimicrobial agents are 32, 16, 8, 4, 2, 1, 0.5, 0.25, 0.125. and 0.0625 µg/mL, while the cell concentration is $2.5 \times 10^5$ CFU/mL. Typically, the absorbance in each well is then monitored at 595 nm and 37° C. over a 16 h period in 2 h intervals.

Data analysis: The obtained absorbance data are plotted against time to determine the steady state point of cell growth. The change of absorbance at this time for wells with and without antimicrobial agent is then plotted against the concentration of the antimicrobial agent. Linear extrapolation of the data determines the minimal inhibitory concentration (MIC).

Evaluation of bacteriostatic and bactericidal properties of antimicrobial agents: For each antimicrobial agent, 50 µL aliquots of the wells of the 96-well plates with concentrations higher than the MIC value are used to inoculate Mueller-Hinton agar plates. The plates are incubated at 37° C. and examined after 24 h by the naked eye. Visible cell growth indicates bacteriostatic and absence of cell growth bactericidal properties of the evaluated agents at the chosen concentration.

Results and Discussion

Table 7 shows the antimicrobial activity of the microgels with varying crosslinking content. The MIC improves (decreases) with increasing crosslinking content of the material, but levels out for microgels prepared from 60% of EGDMA (ethyleneglycol dimethacrylate crosslinker).

Table 8 shows the antimicrobial activity of the microgels prepared with different temples. The choice of template affects the MIC and is maximized when strongly coordinating anions are used as templates, e.g. galactonoamidines. The activity remains noticeable when using strongly coordinating sugar anions or polyalcohols during material synthesis.

Table 9 shows the antimicrobial activity prepared with different ligand monomers. The MIC of the microgels depends on the metal complex used during material preparation and correlates to the Cu(II) coordination ability of the multidentate ligand in the gels.

When SDS is used as a surfactant during material preparation (Tables 7-9), the minimum bactericidal concentration of all microgels is 1 µg/mL for S. aureus, and larger than 32 µg/mL for E. coli. When using non-ionic surfactants during material synthesis, the minimum bactericidal concentration of all microgels is above 32 µg/mL.

Table 10 shows the antimicrobial activity prepared with different HLB (hydrophilic-lipophilic balance) value. The antimicrobial activity of the microgels depends on the HLB value when non-ionic surfactants are used during material synthesis and is maximized when the particle diameter is minimized for a given particle composition, e.g. EGDMA/BA 60/40, mannose template, VBbpdpo ligand, Cu(II) ions, and TWEEN/SPAN 80/80 mixtures to achieve HLB 8, 12 and 15. The minimum bactericidal concentration (MBC) for all polymers is ≥32 µg/mL.

Table 11 summarizes several control experiments. The antimicrobial activity of the microgel suspensions is not caused by the surfactant or surfactant buffer mixture and not solely related to the immobilized metal complex. Instead, the antimicrobial activity is ascribed to a synergy of matrix effects and metal complex activity due to the lower activity obtained for the separate components. Each of entries 1-3 have a MIC greater than 120 µg/mL for S. aureus and 260 m/mL for E. coli.

Table 11 also shows the antimicrobial activity of several antimicrobial agents. The observed activity of the best polymeric antimicrobial agent outperforms currently available low molecular weight antimicrobial agents against S. aureus, such as vancomycin, chloramphenicol, and benzalkonium chloride, 6 to 15-fold.

Table 12 show a time-dependent analysis of selected microgels with a matrix composition of EGDMA/BA=60/40 prepared from the specified ligand, template, Cu(II) ions and SDS surfactant. These microgels maintained activity over at least 4 months with no noticeable decrease in activity.

TABLES

TABLE 1

Kinetic Parameters for the Catalytic Hydrolysis of 4-Methylumbelliferyl-β-D-galactopyranoside[a]

| Entry | Catalyst | $k_{cat} \times 10^{-6}$ (min$^{-1}$) | $K_M$ (mM) | $k_{cat}/K_M$ (min$^{-1}$ M$^{-1}$) | $k_{cat}/k_{non}$ (M) | $k_{cat}/(k_{non} \times K_M)$ |
|---|---|---|---|---|---|---|
| 1 | $^{Cu2L}P_{gal}$ | 360 ± 80 | 5.68 ± 1.44 | 0.0634 | 1250 | 220000 |
| 2 | $^{Cu2L}P_{EG}$ | | | 0.394 | | 137000 |
| 3 | $^{L}P_{gal}$ | | | 0.0254 | | 88000 |
| 4 | Cu$_2$bpdpo (2) | 7.2 ± 2.20 | 4.27 ± 1.5 | 0.0017 | 25 | 5800 |

[a]pH 10.50 in aqueous 50 mM CAPS buffer solution at 37° C.; $k_{non}(6) = 2.88 \times 10^{-7}$ min$^{-1}$ M$^{-1}$.

TABLE 2

Kinetic Parameters for the Catalyzed Hydrolyses of α-9 and β-9 in 50 mM Aqueous CAPS Buffer[a]

| Entry | S | Catalyst | EGDMA (%) | $k_{cat}$ (10$^{-3}$ min$^{-1}$) | $K_M$ (mM) | $k_{cat}/K_M$ (min$^{-1}$ M$^{-1}$) | $k_{cat}/(k_{non} \times K_M)$ |
|---|---|---|---|---|---|---|---|
| 1 | α-9 | Cu$_2$bpdpo | | 0.000370 ± 0.000067 | 3.7 ± 0.11 | 0.000100 | 22200 |
| 2 | | $^{Cu2L}P_{gal}$ | 5 | 0.00725 ± 0.00059 | 2.61 ± 0.38 | 0.00278 | 617000 |
| 3 | | | 25 | 0.00113 ± 0.00014 | 0.320 ± 0.03 | 0.00354 | 787000 |
| 4 | | | 40 | 0.00613 ± 0.00056 | 1.68 ± 0.23 | 0.00373 | 818000 |
| 5 | | | 60 | 0.0200 ± 0.00010 | 6.27 ± 0.59 | 0.00319 | 709000 |
| 6 | | | 80 | 0.00737 ± 0.00261 | 4.34 ± 0.23 | 0.00170 | 378000 |
| 7 | | $^{Cu2L}P_1$ | 60 | 0.0100 ± 0.00149 | 1.84 ± 0.12 | 0.00544 | 1210000 |
| 9 | β-9 | Cu$_2$bpdpo | | 0.00717 ± 0.00021 | 4.27 ± 0.15 | 0.00168 | 5830 |
| 10 | | $^{Cu2L}P_{gal}$ | 5 | 0.310 ± 0.008 | 5.57 ± 0.18 | 0.0557 | 193000 |
| 11 | | | 25 | 0.480 ± 0.002 | 6.29 ± 0.34 | 0.0763 | 265000 |
| 12 | | | 40 | 0.320 ± 0.004 | 3.76 ± 0.54 | 0.0851 | 295000 |
| 13 | | | 60 | 0.360 ± 0.008 | 5.68 ± 0.14 | 0.0634 | 220000 |
| 14 | | | 80 | 0.190 ± 0.002 | 3.88 ± 0.61 | 0.0490 | 139000 |
| 15 | | $^{Cu2L}P_1$ | 60 | 0.138 ± 0.015 | 1.48 ± 0.20 | 0.0946 | 328000 |
| 16 | | β-galactosidase | | 2.95 ± 0.09 | 0.54 ± 0.06 | 5.46 | 19000000 |

[a]$k_{non}$(α-9) = 4.50 × 10$^{-9}$ min$^{-1}$ M$^{-1}$; $k_{non}$(β-9) = 2.88 × 10$^{-7}$ min$^{-1}$ M$^{-1}$, pH 10.50 and 37° C.

TABLE 3

Kinetic Parameters for the Catalyzed Hydrolysis of β-9 in 5 mM Aqueous HEPES Buffer, at pH 7.00 and 37° C.[a]

| Entry | Catalyst | IC$_{50}$ (μM) | $K_i$ (nM) | $k_{cat}$ (min$^{-1}$) | $K_M$ (mM) | $K_{TS}$ (=$K_M \times k_{non}/k_{cat}$) |
|---|---|---|---|---|---|---|
| 1 | $^{Cu2L}P_1$ | 3200 | (1.00 ± 0.033) × 10$^5$ | (3.0 ± 0.2) × 10$^{-5}$ | 2.5 ± 0.6 | 1.1 × 10$^{-7}$ |
| 2 | β-galactosidase | 0.3 | 0.160 ± 0.040 | 4.6 ± 0.1 | 0.11 ± 0.22 | 3.1 × 10$^{-14}$ |

[a]$k_{non}$(β-9) = (1.3 ± 0.2) × 10$^{-9}$ min$^{-1}$ M$^{-1}$, 5 mM HEPES buffer, pH 7.00

TABLE 4

Combustion data of microgels $^{L}P_{man}$ and resulting concentrations of VBbpdpo.

| Entry | Co-Monomer | $C_{expected}$ [%] | $C_{found}$ [%] | $H_{expected}$ [%] | $H_{found}$ [%] | $N_{expected}$ [%] | $N_{found}$ [%] | VBbpdpo [mM] |
|---|---|---|---|---|---|---|---|---|
| 1 | BA (3a) | 62.28 | 62.00 | 7.81 | 7.80 | 0.16 | 0.15 | 0.70 |
| 2 | MEA (3b) | 60.75 | 60.32 ± 0.01 | 7.49 | 7.50 ± 0.02 | 0.16 | 0.16 ± 0.03 | 0.79 |
| 3 | HEA (3c) | 60.34 | 59.69 ± 0.05 | 7.38 | 7.18 ± 0.06 | 0.16 | 0.17 ± 0.7 | 0.84 |
| 4 | HFBA (3d) | 54.36 | 55.15 ± 0.07 | 6.05 | 6.06 ± 0.06 | 0.14 | 0.15 ± 0.04 | 0.87 |
| 5 | BnA (3e) | 63.93 | 63.49 ± 0.08 | 7.22 | 7.13 ± 0.07 | 0.16 | 0.16 ± 0.06 | 0.89 |
| 6 | DodecylA (3f) | 64.96 | 64.41 ± 0.06 | 8.49 | 8.59 ± 0.05 | 0.14 | 0.16 ± 0.04 | 0.88 |
| 7 | CEA (3g) | 60.34 | 59.49 ± 0.08 | 7.38 | 7.42 ± 0.07 | 0.16 | 0.15 ± 0.3 | 0.78 |

TABLE 5

Kinetic parameter for the hydrolysis of (5) catalyzed by microgels containing different co-monomers and Cu$_2$bpdpo (1) in 50 mM HEPES buffer, pH 7.00 and 37° C.

| Entry | Co-monomer | $k_{cat}$ ($10^{-5}$ min$^{-1}$) | $K_M$ (mM) | $k_{cat}/K_M$ (min$^{-1}$ M$^{-1}$) | $k_{cat}/(k_{non} \times K_M)$ |
|---|---|---|---|---|---|
| 1 | MEA | 5.0 ± 0.4 | 0.46 ± 0.01 | 0.11 | 14,000,000 |
| 2 | HEA | 8.0 ± 0.3 | 2.40 ± 0.02 | 0.033 | 4,300,000 |
| 3 | HFBA | 5.0 ± 0.3 | 2.41 ± 0.04 | 0.021 | 2,700,000 |
| 6 | BA | 8.0 ± 0.2 | 4.51 ± 0.02 | 0.018 | 2,300,000 |
| 5 | BnA | 11 ± 0.2 | 7.43 ± 0.02 | 0.015 | 1,900,000 |
| 4 | DodecylA | 9.0 ± 0.3 | 8.47 ± 0.05 | 0.011 | 1,400,000 |
| 7 | CEA | 7.0 ± 0.5 | 6.64 ± 0.07 | 0.011 | 1,400,000 |
| 8 | Cu$_2$bpdpo | 0.36 ± 0.08 | 7.90 ± 0.90 | 0.00039 | 51,000 |

TABLE 6

Kinetic parameter for the catalyzed hydrolysis of 4MU-a man by microgels with different co-monomers in 50 mM CAPS buffer, pH 10.50 and 37° C.

| Entry | Co-monomer | $k_{cat}$ ($10^{-3}$ min$^{-1}$) | $K_M$ (mM) | $k_{cat}/K_M$ (min$^{-1}$ M$^{-1}$) | $k_{cat}/(k_{non} \times K_M)$ |
|---|---|---|---|---|---|
| 1 | MEA | 1.8 ± 0.10 | 6.1 ± 0.7 | 0.30 | 269,000 |
| 2 | CEA-No | 2.2 ± 0.20 | 8.2 ± 1.3 | 0.27 | 242,000 |
| 3 | HEA | 1.8 ± 0.07 | 6.8 ± 0.4 | 0.27 | 236,000 |
| 6 | BA | 2.2 ± 0.50 | 8.7 ± 0.9 | 0.26 | 232,000 |
| 5 | DodecylA | 2.0 ± 0.10 | 7.8 ± 0.5 | 0.26 | 230,000 |
| 4 | BnA | 2.5 ± 0.22 | 11.8 ± 1.0 | 0.21 | 187,000 |
| 7 | RFBA | 3.1 ± 0.43 | 17.2 ± 0.7 | 0.18 | 159,000 |

$k_{non}$ (1.13 × 10$^{-6}$ min$^{-1}$ M$^{-1}$); $k_{cat}/(k_{non} \times K_M)$ for Cu$_2$bpdpo = 6,800

TABLE 7

Minimum Inhibitory Concentration (MIC) of microgels depending on their crosslinking content

| Entry | EGDMA/BA mol/mol %/% | S. aureus MIC (µg/mL) | E. coli MIC (µg/mL) |
|---|---|---|---|
| 1 | 5/95 | 0.93 ± 0.01 | 3.29 ± 0.04 |
| 2 | 25/75 | 0.72 ± 0.01 | 3.11 ± 0.03 |
| 3 | 40/60 | 0.68 ± 0.02 | 2.73 ± 0.01 |
| 4 | 60/40 | 0.64 ± 0.01 | 2.27 ± 0.09 |
| 5 | 80/20 | 0.64 ± 0.01 | 2.17 ± 0.03 |

TABLE 8

Minimum inhibitory activity of microgels correlated to the template used during material synthesis

| Entry | template | S. aureus MIC (µg/mL) | E. coli MIC (µg/mL) |
|---|---|---|---|
| 1 | Ethylene glycol | 0.73 ± 0.02 | 2.60 ± 0.08 |
| 2 | mannose | 0.64 ± 0.01 | 2.27 ± 0.09 |
| 3 | N-benzylgalactonoamidine | 0.52 ± 0.01 | 2.15 ± 0.03 |

TABLE 9

Minimum inhibitory activity of microgels correlated to the template used during material synthesis

| Entry | Metal complex | MIC (µg/mL) S. aureus | MIC (µg/mL) E. coli |
|---|---|---|---|
| 1 | Cu$_2$VB(bsdpo) | 0.38 ± 0.01 | 1.56 ± 0.02 |
| 2 | CuVB(IDA) | 0.56 ± 0.02 | 1.62 ± 0.01 |
| 3 | Cu$_2$VB(bpdpo) | 0.64 ± 0.01 | 2.27 ± 0.09 |

TABLE 10

Minimum inhibitory activity of microgels correlated to the HLB value of the non-ionic surfactant mixture used during material synthesis

| Entry | HLB | Diameter [nm] | MIC (µg/mL) S. aureus | MIC (µg/mL) E. coli |
|---|---|---|---|---|
| 1 | 8 | 151 | 34.7 ± 0.9 | 7.2 ± 2.1 |
| 2 | 12 | 76 | 11.0 ± 0.9 | 1.7 ± 0.2 |
| 3 | 15 | 158 | 11.7 ± 1.8 | 7.0 ± 1.4 |

TABLE 11

Minimum inhibitory activity of control agents

| Entry | Antimicrobial agent | MIC (µg/mL) S. aureus | MIC (µg/mL) E. coli |
|---|---|---|---|
| 1 | SDS | 122 ± 1 | 325 ± 11 |
| 2 | CAPS/SDS | 131 ± 3 | 388 ± 8 |
| 3 | Cu$_2$bpdpo | 328 ± 7 | 260 ± 12 |
| 4 | Vancomycin | 2.35 ± 0.14 | 12.5 ± 0.2 |
| 6 | Benzalkonium chloride | 4.32 ± 0.01 | 117 ± 1 |
| 5 | Chloramphenicol | 6.11 ± 0.02 | 1.29 ± 0.04 |

TABLE 12

Minimum inhibitory activity of selected microgels over time

| | | | S. aureus MIC (µg/mL) | | E. coli MIC (µg/mL) | |
|---|---|---|---|---|---|---|
| Entry | ligand | template | t = 0 | t = 4 months | t = 0 | t = 4 months |
| 1 | VBbpdpo | Man | 0.64 ± 0.01 | 0.63 ± 0.01 | 2.27 ± 0.09 | 2.28 ± 0.03 |
| 2 | VBbpdpo | EG | 0.70 ± 0.02 | 0.71 ± 0.01 | 2.59 ± 0.09 | 2.60 ± 0.02 |
| 3 | VBbsdpo | Man | 0.39 ± 0.03 | 0.37 ± 0.02 | 1.55 ± 0.02 | 1.56 ± 0.04 |

We claim:
1. A method for inhibiting proliferation of or killing a microbe comprising contacting the microbe with an effective amount of an antimicrobial material to inhibit proliferation of or kill the microbe, wherein the antimicrobial material comprises:
   (a) a carbohydrate-templated microgel, wherein the carbohydrate-templated microgel comprises a network copolymer molecule comprising (i) a monoacrylate monomer, (ii) a crosslinking monomer, and (iii) a ligand monomer; and
   (b) a plurality of metal ions complexed to the ligand of the carbohydrate-templated microgel;
   wherein the carbohydrate-templated microgel is prepared by the copolymerization of the monoacrylate monomer, the crosslinking monomer, and the ligand monomer in the presence of a carbohydrate or a carbohydrate derivative.
2. A method for treating a microbial infection, the method comprising administering an effective amount of an antimicrobial material to a subject in need of a treatment for the microbial infection, wherein the antimicrobial material comprises:
   (a) a carbohydrate-templated microgel, wherein the carbohydrate-templated microgel comprises a network copolymer molecule comprising (i) a monoacrylate monomer, (ii) a crosslinking monomer, and (iii) a ligand monomer; and
   (b) a plurality of metal ions complexed to the ligand of the carbohydrate-templated microgel;
   wherein the carbohydrate-templated microgel is prepared by the copolymerization of the monoacrylate monomer, the crosslinking monomer, and the ligand monomer in the presence of a carbohydrate or a carbohydrate derivative.
3. The method of claim 2, wherein the microbe is a prokaryotic microbe.
4. The method of claim 3, wherein the microbe is a Gram-positive bacteria.
5. The method of claim 3, wherein the microbe is a Gram-negative bacteria.
6. The method of claim 2, wherein the microbe is a biofilm-forming microbe.
7. The method of claim 2, wherein—
   the monoacrylate monomer comprises one or more compounds of the formula $CH_2CHC(=O)OR$ and/or $CH_2C(CH_3)C(=O)OR$ wherein R is selected from a branched or unbranched, substituted or unsubstituted alkyl, a branched or unbranched, substituted or unsubstituted cycloalkyl, a branched or unbranched, substituted or unsubstituted aryl, or any combination thereof;
   the crosslinking monomer comprises one or more compounds selected from the group consisting of a diacrylate, a triacrylate, a tetraacrylate, a pentaacrylate, a hexaacrylate, an alkoxylated crosslinking monomer thereof, or any combination thereof;
   the ligand monomer comprises 1,3-bis(((3-((4-vinylbenzyl)oxy)pyridin-2-yl)methyl)amino)propan-2-ol, 6,6'-(1E,1'E)-((2-hydroxypropane-1,3-diyl)bis(azaneylylidene))bis(methaneylylidene))bis(3-((4-vinylbenzyl)oxy)phenol), or 2,2'-((4-vinylbenzyl)azanediyl)diacetic acid;
   the plurality of metal ions comprise a plurality of copper ions;
   the carbohydrate is a monosaccharide or a disaccharide;
   the carbohydrate derivative is a glycosidase inhibitor and/or a glyconoamidine; or
   any combination thereof.

8. The method of claim 7, wherein—
   the monoacrylate monomer comprises one or more compounds of the formula $CH_2CHC(=O)OR$ and/or $CH_2C(CH_3)C(=O)OR$ wherein R is selected from a branched or unbranched, substituted or unsubstituted alkyl, a branched or unbranched, substituted or unsubstituted cycloalkyl, a branched or unbranched, substituted or unsubstituted aryl, or any combination thereof;
   the crosslinking monomer comprises one or more compounds selected from the group consisting of a diacrylate, a triacrylate, a tetraacrylate, a pentaacrylate, a hexaacrylate, a dimethacrylate, a trimethacrylate, a tetramethacrylate, a pentamethacrylate, a hexamethacrylate, or any combination thereof;
   the ligand monomer comprises a compound of formula 1,3-bis(((3-((4-vinylbenzyl)oxy)pyridin-2-yl)methyl)amino)propan-2-ol, 6,6'-((1E,1'E)-((2-hydroxypropane-1,3-diyl)bis(azaneylylidene))bis(methaneylylidene))bis(3-((4-vinylbenzyl)oxy)phenol), or 2,2'-((4-vinylbenzyl)azanediyl)diacetic acid;
   the plurality of metal ions comprise a plurality of copper ions; and
   the carbohydrate is a monosaccharide or the carbohydrate derivative is a glycosidase inhibitor and/or a glyconoamidine.
9. The method of claim 2, wherein the carbohydrate is galactose or mannose.
10. The method of claim 2, wherein the carbohydrate derivative comprises a compound of formula

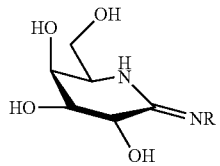

or its tautomer, wherein R is selected from the group consisting of a branched or unbranched, substituted or unsubstituted alkyl, or a branched or unbranched, substituted or unsubstituted cycloalkyl, a branched or unbranched, substituted or unsubstituted alkyl.
11. The method of claim 2, wherein the microgel has a hydrodynamic diameter of less than 300 nm.
12. A method for hydrolyzing a glycosidic bond, the method comprising contacting the antimicrobial material as in claim 1 with a substrate, wherein the substrate comprises a carbohydrate or a carbohydrate derivative.
13. An antimicrobial material comprising an effective amount of the material according to claim 2 to inhibit proliferation of or kill a microbe.
14. A pharmaceutical composition comprising a therapeutically effective amount of the antimicrobial material of claim 13 and one or more pharmaceutically acceptable carriers, excipients, or diluents.
15. An article having lowered susceptibility to the formation of a biofilm thereon comprising the antimicrobial material of claim 13 applied to a surface of the article.
16. A method of preparing an article having lowered susceptibility to the formation of a biofilm thereon, the method comprising applying the antimicrobial material of claim 13 to a surface of the article.

* * * * *